United States Patent
Chen et al.

(10) Patent No.: US 11,833,211 B2
(45) Date of Patent: Dec. 5, 2023

(54) METHODS OF SUPPRESSION AND TREATMENT OF DISEASE COMPRISING ADMINISTERING BICYCLE PEPTIDE LIGANDS SPECIFIC FOR EPHA2

(71) Applicant: BicycleTx Limited, Cambridge (GB)

(72) Inventors: Liuhong Chen, Cambridge (GB); Philip Huxley, Cambridge (GB); Silvia Pavan, Cambridge (GB); Katerine Van Rietschoten, Cambridge (GB)

(73) Assignee: BicycleTx Limited, Cambridge (GB)

( * ) Notice: Subject to any disclaimer, the term of this patent is extended or adjusted under 35 U.S.C. 154(b) by 0 days.

(21) Appl. No.: 17/934,896

(22) Filed: Sep. 23, 2022

(65) Prior Publication Data

US 2023/0144799 A1    May 11, 2023

Related U.S. Application Data

(62) Division of application No. 16/220,685, filed on Dec. 14, 2018, now Pat. No. 11,484,602.

(30) Foreign Application Priority Data

| Dec. 19, 2017 | (GB) | 1721259 |
| Mar. 14, 2018 | (GB) | 1804102 |
| Nov. 14, 2018 | (GB) | 1818603 |

(51) Int. Cl.
*A61K 47/64* (2017.01)
*A61P 35/00* (2006.01)
(Continued)

(52) U.S. Cl.
CPC .......... *A61K 47/6415* (2017.08); *A61K 38/05* (2013.01); *A61K 38/10* (2013.01);
(Continued)

(58) Field of Classification Search
CPC .... A61K 47/6415; A61K 47/64; A61K 38/05; A61K 38/10; A61K 47/65; A61K 47/62; A61P 35/00; C07K 7/08
See application file for complete search history.

(56) References Cited

U.S. PATENT DOCUMENTS

| 4,650,750 A | 3/1987 | Giese |
| 4,709,016 A | 11/1987 | Giese |

(Continued)

FOREIGN PATENT DOCUMENTS

| WO | WO-2001042246 A2 | 6/2001 |
| WO | WO-2003063794 A2 | 8/2003 |

(Continued)

OTHER PUBLICATIONS

Adams, "Molecular control of arterial-venous blood vessel identity," J Anat. Jan. 2003;202(1):105-12.

(Continued)

*Primary Examiner* — Kevin S Orwig
*Assistant Examiner* — John Michael Cronin
(74) *Attorney, Agent, or Firm* — Dechert LLP; Andrea L. C. Reid; Gang Wang

(57) ABSTRACT

The present invention relates to polypeptides which are covalently bound to non-aromatic molecular scaffolds such that two or more peptide loops are subtended between attachment points to the scaffold. In particular, the invention describes peptides which are high affinity binders of the Eph receptor tyrosine kinase A2 (EphA2). The invention also includes drug conjugates comprising said peptides, conjugated to one or more effector and/or functional groups, to pharmaceutical compositions comprising said peptide ligands and drug conjugates and to the use of said peptide ligands and drug conjugates in preventing, suppressing or (Continued)

treating a disease or disorder characterised by overexpression of EphA2 in diseased tissue (such as a tumour).

20 Claims, 29 Drawing Sheets

Specification includes a Sequence Listing.

(51) Int. Cl.
| | |
|---|---|
| A61K 47/65 | (2017.01) |
| A61K 38/10 | (2006.01) |
| A61K 38/05 | (2006.01) |
| A61K 47/62 | (2017.01) |
| C07K 7/08 | (2006.01) |

(52) U.S. Cl.
CPC .............. *A61K 47/62* (2017.08); *A61K 47/64* (2017.08); *A61K 47/65* (2017.08); *A61P 35/00* (2018.01); *C07K 7/08* (2013.01)

(56) References Cited

U.S. PATENT DOCUMENTS

| | | | |
|---|---|---|---|
| 5,360,819 | A | 11/1994 | Giese |
| 5,516,931 | A | 5/1996 | Giese et al. |
| 5,602,273 | A | 2/1997 | Giese et al. |
| 5,604,104 | A | 2/1997 | Giese et al. |
| 5,610,020 | A | 3/1997 | Giese et al. |
| 5,650,270 | A | 7/1997 | Giese et al. |
| 6,326,144 | B1 | 12/2001 | Bawendi et al. |
| 6,468,808 | B1 | 10/2002 | Nie et al. |
| 7,151,047 | B2 | 12/2006 | Chan et al. |
| 7,192,785 | B2 | 3/2007 | Nie et al. |
| 8,138,347 | B2 | 3/2012 | Knight et al. |
| 8,680,022 | B2 | 3/2014 | Gregory et al. |
| 8,685,890 | B2 | 4/2014 | Winter et al. |
| 8,778,844 | B2 | 7/2014 | Winter et al. |
| 9,518,081 | B2 | 12/2016 | Winter et al. |
| 9,644,201 | B2 | 5/2017 | Winter et al. |
| 9,657,288 | B2 | 5/2017 | Winter et al. |
| 9,670,482 | B2 | 6/2017 | Winter et al. |
| 9,670,484 | B2 | 6/2017 | Winter et al. |
| 9,868,767 | B2 | 1/2018 | Pei et al. |
| 9,932,367 | B2 | 4/2018 | Stace et al. |
| 9,994,617 | B2 | 6/2018 | Tite et al. |
| 10,118,947 | B2 | 11/2018 | Teufel et al. |
| 10,294,274 | B2 | 5/2019 | Teufel et al. |
| 10,441,663 | B2 | 10/2019 | Bennett et al. |
| 10,532,106 | B2 | 1/2020 | Teufel et al. |
| 10,624,968 | B2 | 4/2020 | Bennett et al. |
| 10,800,813 | B2 | 10/2020 | Tite et al. |
| 10,875,894 | B2 | 12/2020 | Chen et al. |
| 10,919,937 | B2 | 2/2021 | Beswick et al. |
| 11,306,123 | B2 | 4/2022 | Mudd et al. |
| 11,312,749 | B2 | 4/2022 | Mudd et al. |
| 11,332,500 | B2 | 5/2022 | Mudd et al. |
| 11,484,602 | B2 * | 11/2022 | Chen ..................... A61K 38/05 |
| 11,696,956 | B2 | 7/2023 | Chen et al. |
| 2002/0164788 | A1 | 11/2002 | Ellis et al. |
| 2005/0169931 | A1 | 8/2005 | Kinch et al. |
| 2017/0067045 | A1 | 3/2017 | Winter et al. |
| 2017/0190743 | A1 | 7/2017 | Pei et al. |
| 2018/0311300 | A1 | 11/2018 | Beswick et al. |
| 2018/0362585 | A1 | 12/2018 | Teufel et al. |
| 2018/0371020 | A1 | 12/2018 | Bennett et al. |
| 2019/0134213 | A1 | 5/2019 | Teufel et al. |
| 2019/0184025 | A1 | 6/2019 | Chen et al. |
| 2019/0263866 | A1 | 8/2019 | Chen et al. |
| 2019/0307836 | A1 | 10/2019 | Keen et al. |
| 2019/0389906 | A1 | 12/2019 | Beswick et al. |
| 2020/0190213 | A1 | 6/2020 | Preyer et al. |
| 2020/0255477 | A1 | 8/2020 | Chen et al. |
| 2020/0338203 | A1 | 10/2020 | Chen et al. |
| 2020/0354406 | A1 | 11/2020 | Stephen et al. |
| 2021/0040154 | A1 | 2/2021 | Mudd et al. |
| 2021/0069287 | A1 | 3/2021 | Mudd et al. |
| 2021/0079045 | A1 | 3/2021 | Bennett et al. |
| 2021/0101932 | A1 | 4/2021 | Chen et al. |
| 2021/0101933 | A1 | 4/2021 | Chen et al. |
| 2021/0101937 | A1 | 4/2021 | Mudd et al. |
| 2021/0147484 | A1 | 5/2021 | Beswick et al. |
| 2021/0261620 | A1 | 8/2021 | Teufel et al. |
| 2021/0299210 | A2 | 9/2021 | Keen et al. |
| 2022/0184222 | A1 | 6/2022 | Bennett et al. |
| 2022/0227811 | A1 | 7/2022 | Mudd et al. |
| 2022/0242911 | A1 | 8/2022 | Mudd et al. |
| 2022/0257784 | A1 | 8/2022 | Upadhyaya et al. |
| 2022/0275053 | A1 | 9/2022 | Upadhyaya et al. |
| 2022/0306694 | A1 | 9/2022 | Mudd et al. |
| 2023/0025916 | A1 | 1/2023 | Bennett et al. |
| 2023/0129258 | A1 | 4/2023 | Upadhyaya et al. |

FOREIGN PATENT DOCUMENTS

| | | |
|---|---|---|
| WO | WO-2004005348 A1 | 1/2004 |
| WO | WO-2004019973 A1 | 3/2004 |
| WO | WO-2004077062 A2 | 9/2004 |
| WO | WO-2004089925 A1 | 10/2004 |
| WO | WO-2005007623 A2 | 1/2005 |
| WO | WO-2005103083 A2 | 11/2005 |
| WO | WO-2005113554 A2 | 12/2005 |
| WO | WO-2006078161 A1 | 7/2006 |
| WO | WO-2006078846 A1 | 7/2006 |
| WO | WO-2006122806 A2 | 11/2006 |
| WO | WO-2007016176 A2 | 2/2007 |
| WO | WO-2007044729 A2 | 4/2007 |
| WO | WO-2007053452 A1 | 5/2007 |
| WO | WO-2007070514 A1 | 6/2007 |
| WO | WO-2007084786 A1 | 7/2007 |
| WO | WO-2007129161 A2 | 11/2007 |
| WO | WO-2008033561 A2 | 3/2008 |
| WO | WO-2008039218 A2 | 4/2008 |
| WO | WO-2008109943 A1 | 9/2008 |
| WO | WO-2008157490 A1 | 12/2008 |
| WO | WO-2009098450 A2 | 8/2009 |
| WO | WO-2009114512 A1 | 9/2009 |
| WO | WO-2010089115 A1 | 8/2010 |
| WO | WO-2011018227 A2 | 2/2011 |
| WO | WO-2011090760 A1 | 7/2011 |
| WO | WO-2012057624 A1 | 5/2012 |
| WO | WO-2013050617 A1 | 4/2013 |
| WO | WO-2014164693 A2 | 10/2014 |
| WO | WO-2015171938 A1 | 11/2015 |
| WO | WO-2016067035 A1 | 5/2016 |
| WO | WO-2016171242 A1 | 10/2016 |
| WO | WO-2016174103 A1 | 11/2016 |
| WO | WO-2017161069 A1 | 9/2017 |
| WO | WO-2017173408 A1 | 10/2017 |
| WO | WO-2017182672 A1 | 10/2017 |
| WO | WO-2017191460 A1 | 11/2017 |
| WO | WO-2018115203 A1 | 6/2018 |
| WO | WO-2018115204 A1 | 6/2018 |
| WO | WO-2018127699 A1 | 7/2018 |
| WO | WO-2018156740 A1 | 8/2018 |
| WO | WO-2018197509 A1 | 11/2018 |
| WO | WO-2019002842 A1 | 1/2019 |
| WO | WO-2019025811 A1 | 2/2019 |
| WO | WO-2019034866 A1 | 2/2019 |
| WO | WO-2019034868 A1 | 2/2019 |
| WO | WO-2019122860 A1 | 6/2019 |
| WO | WO-2019122861 A1 | 6/2019 |
| WO | WO-2019122863 A1 | 6/2019 |
| WO | WO-2019136442 A1 | 7/2019 |
| WO | WO-2019162682 A1 | 8/2019 |
| WO | WO-2019193328 A1 | 10/2019 |
| WO | WO-2019226617 A1 | 11/2019 |
| WO | WO-2019243313 A1 | 12/2019 |
| WO | WO-2019243832 A1 | 12/2019 |
| WO | WO-2019243833 A1 | 12/2019 |
| WO | WO-2020084305 A1 | 4/2020 |
| WO | WO-2020120984 A1 | 6/2020 |
| WO | WO-2020128526 A1 | 6/2020 |
| WO | WO-2020201753 A1 | 10/2020 |

(56) References Cited

FOREIGN PATENT DOCUMENTS

| | | |
|---|---|---|
| WO | WO-2020225577 A1 | 11/2020 |
| WO | WO-2021019243 A1 | 2/2021 |
| WO | WO-2021019244 A1 | 2/2021 |
| WO | WO-2021019245 | 2/2021 |
| WO | WO-2021019245 A1 | 2/2021 |
| WO | WO-2021019246 A1 | 2/2021 |
| WO | WO-2021028686 A1 | 2/2021 |
| WO | WO-2021064428 A1 | 4/2021 |
| WO | WO-2021105694 A1 | 6/2021 |
| WO | WO-2021250418 A1 | 12/2021 |
| WO | WO-2022038158 A1 | 2/2022 |
| WO | WO-2022148975 A1 | 7/2022 |
| WO | WO-2022148979 A1 | 7/2022 |

OTHER PUBLICATIONS

Annunziata et al., "Phase 1, open-label study of MEDI-547 in patients with relapsed or refractory solid tumors," Invest New Drugs. Feb. 2013;31(1):77-84.

Bicycle Therapeutics, "Bicycle Therapeutics to Present on BT5528, a Bicycle Toxin Conjugate Targeting EphA2 for the Treatment of Solid Tumours, at World ADC 2019," Business Wire Release. Mar. 5, 2019.

Ausiello et al., "Functional topography of discrete domains of human CD38," Tissue Antigens. Dec. 2000;56(6):539-47.

Bennett et al., "Abstract 5854: BT5528, a Bicycle Toxin Conjugate targeting EphA2 has potent anti-tumor activity without bleeding or coagulation abnormalities in preclinical models." Cancer Res. 2018;78(13 suppl):5854.

Bennett et al., "BT5528, a Bicycle Toxin Conjugate targeting EphA2 has potent anti-tumor activity without bleeding or coagulation abnormalities in preclinical models," AACR Annual Meeting 2018.

Bennett, "BT1718, a Bicycle Drug Conjugate (BTC): Profound Efficacy Without Bleeding and Coagulation Abnormalities in Animal Models," AACR Annual Meeting 2019. 4481.

Bennett et al., "MMAE Delivery Using the Bicycle Toxin Conjugate BT5528," Mol Cancer Ther. Jul. 2020;19(7):1385-1394.

Berge et al., "Pharmaceutical salts," J Pharm Sci. 1977;66(1):1-19.

Binda et al., "The EphA2 receptor drives self-renewal and tumorigenicity in stem-like tumor-propagating cells from human glioblastomas," Cancer Cell. Dec. 11, 2012; 22(6); 765-80.

Booth et al., "Crowd control in the crypt," Nat Med. Dec. 2002;8(12):1360-1.

Brannan et al., "EphA2 in the early pathogenesis and progression of non-small cell lung cancer," Cancer Prev Res (Phila). Dec. 2009;2(12):1039-49.

Brantley-Sieders et al., "Eph receptor tyrosine kinases in tumor and tumor microenvironment," Curr Pharm Des. 2004; 10(27); 3431-42.

Brantley-Sieders et al., "Eph/ephrin profiling in human breast cancer reveals significant associations between expression level and clinical outcome," PLoS One. 2011; 6(9): e24426.

Brantley-Sieders et al., "Impaired tumor microenvironment in EphA2-deficient mice inhibits tumor angiogenesis and metastatic progression," FASEB J. Nov. 2005; 19(13):1884-6.

Centers for Disease Control and Prevention, "What Can I Do to Reduce My Risk of Ovarian Cancer?" Division of Cancer Prevention and Control. Aug. 31, 2022.

Chan and Nie, "Quantum dot bioconjugates for ultrasensitive nonisotopic detection," Science. Sep. 25, 1998; 281 (5385): 2016-8.

Chang et al., "Five different anti-prostate-specific membrane antigen (PSMA) antibodies confirm PSMA expression in tumor-associated neovasculature," Cancer Res. Jul. 1, 1999; 59(13):3192-8.

Chen et al., "Structurally diverse cyclisation linkers impose different backbone conformations in bicyclic peptides," Chembiochem. May 7, 2012; 13(7): 1032-8.

Cheng et al., "Blockade of EphA receptor tyrosine kinase activation inhibits vascular endothelial cell growth factor-induced angiogenesis," Mol Cancer Res. Nov. 2002; 1(1): 2-11.

Cherney et al., "Macrocyclic amino carboxylates as selective MMP-8 inhibitors," J Med Chem. May 21, 1998;41(11):1749-51.

Chiche et al., "Hypoxia-inducible carbonic anhydrase IX and XII promote tumor cell growth by counteracting acidosis through the regulation of the intracellular pH," Cancer Res. Jan. 1, 2009,69(1):358-68.

Dagher et al., "c-Kit and CD38 are expressed by long-term reconstituting hematopoietic cells present in the murine yolk sac," Biol Blood Marrow Transplant. 1998;4(2):69-74.

Deaglio et al., "CD38 is a signaling molecule in B-cell chronic lymphocytic leukemia cells," Blood. Sep. 15, 2003;102(6):2146-55.

Deyle et al., "Phage Selection of Cyclic Peptides for Application in Research and Drug Development." Acc Chem Res. 2017;50(8):1866-1874.

Di, "Strategic approaches to optimizing peptide ADME properties," AAPS J. Jan. 2015;17(1):134-43.

Driggers et al., "The exploration of macrocycles for drug discovery—an underexploited structural class," Nat Rev Drug Discov. Jul. 2008;7(7):608-24.

Dunne et al., "EphA2 Expression Is a Key Driver of Migration and Invasion and a Poor Prognostic Marker in Colorectal Cancer," Clin Cancer Res. Jan. 1, 2016;22(1):230-242.

Duong and Rodan, "The role of integrins in osteoclast function," J Bone Miner Metab. 1999;17(1):1-6.

Funaro et al., "Human CD38 is associated to distinct molecules which mediate transmembrane signaling in different lineages," Eur J Immunol. Oct. 1993;23(10):2407-11.

Funaro et al., "Involvement of the multilineage CD38 molecule in a unique pathway of cell activation and proliferation," J Immunol. Oct. 15, 1990;145(8):2390-6.

Gandhi et al., "MP69-11 Carbonic Anhydrase IX Assay: A Paradigm Shift in Diagnosis of Malignant Cystic Renal Lesions," J Urol. May 18, 2015;193(4S):e870-e871.

Guo et al., "Prognostic significance of combinations of RNA-dependent protein kinase and EphA2 biomarkers for NSCLC," J Thorac Oncol. Mar. 2013;8(3):301-8.

Heinis et al., "Phage-encoded combinatorial chemical libraries based on bicyclic peptides," Nat. Chem. Biol. 2009;5(7):502-7.

Hess et al., "Molecular regulation of tumor cell vasculogenic mimicry by tyrosine phosphorylation: role of epithelial cell kinase (Eck/EphA2)," Cancer Res. Apr. 15, 2001;61(8):3250-5.

Hoshino et al., "Mapping of the catalytic and epitopic sites of human CD38/NAD+ glycohydrolase to a functional domain in the carboxyl terminus," J Immunol. Jan. 15, 1997;158(2):741-7.

PCT International Search Report and Written Opinion from PCT/GB2018/051779, dated Aug. 23, 2018.

Jackson et al., "A human antibody-drug conjugate targeting EphA2 inhibits tumor growth in vivo," Cancer Res. Nov. 15, 2008;68(22):9367-74.

Jin et al., "(alpha)V(beta)3 Integrin-Targeted Radionuclide Therapy with 64Cu-cyclam-RAFT-c(-RGDfK-)4," Mol Cancer Ther. Sep. 2016;15(9):2076-85.

Kemp and McNamara, "Conformationally restricted cyclic nonapeptides derived from L-cysteine and LL-3-amino-2-piperidone-6-carboxylic acid (LL-Acp), a potent .beta.-turn-inducing dipeptide analog," J Org Chem. 1985;50(26):5834-8.

Kinch et al., "Predictive value of the EphA2 receptor tyrosine kinase in lung cancer recurrence and survival," Clin Cancer Res. Feb. 2003;9(2):613-8.

Kitanaka et al., "CD38 ligation in human B cell progenitors triggers tyrosine phosphorylation of CD19 and association of CD19 with lyn and phosphatidylinositol 3-kinase," J Immunol. Jul. 1, 1997;159(1):184-92.

Kitanaka et al., "CD38-mediated signaling events in murine pro-B cells expressing human CD38 with or without its cytoplasmic domain," J Immunol. Feb. 15, 1999;162(4):1952-8.

Konopleva et al., "Ligation of cell surface CD38 protein with agonistic monoclonal antibody induces a cell growth signal in myeloid leukemia cells," J Immunol. Nov. 1, 1998;161(9):4702-8.

(56) References Cited

OTHER PUBLICATIONS

Kumagai et al., "Ligation of CD38 suppresses human B lymphopoiesis," J Exp Med. Mar. 1, 1995;181(3):1101-10.
Lee et al., "ADP-ribosyl cyclase and CD38. Multi-functional enzymes in Ca+2 signaling," Adv Exp Med Biol. 1997;419:411-9.
Lee and Aarhus, "ADP-ribosyl cyclase: an enzyme that cyclizes NAD+ into a calcium-mobilizing metabolite," Cell Regul. Mar. 1991;2(3):203-9.
Lee et al., "Structural determination of a cyclic metabolite of NAD+ with intracellular Ca2+-mobilizing activity," J Biol Chem. Jan. 25, 1989;264(3):1608-15.
Li et al., "Up-regulation of EphA2 and down-regulation of EphrinA1 are associated with the aggressive phenotype and poor prognosis of malignant glioma," Tumour Biol. Oct. 2010;31(5):477-88.
Lin et al., "EphA2 overexpression is associated with angiogenesis in ovarian cancer," Cancer. Jan. 15, 2007;109(2):332-40.
Lund et al., "CD38 signaling in B lymphocytes is controlled by its ectodomain but occurs independently of enzymatically generated ADP-ribose or cyclic ADP-ribose," J Immunol. Mar. 1, 1999;162(5):2693-702.
Mallone et al., "Signaling through CD38 induces NK cell activation," Int Immunol. Apr. 1, 2001;13(4):397-409.
Marmé, "VEGFs, angiopoietins, Ephrins and their receptors: putative targets for tumor therapy?" Ann Hematol. 2002;81 Suppl 2:S66.
Merritt et al., "Analysis of EphA2 expression and mutant p53 in ovarian carcinoma," Cancer Biol Ther. Oct. 2006;5(10):1357-60.
Morra et al., "CD38 is functionally dependent on the TCR/CD3 complex in human T cells," FASEB J. May 1998;12(7):581-92.
Mudali et al., "Patterns of EphA2 protein expression in primary and metastatic pancreatic carcinoma and correlation with genetic status," Clin Exp Metastasis. 2006;23(7-8):357-65.
Bicycle Tx Limited, "Study BT5528-100 in Patients With Advanced Solid Tumors Associated With EphA2 Expression," ClinicalTrials. gov Identifier NCT04180371. First Posted Nov. 27, 2019; Accessed Dec. 30, 2022: https://clinicaltrials.gov/ct2/show/NCT04180371.
Bicycle Therapeutics, "Bicycle Therapeutics to Present New BT1718 Data in the "New Drugs on the Horizon" Session at the 2018 American Association for Cancer Research Meeting," Press Release. Apr. 3, 2018.
Nakamoto and Bergemann, "Diverse roles for the Eph family of receptor tyrosine kinases in carcinogenesis," Microsc Res Tech. Oct. 1, 2002;59(1):58-67.
Nakamura et al., "EPHA2/EFNA1 expression in human gastric cancer," Cancer Sci. Jan. 2005;96(1):42-7.
Nakamura et al., "Involvement of alpha(v)beta3 integrins in osteoclast function," J Bone Miner Metab. 2007;25(6):337-44.
Nan et al., "Dual function glutamate-related ligands: discovery of a novel, potent inhibitor of glutamate carboxypeptidase II possessing mGluR3 agonist activity," J Med Chem. Mar. 9, 2000;43(5):772-4.
Neri and Supuran, "Interfering with pH regulation in tumours as a therapeutic strategy," Nat Rev Drug Discov. Sep. 16, 2011;10(10):767-77.
Oliver et al., "Mouse CD38 is down-regulated on germinal center B cells and mature plasma cells," J Immunol. Feb. 1, 1997;158(3):1108-15.
Partida-Sánchez et al., "Cyclic ADP-ribose production by CD38 regulates intracellular calcium release, extracellular calcium influx and chemotaxis in neutrophils and is required for bacterial clearance in vivo," Nat Med. Nov. 2001;7(11):1209-16.
Partida-Sánchez et al., "Regulation of dendritic cell trafficking by the ADP-ribosyl cyclase CD38: impact on the development of humoral immunity," Immunity. Mar. 2004;20(3):279-91.
PCT International Search Report and Written Opinion from PCT/GB2020/050874 dated Jun. 17, 2020.
PCT International Search Report and Written Opinion from PCT/GB2021/051451, dated Sep. 22, 2021.
Pietraszek et al., "Lumican: a new inhibitor of matrix metalloproteinase-14 activity," FEBS Lett. Nov. 28, 2014;588(23):4319-24.
Poliakov et al., "Diverse roles of eph receptors and ephrins in the regulation of cell migration and tissue assembly," Dev Cell. Oct. 2004;7(4):465-80.
Ramirez et al., "Defining causative factors contributing in the activation of hedgehog signaling in diffuse large B-cell lymphoma," Leuk Res. Oct. 2012;36(10):1267-73.
Randall et al., "Expression of murine CD38 defines a population of long-term reconstituting hematopoietic stem cells," Blood. May 15, 1996;87(10):4057-67.
Remacle et al., "Novel MT1-MMP small-molecule inhibitors based on insights into hemopexin domain function in tumor growth," Cancer Res. May 1, 2012;72(9):2339-49.
Ridderstad and Tarlinton, "Kinetics of establishing the memory B cell population as revealed by CD38 expression," J Immunol. May 15, 1998;160(10):4688-95.
Rodan and Rodan, "Integrin function in osteoclasts," J Endocrinol. Sep. 1997;154 Suppl:S47-56.
Ross and Christiano, "Nothing but skin and bone," J Clin Invest. May 2006;116(5):1140-9.
Rostovtsev et al., "A stepwise huisgen cycloaddition process: copper(I)-catalyzed regioselective "ligation" of azides and terminal alkynes," Angew Chem Int Ed Engl. Jul. 15, 2002;41(14):2596-9.
Schülke et al., "The homodimer of prostate-specific membrane antigen is a functional target for cancer therapy," Proc Natl Acad Sci U S A. Oct. 28, 2003;100(22):12590-5.
Sounni et al., "MT1-MMP expression promotes tumor growth and angiogenesis through an up-regulation of vascular endothelial growth factor expression," FASEB J. Apr. 2002;16(6):555-64.
Stein et al., "Eph receptors discriminate specific ligand oligomers to determine alternative signaling complexes, attachment, and assembly responses," Genes Dev. Mar. 1, 1998;12(5):667-678.
Stevenson et al., "Preliminary studies for an immunotherapeutic approach to the treatment of human myeloma using chimeric anti-CD38 antibody," Blood. Mar. 1, 1991;77(5):1071-9.
Sun et al., "Carbohydrate and protein immobilization onto solid surfaces by sequential Diels-Alder and azide-alkyne cycloadditions," Bioconjug Chem. Jan.-Feb. 2006;17(1):52-7.
Supuran, "Carbonic anhydrases: novel therapeutic applications for inhibitors and activators," Nat Rev Drug Discov. Feb. 2008;7(2):168-81.
Tandon et al., "Emerging strategies for EphA2 receptor targeting for cancer therapeutics." Expert Opin Ther Targets. 2011;15(1):31-51.
Tasch et al., "A unique folate hydrolase, prostate-specific membrane antigen (PSMA): a target for immunotherapy?" Crit Rev Immunol. 2001;21(1-3):249-61.
Teitelbaum, "Osteoclasts, integrins, and osteoporosis," J Bone Miner Metab. Oct. 2000;18(6):344-9.
Teitelbaum, "Osteoporosis and Integrins," J Clin Endocrinol Metab. Apr. 2005;90(4):2466-8.
Teti et al., "The role of the alphaVbeta3 integrin in the development of osteolytic bone metastases: a pharmacological target for alternative therapy?" Calcif Tissue Int. Oct. 2002;71(4):293-9.
Teufel et al., "Backbone-driven collapse in unfolded protein chains," J Mol Biol. Jun. 3, 2011;409(2):250-62.
Timmerman et al., "Rapid and quantitative cyclization of multiple peptide loops onto synthetic scaffolds for structural mimicry of protein surfaces," Chembiochem. May 2005;6(5):821-4.
Todisco et al., "CD38 ligation inhibits normal and leukemic myelopoiesis," Blood. Jan. 15, 2000;95(2):535-42.
U.S. Appl. No. 16/771,186, filed Jun. 9, 2020.
U.S. Appl. No. 17/592,966, filed Feb. 4, 2022.
U.S. Appl. No. 17/630,314, filed Jan. 26, 2022.
U.S. Appl. No. 17/630,747, filed Jan. 27, 2022.
U.S. Appl. No. 17/655,822, filed Mar. 22, 2022.
U.S. Appl. No. 17/663,169, filed May 12, 2022.
U.S. Appl. No. 17/779,226, filed May 24, 2022.
Uckun, "Regulation of human B-cell ontogeny," Blood. Nov. 15, 1990;76(10):1908-23.
Walker-Daniels et al., "Overexpression of the EphA2 tyrosine kinase in prostate cancer," Prostate. Dec. 1, 1999;41(4):275-80.
Wallbrecher et al., "Exploration of the design principles of a cell-penetrating bicylic peptide scaffold," Bioconjug Chem. May 21, 2014;25(5):955-64.

(56) References Cited

OTHER PUBLICATIONS

Wang et al., "Probing for integrin alpha v beta3 binding of RGD peptides using fluorescence polarization," Bioconjug Chem. May-Jun. 2005;16(3):729-34.

Wang, "An exact mathematical expression for describing competitive binding of two different ligands to a protein molecule," FEBS Lett. Feb. 27, 1995;360(2):111-4.

Wind et al., "Measuring carbonic anhydrase IX as a hypoxia biomarker: differences in concentrations in serum and plasma using a commercial enzyme-linked immunosorbent assay due to influences of metal ions," Ann Clin Biochem. Mar. 2011;48(Pt 2):112-20.

Wu et al., "Structures of the CXCR4 chemokine GPCR with small-molecule and cyclic peptide antagonists," Science. Nov. 19, 2010;330(6007):1066-71.

Wykosky et al., "EphA2 as a novel molecular marker and target in glioblastoma multiforme," Mol Cancer Res. Oct. 2005;3(10):541-51.

Xiong et al., "Crystal structure of the extracellular segment of integrin alpha Vbeta3 in complex with an Arg-Gly-Asp ligand," Science. Apr. 5, 2002;296(5565):151-5.

Yang et al., "Overexpression of EphA2, MMP-9, and MVD-CD34 in hepatocellular carcinoma: Implications for tumor progression and prognosis," Hepatol Res. Dec. 2009;39(12):1169-77.

Yuan et al., "Over-expression of EphA2 and EphrinA-1 in human gastric adenocarcinoma and its prognostic value for postoperative patients," Dig Dis Sci. Nov. 2009;54(11):2410-7.

Zelinski et al., "EphA2 overexpression causes tumorigenesis of mammary epithelial cells," Cancer Res. Mar. 1, 2001;61(5):2301-6.

Zhao et al., "Structural basis of specificity of a peptidyl urokinase inhibitor, upain-1," J Struct Biol. Oct. 2007;160(1):1-10.

Zhuang et al., "Elevation of receptor tyrosine kinase EphA2 mediates resistance to trastuzumab therapy," Cancer Res. Jan. 1, 2010;70(1):299-308.

Zilber et al., "CD38 expressed on human monocytes: a coaccessory molecule in the superantigen-induced proliferation," Proc Natl Acad Sci U S A. Mar. 14, 2000;97(6):2840-5.

Zubiaur et al., "CD38 ligation results in activation of the Raf-1/mitogen-activated protein kinase and the CD3-zeta/zeta-associated protein-70 signaling pathways in Jurkat T lymphocytes," J Immunol. Jul. 1, 1997;159(1):193-205.

Zupo et al., "CD38 signaling by agonistic monoclonal antibody prevents apoptosis of human germinal center B cells," Eur J Immunol. May 1994;24(5):1218-22.

PCT International Search Report and Written Opinion from PCT/GB2018/053678, dated Mar. 11, 2019.

U.S. Appl. No. 17/590,875, filed Feb. 2, 2022.

Loktev et al., "Multicyclic Peptides as Scaffolds for the Development of Tumor Targeting Agents," Current Medicinal Chemistry, 2017, vol. 24, pp. 2141-2155.

Morrison, "Chemical Strategies for Bicyclic Peptide Formation," Univ. of Leeds, Sep. 2015, pp. 1-60.

Mulder et al., "Scaffold Optimization in Discontinuous Epitope Containing Protein Mimics of gp120 Using Smart Libraries," Org. Biomol. Chem. 2013, vol. 11, pp. 2676-2684.

Pickens et al., "Practical Considerations, Challenges and Limitations of Bioconjugation via Azide-Alkyne Cycloaddition," Bioconjugate Chem., 2018, vol. 29, pp. 686-701.

Rhodes and Pei, "Bicyclic Peptides as Next-Generation Therapeutics," Chemistry. Sep. 18, 2017;23(52):12690-12703.

Smeenk et al., "Reconstructing the discontinuous and conformational (beta)1/(beta)3-loop binding site on hFSH/hCG by using highly constrained multicyclic peptides," Chembiochem. Jan. 2, 2015;16(1):91-9.

Upadhyaya, "Activation of CD137 Using Multivalent and Tumour Targeted Bicyclic Peptides," XP055669343, URL:https://www.bicycletherapeutics.com/wp-content/uploads/PU_2019-Peptide-Congress_publication.pdf, Peptide Congress, Apr. 25, 2019, 25 Pages.

PCT International Search Report and Written Opinion from PCT/GB2020/051827, dated Oct. 23, 2020.

U.S. Appl. No. 18/313,983, filed May 8, 2023.

U.S. Appl. No. 18/001,374, filed Dec. 9, 2022.

U.S. Appl. No. 18/345,506, filed Jun. 30, 2023.

PCT International Search Report and Written Opinion from PCT/GB2020/051923, dated Feb. 18, 2021.

Hurov et al., "T7480, a novel fully synthetic tumor-targeted immune cell agonist (TICA(TM)) induces tumor localized CD137 agonism" 2020 URL: https://www.bicycletherapeutics.com/wp-content/uploads/2020-06-16-BT7480-AACR-2020-poster-P5552_Final_CD137-in-title-002.pdf.

PCT International Search Report and Written Opinion from PCT/GB2020/051831, dated Feb. 4, 2021.

Anonymous, "Constrained peptides Unconstrained thinking Forward-looking statements", Aug. 1, 2019 (Aug. 1, 2019), p. 1-30, URL:https://investors.bicycletherapeutics.com/static-files/1e4832c5-1181-4fcc-acd9-c1dbb1c8b594.

Beswick, "Bicycles—An entirely new class of therapeutics," 2019; URL:https://www.bicycletherapeutics.com/wp-content/uploads/RSC-02-May 2019.pdf.

PCT International Search Report and Written Opinion from PCT/GB2020/052445, dated Apr. 4, 2021.

U.S. Appl. No. 18/271,360, filed Jul. 7, 2023.

Dufort et al., "789: Generation of a Bicycle NK-TICA(TM), a novel NK cell engaging molecule to enhance targeted tumor cytotoxicity," 2021; URL:https://jitc.bmj.com/content/jitc/9/Suppl_2/A824.full.pdf.

PCT International Search Report and Written Opinion from PCT/GB2022/050044, dated Jul. 14, 2022.

U.S. Appl. No. 18/271,593, filed Jul. 10, 2023.

PCT International Search Report and Written Opinion from PCT/GB2022/050055, dated Jul. 14, 2022.

Anonymous, "Bicycle Conjugates," 2021; URL:https://web.archive.org/web/20210104063050/https://www.bicycletherapeutics.com/programs/.

Anonymous, "Bicycle Therapeutics to Present New Translational Research for BT5528 and Preclinical Data for Tumor-targeted Immune Cell Agonists at the AACR Virtual Annual Meeting II," 2020; URL:https://www.businesswire.com/news/home/20200515005111/en/Bicycle-Therapeutics-to-Present-New-Translational-Research-for-BT5528-and-Preclinical-Data-for-Tumor-targeted-Immune-Cell-Agonists-at-the-AACR-Virtual-Annual-Meeting-II.

Bennett et al., "Abstract 5855: Bicycle Drug Conjugates Targeting EphA2 for the Treatment of Solid Tumors: Discovery and Selection of BT5528," Cancer Research, 2018, 4 Pages.

Bennett et al., "Development of BT1718, a Bicycle Drug Conjugate (BDC) targeting MT1-MMP for treatment of solid tumours," European Journal of Cancer. 2016;69(1):S21.

Bennett, "BT5528, an EphA2-Targeting Bicycle Toxin Conjugate (BTC): Profound Efficacy Without Bleeding and Coagulation Abnormalities in Animal Models," Association for Cancer Research Annual Meeting, 2019, 11 Pages.

Chen et al., "Peptide Ligands Stabilized by Small Molecules," Angewandte Chemie International Edition. 2014;56(6):1602-1606.

Deonarain et al., "Small-Format Drug Conjugates: A Viable Alternative to ADCs for Solid Tumours?" Antibodies (Basel). 2018;7(2):16.

Deyle et al., "Phage Selection of Cyclic Peptides for Application in Research and Drug Development," Accounts of Chemical Research, 2017, vol. 50(8), pp. 1866-1874.

Harrison et al., "Abstract 5144: BT1718, a novel bicyclic peptide-maytansinoid conjugate targeting MT1-MMP for the treatment of solid tumors: Design of bicyclic peptide and linker selection," Cancer Res. 2017;77(13):5144.

Heinis et al., "Phage-encoded combinatorial chemical libraries based on bicyclic peptides," Nat Chem Biol. Jul. 2009;5(7):502-7.

Mitra et al., "Structure-Activity Relationship Analysis of Peptides Targeting the EphA2 Receptor," Biochemistry. 2010;49(31):6687-95.

PCT International Search Report and Written Opinion for PCT/GB2018/05367 dated Mar. 20, 2018.

(56) References Cited

OTHER PUBLICATIONS

PCT International Search Report for PCT Application No. PCT/EP2019/065993, mailed by the European Patent Office dated Sep. 24, 2019, 5 Pages.
Shi et al., "One-Bead-Two-Compound Thioether Bridged Macrocyclic [gamma]-AApeptide Screening Library Against EphA2," J. Med. Chem. 2017;60(22):9290-9298.
Wu et al., "Design and Characterization of Novel EphA2 Agonists for Targeted Delivery of Chemotherapy to Cancer Cells," Chem. Biol. 2015;22(7):876-887.
Mudd et al., "Identification and Optimization of EphA2-Selective Biccyles for the Delivery of Cytotoxic Payloads," J Med Chem. 2020; 63(8) 4107-4116.
PCT International Search Report for PCT Application No. PCT/GB2020/051829, mailed by the European Patent Office dated Oct. 30, 2020, 5 Pages.

* cited by examiner

SEQUENCE LISTING

```
Sequence total quantity: 6
SEQ ID NO: 1             moltype = AA  length = 15
FEATURE                  Location/Qualifiers
REGION                   1..15
                         note = Synthetic Peptide
SITE                     2
                         note = Xaa - X represents HyP
SITE                     12
                         note = Xaa - Xaa represents D-Asp
SITE                     14
                         note = Xaa - Xaa represents HArg
source                   1..15
                         mol_type = protein
                         organism = synthetic construct
SEQUENCE: 1
CXLVNPLCLH PXWXC                                                      15

SEQ ID NO: 2             moltype = AA  length = 20
FEATURE                  Location/Qualifiers
REGION                   1..20
                         note = Synthetic Peptide
SITE                     1
                         note = Xaa - Xaa represents Beta-Ala
SITE                     2
                         note = Xaa - Xaa represents Sar10
SITE                     4
                         note = Xaa - Xaa represents HArg
SITE                     7
                         note = Xaa - Xaa represents HyP
SITE                     17
                         note = Xaa - Xaa represents D-Asp
SITE                     19
                         note = Xaa - Xaa represents HArg
source                   1..20
                         mol_type = protein
                         organism = synthetic construct
SEQUENCE: 2
XXAXDCXLVN PLCLHPXWXC                                                 20

SEQ ID NO: 3             moltype = AA  length = 7
```

```
FEATURE                 Location/Qualifiers
REGION                  1..7
                        note = Synthetic Linker
SITE                    3
                        note = Xaa - Xaa represents Cit
SITE                    5
                        note = Xaa - Xaa represents hPhe
source                  1..7
                        mol_type = protein
                        organism = synthetic construct
SEQUENCE: 3
EPXGXYL                                                                        7

SEQ ID NO: 4            moltype = AA  length = 20
FEATURE                 Location/Qualifiers
REGION                  1..20
                        note = Synthetic Peptide
SITE                    1
                        note = Xaa - Xaa represents Fl
SITE                    3
                        note = Xaa - Xaa represents Sar5
source                  1..20
                        mol_type = protein
                        organism = synthetic construct
SEQUENCE: 4
XGXACPWGPA WCPVNRPGCA                                                         20

SEQ ID NO: 5            moltype = AA  length = 20
FEATURE                 Location/Qualifiers
REGION                  1..20
                        note = Synthetic Peptide
SITE                    1
                        note = Xaa - Xaa represents Fl
SITE                    3
                        note = Xaa - Xaa represents Sar5
source                  1..20
                        mol_type = protein
                        organism = synthetic construct
SEQUENCE: 5
XGXACPWGPF WCPVNRPGCA                                                         20

SEQ ID NO: 6            moltype = AA  length = 23
FEATURE                 Location/Qualifiers
REGION                  1..23
                        note = Synthetic Peptide
SITE                    1
                        note = Xaa - Xaa represents Fl
SITE                    3
                        note = Xaa - Xaa represents Sar5
source                  1..23
                        mol_type = protein
                        organism = synthetic construct
SEQUENCE: 6
XGXADVTCPW GPFWCPVNRP GCA                                                     23
```

METHODS OF SUPPRESSION AND TREATMENT OF DISEASE COMPRISING ADMINISTERING BICYCLE PEPTIDE LIGANDS SPECIFIC FOR EPHA2

CROSS-REFERENCE TO RELATED APPLICATIONS

This application is a divisional of Ser. No. 16/220,685, filed Dec. 14, 2018, which claims the benefit of GB Application No. 1721259.8, filed Dec. 19, 2017, GB Application No. 1804102.0, filed Mar. 14, 2018, and GB Application No. 1818603.1, filed Nov. 14, 2018, the entirety of each of which is hereby incorporated by reference.

SEQUENCE LISTING

The instant application contains a Sequence Listing which has been submitted electronically in XML format and is hereby incorporated by reference in its entirety. Said XML copy, created on Sep. 22, 2022, is named Bicycle_193449_SL.xml and is 14,754 bytes in size.

FIELD OF THE INVENTION

The present invention relates to polypeptides which are covalently bound to non-aromatic molecular scaffolds such that two or more peptide loops are subtended between attachment points to the scaffold. In particular, the invention describes peptides which are high affinity binders of the Eph receptor tyrosine kinase A2 (EphA2). The invention also includes drug conjugates comprising said peptides, conjugated to one or more effector and/or functional groups, to pharmaceutical compositions comprising said peptide ligands and drug conjugates and to the use of said peptide ligands and drug conjugates in preventing, suppressing or treating a disease or disorder characterised by overexpression of EphA2 in diseased tissue (such as a tumour).

BACKGROUND OF THE INVENTION

Cyclic peptides are able to bind with high affinity and target specificity to protein targets and hence are an attractive molecule class for the development of therapeutics. In fact, several cyclic peptides are already successfully used in the clinic, as for example the antibacterial peptide vancomycin, the immunosuppressant drug cyclosporine or the anti-cancer drug octreotide (Driggers et al. (2008), Nat Rev Drug Discov 7 (7), 608-24). Good binding properties result from a relatively large interaction surface formed between the peptide and the target as well as the reduced conformational flexibility of the cyclic structures. Typically, macrocycles bind to surfaces of several hundred square angstrom, as for example the cyclic peptide CXCR4 antagonist CVX15 (400 Å$^2$; Wu et al. (2007), Science 330, 1066-71), a cyclic peptide with the Arg-Gly-Asp motif binding to integrin aVb3 (355 Å$^2$) (Xiong et al. (2002), Science 296 (5565), 151-5) or the cyclic peptide inhibitor upain-1 binding to urokinase-type plasminogen activator (603 Å$^2$; Zhao et al. (2007), J Struct Biol 160 (1), 1-10).

Due to their cyclic configuration, peptide macrocycles are less flexible than linear peptides, leading to a smaller loss of entropy upon binding to targets and resulting in a higher binding affinity. The reduced flexibility also leads to locking target-specific conformations, increasing binding specificity compared to linear peptides. This effect has been exemplified by a potent and selective inhibitor of matrix metalloproteinase 8, (MMP-8) which lost its selectivity over other MMPs when its ring was opened (Cherney et al. (1998), J Med Chem 41 (11), 1749-51). The favorable binding properties achieved through macrocyclization are even more pronounced in multicyclic peptides having more than one peptide ring as for example in vancomycin, nisin and actinomycin.

Different research teams have previously tethered polypeptides with cysteine residues to a synthetic molecular structure (Kemp and McNamara (1985), J. Org. Chem; Timmerman et al. (2005), ChemBioChem). Meloen and co-workers had used tris(bromomethyl)benzene and related molecules for rapid and quantitative cyclisation of multiple peptide loops onto synthetic scaffolds for structural mimicry of protein surfaces (Timmerman et al. (2005), ChemBioChem). Methods for the generation of candidate drug compounds wherein said compounds are generated by linking cysteine containing polypeptides to a molecular scaffold as for example TATA (1,1',1"-(1,3,5-triazinane-1,3,5-triyhtriprop-2-en-1-one, Heinis et al. Angew Chem, Int Ed. 2014; 53:1602-1606).

Phage display-based combinatorial approaches have been developed to generate and screen large libraries of bicyclic peptides to targets of interest (Heinis et al. (2009), Nat Chem Biol 5 (7), 502-7 and WO 2009/098450). Briefly, combinatorial libraries of linear peptides containing three cysteine residues and two regions of six random amino acids (Cys-(Xaa)$_6$-Cys-(Xaa)$_6$-Cys) were displayed on phage and cyclised by covalently linking the cysteine side chains to a small molecule scaffold.

SUMMARY OF THE INVENTION

According to a first aspect of the invention, there is provided a peptide ligand specific for EphA2 comprising a polypeptide comprising at least three cysteine residues, separated by at least two loop sequences, and a non-aromatic molecular scaffold which forms covalent bonds with the cysteine residues of the polypeptide such that at least two polypeptide loops are formed on the molecular scaffold, wherein the peptide ligand comprises the amino acid sequence:

$C_i$(HyP)LVNPLC$_{ii}$LHP(D-Asp)W(HArg)C$_{iii}$ (SEQ ID NO: 1);

wherein HyP is hydroxyproline, HArg is homoarginine and $C_i$, $C_{ii}$ and $C_{iii}$ represent first, second and third cysteine residues, respectively or a pharmaceutically acceptable salt thereof.

According to a further aspect of the invention, there is provided a drug conjugate comprising a peptide ligand as defined herein conjugated to one or more effector and/or functional groups.

According to a further aspect of the invention, there is provided a pharmaceutical composition comprising a peptide ligand or a drug conjugate as defined herein in combination with one or more pharmaceutically acceptable excipients.

According to a further aspect of the invention, there is provided a peptide ligand or drug conjugate as defined herein for use in preventing, suppressing or treating a disease or disorder characterised by overexpression of EphA2 in diseased tissue (such as a tumour).

Figure 1:
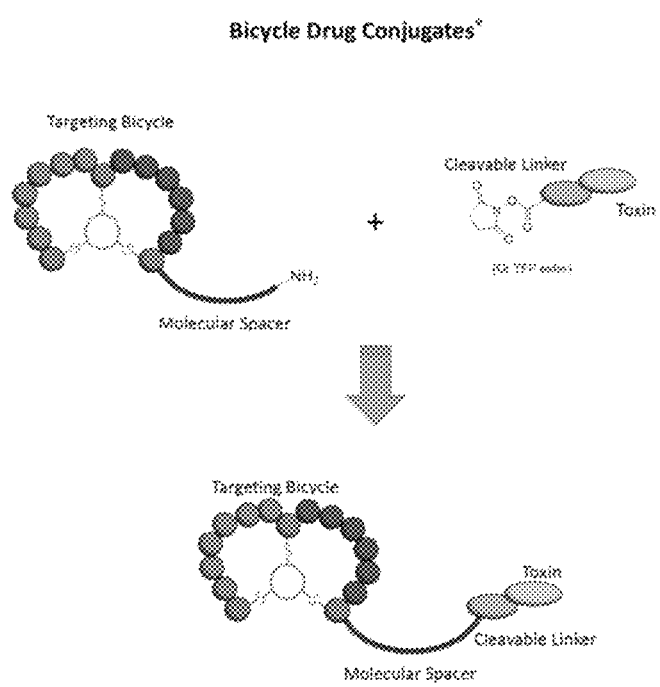
FIG. 1: General schematic demonstrating the concept of preparing Bicycle drug conjugates (BDCs).

Where error bars are present in the above Figures, these represent standard error of the mean (SEM).

DETAILED DESCRIPTION OF THE INVENTION

In one embodiment, the peptide ligand comprises the amino acid sequence:

(SEQ ID NO: 2)
(β-Ala)-Sar$_{10}$-A(HArg)D-C$_i$(HyP)LVNPLC$_{ii}$LHP(D-Asp)W
(HArg)C$_{iii}$ (BCY6099);

wherein Sar is sarcosine, HArg is homoarginine and HyP is hydroxyproline.

In one embodiment, the molecular scaffold is 1,1',1"-(1,3,5-triazinane-1,3,5-triyl)triprop-2-en-1-one (TATA).

In a further embodiment, the molecular scaffold is 1,1',1"-(1,3,5-triazinane-1,3,5-triyl)triprop-2-en-1-one (TATA) and the peptide ligand comprises the amino acid sequence:

(SEQ ID NO: 2)
(β-Ala)-Sar$_{10}$-A(HArg)D-C$_i$(HyP)LVNPLC$_{ii}$LHP(D-Asp)W
(HArg)C$_{iii}$ (BCY6099);

and wherein Sar is sarcosine, HArg is homoarginine and HyP is hydroxyproline.

Unless defined otherwise, all technical and scientific terms used herein have the same meaning as commonly understood by those of ordinary skill in the art, such as in the arts of peptide chemistry, cell culture and phage display, nucleic acid chemistry and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, NY; Ausubel et al., Short Protocols in Molecular Biology (1999) 4$^{th}$ ed., John Wiley & Sons, Inc.), which are incorporated herein by reference.

NOMENCLATURE

Numbering

When referring to amino acid residue positions within the peptides of the invention, cysteine residues ($C_i$, $C_{ii}$ and $C_{iii}$) are omitted from the numbering as they are invariant, therefore, the numbering of amino acid residues within the peptides of the invention is referred to as below:

(SEQ ID NO: 1)
-$C_i$-HyP$_1$-L$_2$-V$_3$-N$_4$-P$_5$-L$_6$-$C_{ii}$-L$_7$-H$_8$-P$_9$-(D-Asp)$_{10}$-W$_{11}$-(HArg)$_{12}$-$C_{iii}$-.

For the purpose of this description, all bicyclic peptides are assumed to be cyclised with 1,1',1''-(1,3,5-triazinane-1,3,5-triyhtriprop-2-en-1-one (TATA) yielding a tri-substituted 1,1',1''-(1,3,5-triazinane-1,3,5-triyhtripropan-1-one structure. Cyclisation with TATA occurs on $C_i$, $C_{ii}$ and $C_{iii}$.

Molecular Format

N- or C-terminal extensions to the bicycle core sequence are added to the left or right side of the sequence, separated by a hyphen. For example, an N-terminal ((3-Ala)-Sarco-Ala tail would be denoted as:

(SEQ ID NO: X)
(β-Ala)-Sar$_{10}$-A-.

Inversed Peptide Sequences

In light of the disclosure in Nair et al (2003) J Immunol 170(3), 1362-1373, it is envisaged that the peptide sequences disclosed herein would also find utility in their retro-inverso form. For example, the sequence is reversed (i.e. N-terminus becomes C-terminus and vice versa) and their stereochemistry is likewise also reversed (i.e. D-amino acids become L-amino acids and vice versa).

Peptide Ligands

A peptide ligand, as referred to herein, refers to a peptide, peptidic or peptidomimetic covalently bound to a molecular scaffold. Typically, such peptides, peptidics or peptidomimetics comprise a peptide having natural or non-natural amino acids, two or more reactive groups (i.e. cysteine residues) which are capable of forming covalent bonds to the scaffold, and a sequence subtended between said reactive groups which is referred to as the loop sequence, since it forms a loop when the peptide, peptidic or peptidomimetic is bound to the scaffold. In the present case, the peptides, peptidics or peptidomimetics comprise at least three cysteine residues (referred to herein as $C_i$, $C_{ii}$ and $C_{iii}$), and form at least two loops on the scaffold.

Advantages of the Peptide Ligands

Certain bicyclic peptides of the present invention have a number of advantageous properties which enable them to be considered as suitable drug-like molecules for injection, inhalation, nasal, ocular, oral or topical administration. Such advantageous properties include:

Species cross-reactivity. This is a typical requirement for preclinical pharmacodynamics and pharmacokinetic evaluation;

Protease stability. Bicyclic peptide ligands should in most circumstances demonstrate stability to plasma proteases, epithelial ("membrane-anchored") proteases, gastric and intestinal proteases, lung surface proteases, intracellular proteases and the like. Protease stability should be maintained between different species such that a bicyclic peptide lead candidate can be developed in animal models as well as administered with confidence to humans;

Desirable solubility profile. This is a function of the proportion of charged and hydrophilic versus hydrophobic residues and intra/inter-molecular H-bonding, which is important for formulation and absorption purposes;

An optimal plasma half-life in the circulation. Depending upon the clinical indication and treatment regimen, it may be required to develop a bicyclic peptide with short or prolonged in vivo exposure times for the management of either chronic or acute disease states. The optimal exposure time will be governed by the requirement for sustained exposure (for maximal therapeutic efficiency) versus the requirement for short exposure times to minimise toxicological effects arising from sustained exposure to the agent.

Selectivity. Certain peptide ligands of the invention demonstrate good selectivity over other Eph receptor tyrosine kinases, such as EphA1, EphA3, EphA4, EphA5, EphA6, EphA7, EphB1, factor XIIA, carbonic anhydrase 9 and CD38 (selectivity data for selected peptide ligands of the invention may be seen in Tables 11 and 12). It should also be noted that selected peptide ligands of the invention exhibit cross reactivity with other species (e.g. mouse and rat) to permit testing in animal models (Tables 3, 7-8, 10 and 12); and Safety. Bleeding events have been reported in pre-clinical in vivo models and clinical trials with EphA2 Antibody Drug Conjugates. For example, a phase 1, open-label study with MEDI-547 was halted due to bleeding and coagulation events that occurred in 5 of 6 patients (Annunziata et al, Invest New Drugs (2013) 31:77-84). The bleeding events observed in patients were consistent with effects on the coagulation system observed in rat and monkey pre-clinical studies: increased activated partial thromboplastin time and increased fibrinogen/fibrin degradation product (Annunziata et al IBID). Overt bleeding events were reportedly seen in toxicology studies in monkeys (Annunziata et al, IBID). Taken together these results imply that MEDI-547 causes Disseminated Intravascular Coagulation (DIC) in both preclinical species and patients. The BDCs reported here have short in vivo half lives (<30 minutes) and are therefore intrinsically less likely to give rise to DIC in patients. Results shown here (see BIOLOGICAL DATA sections 5 and 6 and Table 15) demonstrate that selected Bicycle Drug Conjugates of the invention have no effect on coagulation parameters and gave rise to no bleeding events in pre-clinical studies.

Pharmaceutically Acceptable Salts

It will be appreciated that salt forms are within the scope of this invention, and references to peptide ligands include the salt forms of said ligands.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two.

Acid addition salts (mono- or di-salts) may be formed with a wide variety of acids, both inorganic and organic.

Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, sulfuric, methanesulfonic (mesylate), ethanesulfonic, naphthalenesulfonic, valeric, propanoic, butanoic, malonic, glucuronic and lactobionic acids. One particular salt is the hydrochloride salt. Another particular salt is the acetate salt.

If the compound is anionic, or has a functional group which may be anionic (e.g., —COOH may be —COO⁻), then a salt may be formed with an organic or inorganic base, generating a suitable cation. Examples of suitable inorganic cations include, but are not limited to, alkali metal ions such as $Li^+$, $Na^+$ and $K^+$, alkaline earth metal cations such as $Ca^{2+}$ and $Mg^{2+}$, and other cations such as $Al^{3+}$ or $Zn^+$. Examples of suitable organic cations include, but are not limited to, ammonium ion (i.e. $NH_4^+$) and substituted ammonium ions (e.g., $NH_3R^+$, $NH_2R_2^+$, $NHR_3^+$, $NR_4^+$). Examples of some suitable substituted ammonium ions are those derived from: methylamine, ethylamine, diethylamine, propylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the peptides of the invention contain an amine function, these may form quaternary ammonium salts, for example by reaction with an alkylating agent according to methods well known to the skilled person. Such quaternary ammonium compounds are within the scope of the peptides of the invention.

Isotopic Variations

The present invention includes all pharmaceutically acceptable (radio)isotope-labeled peptide ligands of the invention, wherein one or more atoms are replaced by atoms having the same atomic number, but an atomic mass or mass number different from the atomic mass or mass number usually found in nature, and peptide ligands of the invention, wherein metal chelating groups are attached (termed "effector") that are capable of holding relevant (radio)isotopes, and peptide ligands of the invention, wherein certain functional groups are covalently replaced with relevant (radio) isotopes or isotopically labelled functional groups.

Examples of isotopes suitable for inclusion in the peptide ligands of the invention comprise isotopes of hydrogen, such as $^2H$ (D) and $^3H$ (T), carbon, such as $^{11}C$, $^{13}C$ and $^{14}C$, chlorine, such as $^{36}Cl$, fluorine, such as $^{18}F$, iodine, such as $^{123}I$, $^{125}I$ and $^{131}I$, nitrogen, such as $^{13}N$ and $^{15}N$, oxygen, such as $^{15}O$, $^{17}O$ and $^{18}O$, phosphorus, such as $^{32}P$, sulfur, such as $^{35}S$, copper, such as $^{64}Cu$, gallium, such as $^{67}Ga$ or $^{68}Ga$, yttrium, such as $^{90}Y$ and lutetium, such as $^{177}Lu$, and Bismuth, such as $^{213}Bi$.

Certain isotopically-labelled peptide ligands of the invention, for example, those incorporating a radioactive isotope, are useful in drug and/or substrate tissue distribution studies, and to clinically assess the presence and/or absence of the EphA2 target on diseased tissues. The peptide ligands of the invention can further have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^3H$ (T), and carbon-14, i.e. $^{14}C$, are particularly useful for this purpose in view of their ease of incorporation and ready means of detection.

Substitution with heavier isotopes such as deuterium, i.e. $^2H$ (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining target occupancy.

Isotopically-labeled compounds of peptide ligands of the invention can generally be prepared by conventional techniques known to those skilled in the art or by processes analogous to those described in the accompanying Examples using an appropriate isotopically-labeled reagent in place of the non-labeled reagent previously employed.

Non-Aromatic Molecular Scaffold

References herein to the term "non-aromatic molecular scaffold" refer to any molecular scaffold as defined herein which does not contain an aromatic (i.e. unsaturated) carbocyclic or heterocyclic ring system.

Suitable examples of non-aromatic molecular scaffolds are described in Heinis et al (2014) Angewandte Chemie, International Edition 53(6) 1602-1606.

As noted in the foregoing documents, the molecular scaffold may be a small molecule, such as a small organic molecule.

In one embodiment the molecular scaffold may be a macromolecule. In one embodiment the molecular scaffold is a macromolecule composed of amino acids, nucleotides or carbohydrates.

In one embodiment the molecular scaffold comprises reactive groups that are capable of reacting with functional group(s) of the polypeptide to form covalent bonds.

The molecular scaffold may comprise chemical groups which form the linkage with a peptide, such as amines, thiols, alcohols, ketones, aldehydes, nitriles, carboxylic acids, esters, alkenes, alkynes, azides, anhydrides, succinimides, maleimides, alkyl halides and acyl halides.

An example of an a unsaturated carbonyl containing compound is 1,1',1''-(1,3,5-triazinane-1,3,5-triyl)triprop-2-en-1-one (TATA) (Angewandte Chemie, International Edition (2014), 53(6), 1602-1606).

Effector and Functional Groups

According to a further aspect of the invention, there is provided a drug conjugate comprising a peptide ligand as defined herein conjugated to one or more effector and/or functional groups.

Effector and/or functional groups can be attached, for example, to the N and/or C termini of the polypeptide, to an amino acid within the polypeptide, or to the molecular scaffold.

Appropriate effector groups include antibodies and parts or fragments thereof. For instance, an effector group can include an antibody light chain constant region (CL), an antibody CH1 heavy chain domain, an antibody CH2 heavy chain domain, an antibody CH3 heavy chain domain, or any combination thereof, in addition to the one or more constant region domains. An effector group may also comprise a hinge region of an antibody (such a region normally being found between the CH1 and CH2 domains of an IgG molecule).

In a further embodiment of this aspect of the invention, an effector group according to the present invention is an Fc region of an IgG molecule. Advantageously, a peptide ligand-effector group according to the present invention comprises or consists of a peptide ligand Fc fusion having a tβ half-life of a day or more, two days or more, 3 days or more, 4 days or more, 5 days or more, 6 days or more or 7 days or more. Most advantageously, the peptide ligand according to the present invention comprises or consists of a peptide ligand Fc fusion having a tβ half-life of a day or more.

Functional groups include, in general, binding groups, drugs, reactive groups for the attachment of other entities, functional groups which aid uptake of the macrocyclic peptides into cells, and the like.

The ability of peptides to penetrate into cells will allow peptides against intracellular targets to be effective. Targets that can be accessed by peptides with the ability to penetrate into cells include transcription factors, intracellular signalling molecules such as tyrosine kinases and molecules involved in the apoptotic pathway. Functional groups which enable the penetration of cells include peptides or chemical groups which have been added either to the peptide or the molecular scaffold. Peptides such as those derived from such as VP22, HIV-Tat, a homeobox protein of Drosophila (Antennapedia), e.g. as described in Chen and Harrison, Biochemical Society Transactions (2007) Volume 35, part 4, p 821; Gupta et al. in Advanced Drug Discovery Reviews (2004) Volume 57 9637. Examples of short peptides which have been shown to be efficient at translocation through plasma membranes include the 16 amino acid penetratin peptide from Drosophila Antennapedia protein (Derossi et al (1994) J Biol. Chem. Volume 269 p 10444), the 18 amino acid 'model amphipathic peptide' (Oehlke et al (1998) Biochim Biophys Acts Volume 1414 p 127) and arginine rich regions of the HIV TAT protein. Non peptidic approaches include the use of small molecule mimics or SMOCs that can be easily attached to biomolecules (Okuyama et al (2007) Nature Methods Volume 4 p 153). Other chemical strategies to add guanidinium groups to molecules also enhance cell penetration (Elson-Scwab et al (2007) J Biol Chem Volume 282 p 13585). Small molecular weight molecules such as steroids may be added to the molecular scaffold to enhance uptake into cells.

One class of functional groups which may be attached to peptide ligands includes antibodies and binding fragments thereof, such as Fab, Fv or single domain fragments. In particular, antibodies which bind to proteins capable of increasing the half-life of the peptide ligand in vivo may be used.

In one embodiment, a peptide ligand-effector group according to the invention has a tβ half-life selected from the group consisting of: 12 hours or more, 24 hours or more, 2 days or more, 3 days or more, 4 days or more, 5 days or more, 6 days or more, 7 days or more, 8 days or more, 9 days or more, 10 days or more, 11 days or more, 12 days or more, 13 days or more, 14 days or more, 15 days or more or 20 days or more. Advantageously a peptide ligand-effector group or composition according to the invention will have a tβ range 12 to 60 hours. In a further embodiment, it will have a tβ half-life of a day or more. In a further embodiment still, it will be in the range 12 to 26 hours.

In one particular embodiment of the invention, the functional group is selected from a metal chelator, which is suitable for complexing metal radioisotopes of medicinal relevance.

Possible effector groups also include enzymes, for instance such as carboxypeptidase G2 for use in enzyme/prodrug therapy, where the peptide ligand replaces antibodies in ADEPT.

In one particular embodiment of the invention, the functional group is selected from a drug, such as a cytotoxic agent for cancer therapy. Suitable examples include: alkylating agents such as cisplatin and carboplatin, as well as oxaliplatin, mechlorethamine, cyclophosphamide, chlorambucil, ifosfamide; Anti-metabolites including purine analogs azathioprine and mercaptopurine or pyrimidine analogs; plant alkaloids and terpenoids including vinca alkaloids such as Vincristine, Vinblastine, Vinorelbine and Vindesine; Podophyllotoxin and its derivatives etoposide and teniposide; Taxanes, including paclitaxel, originally known as Taxol; topoisomerase inhibitors including camptothecins: irinotecan and topotecan, and type II inhibitors including amsacrine, etoposide, etoposide phosphate, and teniposide. Further agents can include antitumour antibiotics which include the immunosuppressant dactinomycin (which is used in kidney transplantations), doxorubicin, epirubicin, bleomycin, calicheamycins, and others.

In one further particular embodiment of the invention, the cytotoxic agent is selected from maytansinoids (such as DM1) or monomethyl auristatins (such as MMAE).

DM1 is a cytotoxic agent which is a thiol-containing derivative of maytansine and has the following structure:

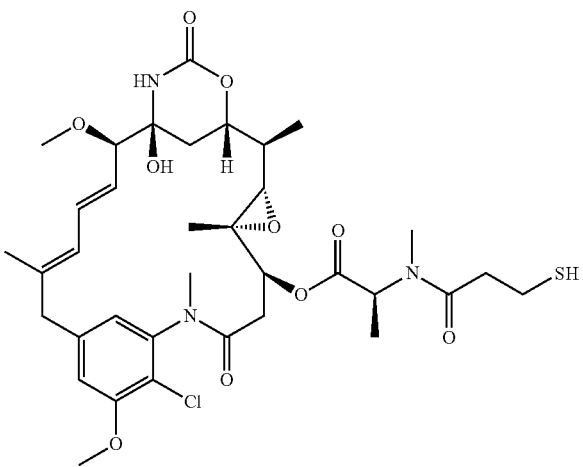

Monomethyl auristatin E (MMAE) is a synthetic antineoplastic agent and has the following structure:

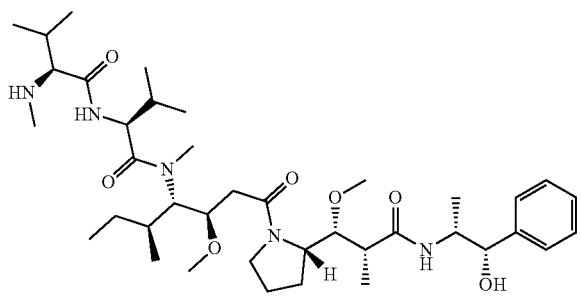 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@@H](NC)C(C)C)C(C)C]

In one embodiment, the cytotoxic agent is linked to the bicyclic peptide by a cleavable bond, such as a disulphide bond or a protease sensitive bond. In a further embodiment, the groups adjacent to the disulphide bond are modified to control the hindrance of the disulphide bond, and by this the rate of cleavage and concomitant release of cytotoxic agent.

Published work established the potential for modifying the susceptibility of the disulphide bond to reduction by introducing steric hindrance on either side of the disulphide bond (Kellogg et al (2011) Bioconjugate Chemistry, 22, 717). A greater degree of steric hindrance reduces the rate of reduction by intracellular glutathione and also extracellular (systemic) reducing agents, consequentially reducing the ease by which toxin is released, both inside and outside the cell. Thus, selection of the optimum in disulphide stability in the circulation (which minimises undesirable side effects of the toxin) versus efficient release in the intracellular milieu (which maximises the therapeutic effect) can be achieved by careful selection of the degree of hindrance on either side of the disulphide bond.

The hindrance on either side of the disulphide bond is modulated through introducing one or more methyl groups on either the targeting entity (here, the bicyclic peptide) or toxin side of the molecular construct.

In one embodiment, the drug conjugate additionally comprises a linker between said peptide ligand and said cytotoxic agents.

In one embodiment, the cytotoxic agent and linker is selected from any combinations of those described in WO 2016/067035 (the cytotoxic agents and linkers thereof are herein incorporated by reference).

In one embodiment the cytotoxic agent is MMAE.

In one embodiment, the linker between said cytotoxic agent and said bicyclic peptide comprises one or more amino acid residues. Thus, in one embodiment, the cytotoxic agent is MMAE and the linker is selected from: -Val-Cit-, -Trp-Cit-, -Val-Lys-, -D-Trp-Cit-, -Ala-Ala-Asn-, D-Ala-Phe-Lys- or -Glu-Pro-Cit-Gly-hPhe-Tyr-Leu- (SEQ ID NO: 3). In a further embodiment, the cytotoxic agent is MMAE and the linker is selected from: -Val-Cit-, -Trp-Cit-, -Val-Lys- or -D-Trp-Cit-. In a yet further embodiment, the cytotoxic agent is MMAE and the linker is -Val-Cit- or -Val-Lys-. In a still yet further embodiment, the cytotoxic agent is MMAE and the linker is -Val-Cit-.

In an alternative embodiment, the linker between said cytoxic agent comprises a disulfide bond, such as a cleavable disulfide bond. Thus, in a further embodiment, the cytotoxic agent is DM1 and the linker is selected from: —S—S—, —SS($SO_3H$)—, —SS-(Me)-, -(Me)-SS-(Me)-, —SS-($Me_2$)- or —SS-(Me)-$SO_3H$—. In a further embodiment, the cytotoxic agent is DM1 and the linker comprises an —S—S— moiety, such as (N-succinimidyl 3-(2-pyridyldithio)propionate (SPDB), or an —SS($SO_3H$)— moiety, such as $SO_3H$-SPDB. In a yet further embodiment, the cytotoxic agent is DM1 and the linker comprises an —S—S— moiety, such as —S—S— or —S—S— ($SO_3H$)—.

In one embodiment, the cytotoxic agent is DM1 and the drug conjugate comprises a compound of formula (A):

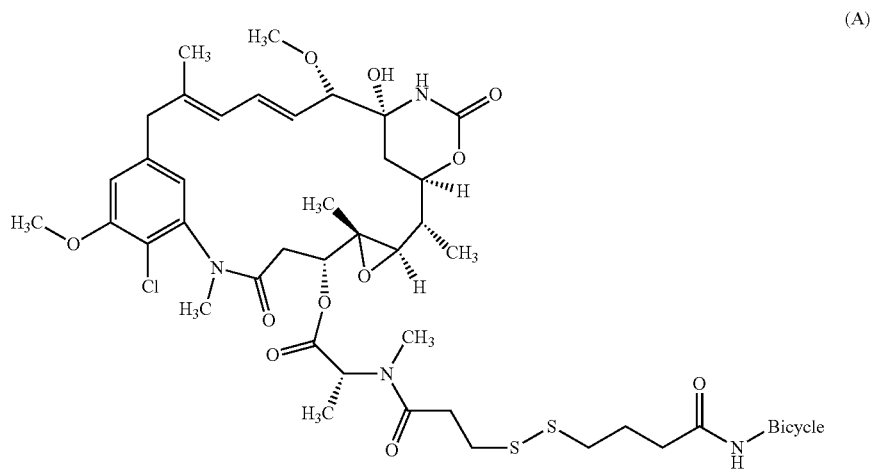

(A)

wherein said bicycle is BCY6099 as defined herein.

In an alternative embodiment, the cytotoxic agent is DM1 and the drug conjugate comprises a compound of formula (B):

(B)

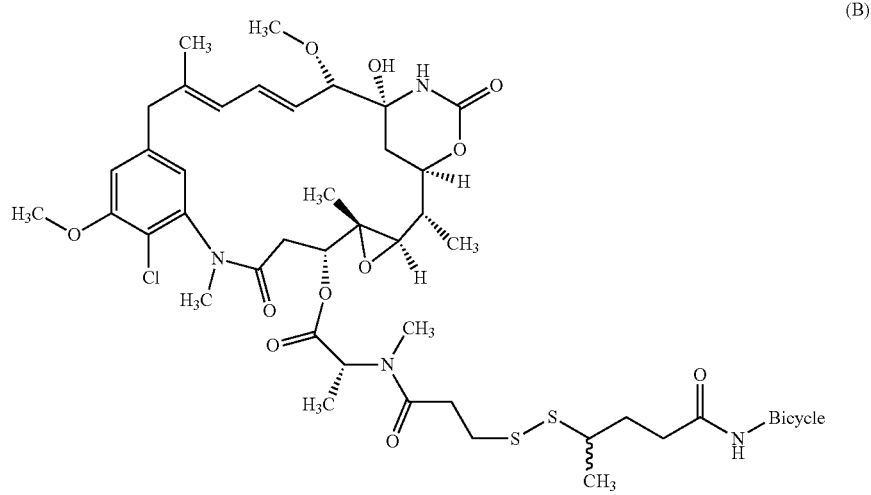

wherein said bicycle is BCY6099 as defined herein.

In an alternative embodiment, the cytotoxic agent is DM1 and the drug conjugate comprises a compound of formula (A), wherein said bicycle is selected from BCY6099 as defined herein. This BDC is known herein as BCY6027. Data is presented herein which demonstrates excellent competition binding for BCY6027 in the EphA2 competition binding assay as shown in Tables 4 and 8.

In an alternative embodiment, the cytotoxic agent is DM1 and the drug conjugate comprises a compound of formula (B), wherein said bicycle is selected from BCY6099 as defined herein. This BDC is known herein as BCY6028. Data is presented herein which demonstrates excellent competition binding for BCY6028 in the EphA2 competition binding assay as shown in Tables 4 and 8.

In a further embodiment, the cytotoxic agent is MMAE or DM1 and the drug conjugate is selected from BCY6136 and BCY6173. Data is presented herein which shows that these two Bicycle Drug Conjugates exhibited no significant binding to: closely related human homologs EphA1, EphA3, EphA4, EphA5, EphA6, EphA7 and EphB4; mouse EphA3 and EphA4; and rat EphA3 and EphB1 as shown in Tables 11 and 12.

In a yet further embodiment, the drug conjugate is selected from any one of: BCY6135, BCY6136, BCY6173, BCY6174 and BCY6175:

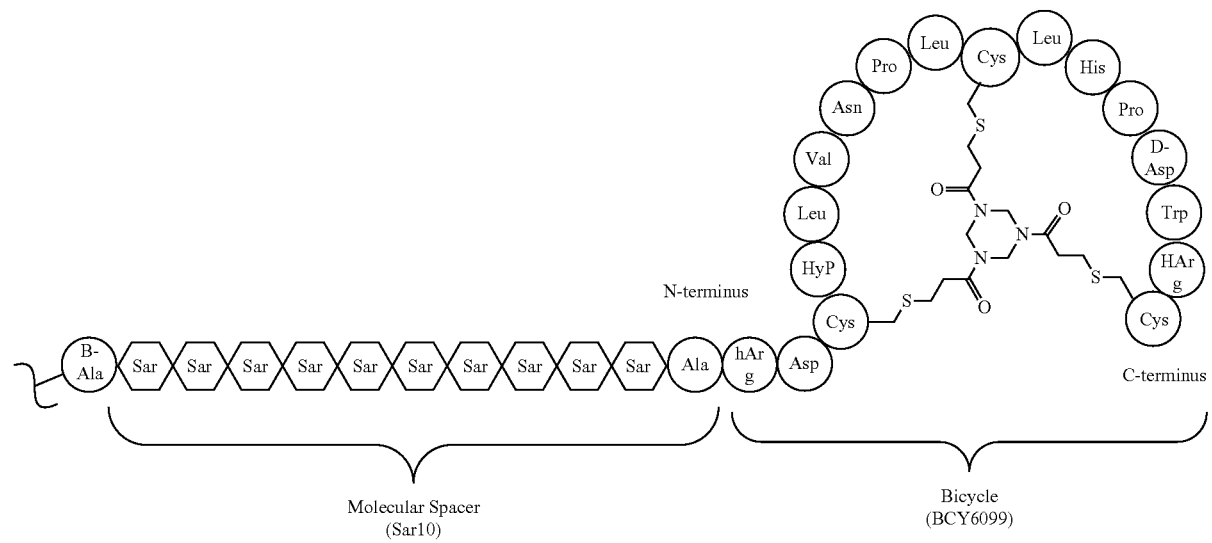

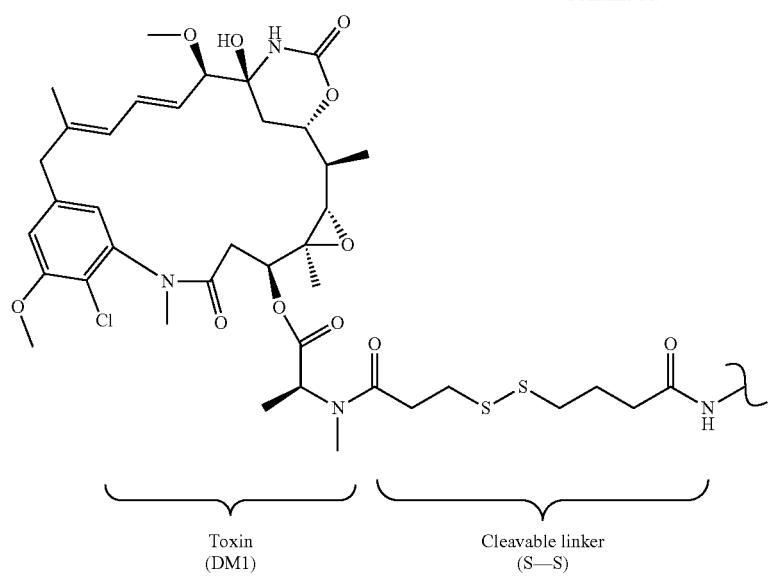
Toxin
(DM1)
Cleavable linker
(S—S)
BCY6135
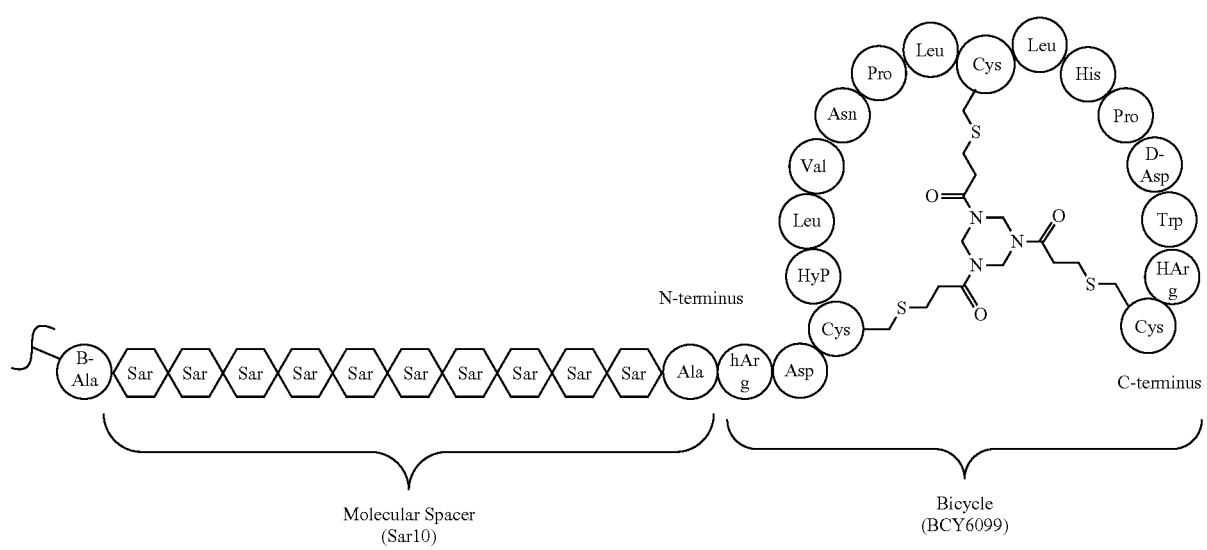
Molecular Spacer
(Sar10)
Bicycle
(BCY6099)
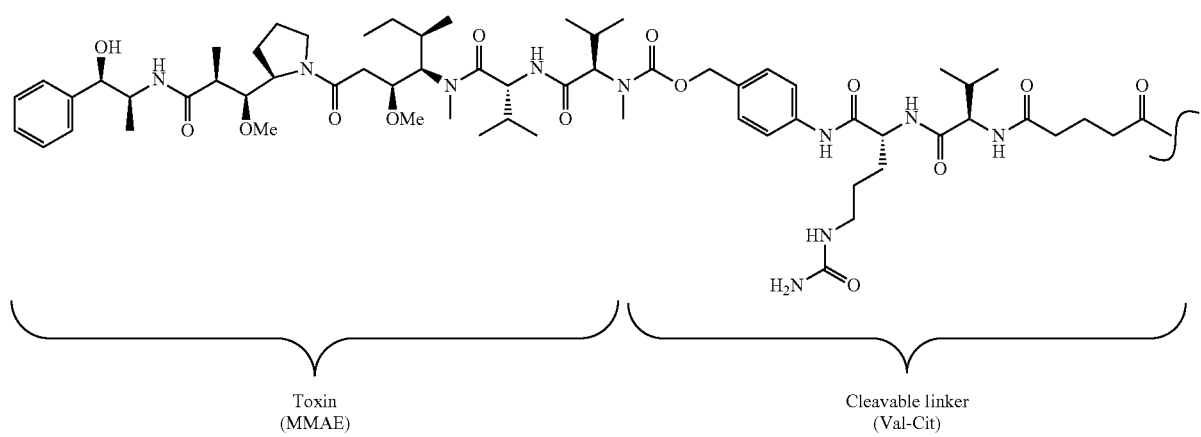
Toxin
(MMAE)
Cleavable linker
(Val-Cit)
BCY6136

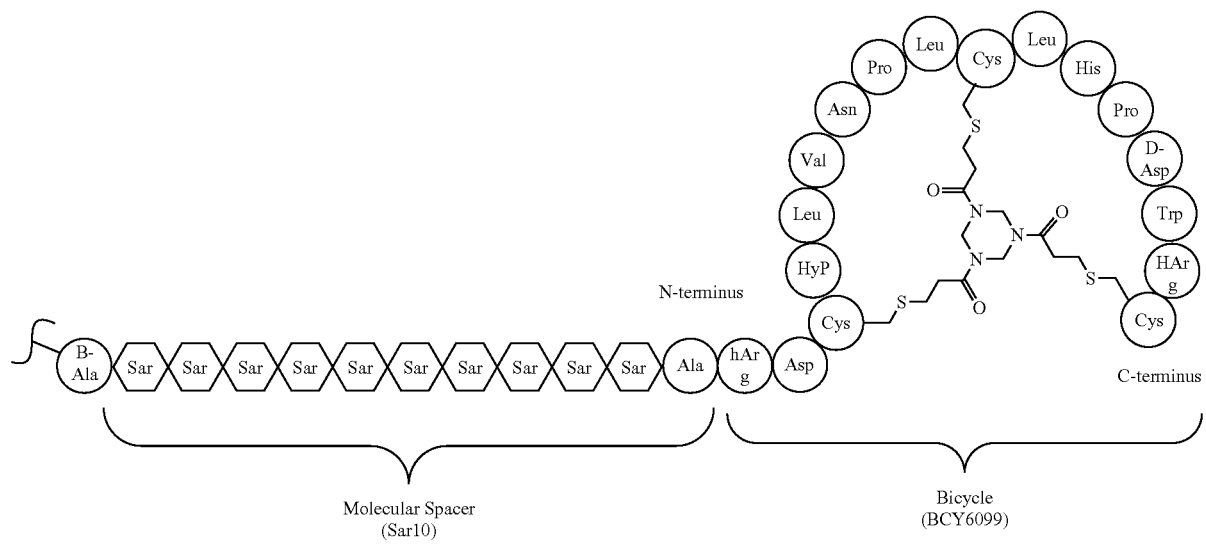
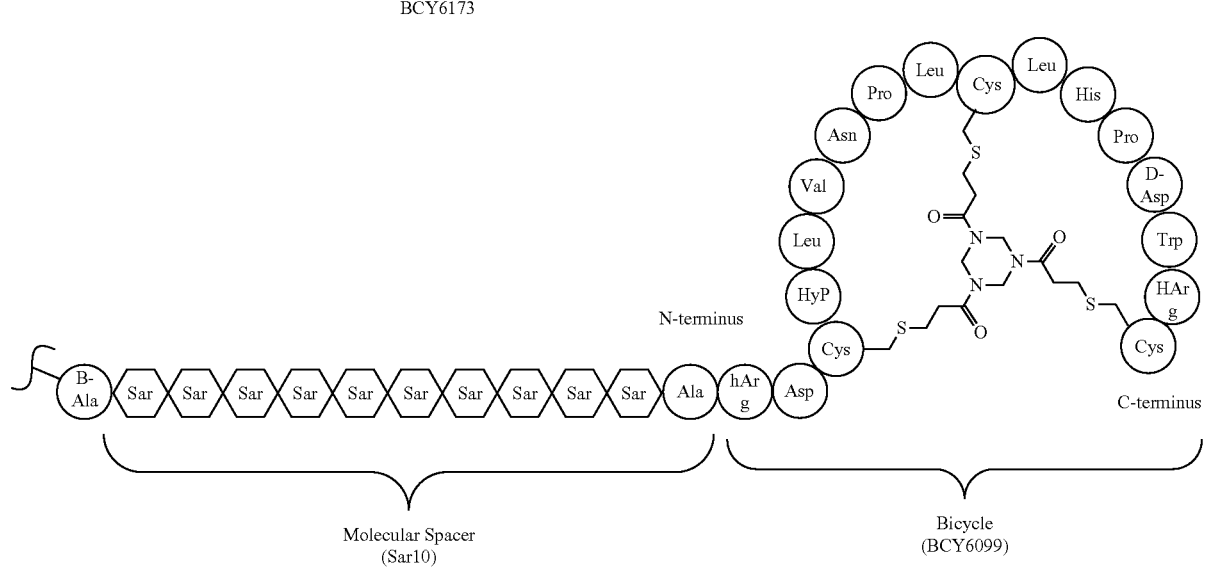

-continued

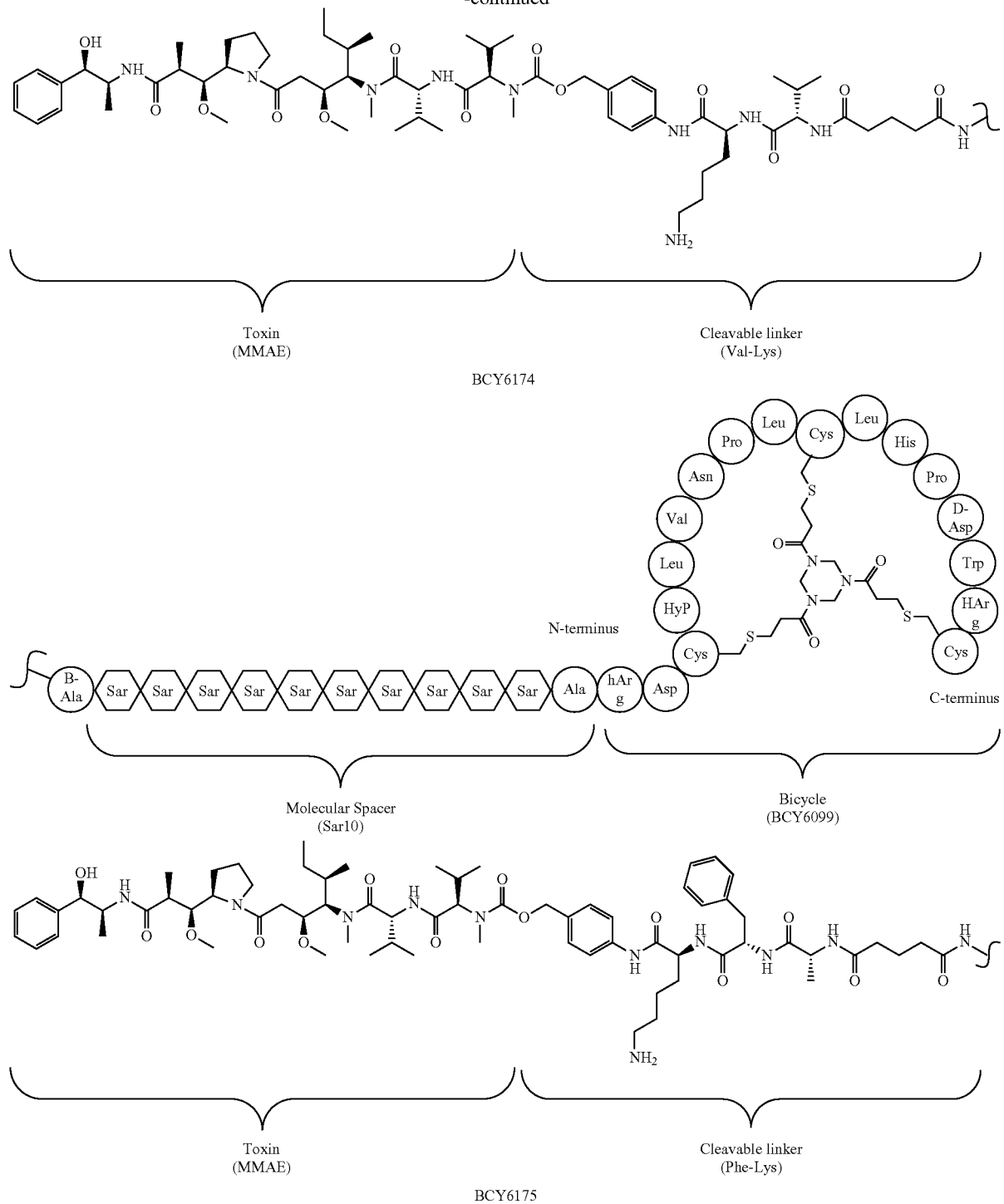

BCY6174

BCY6175

Figure 23:
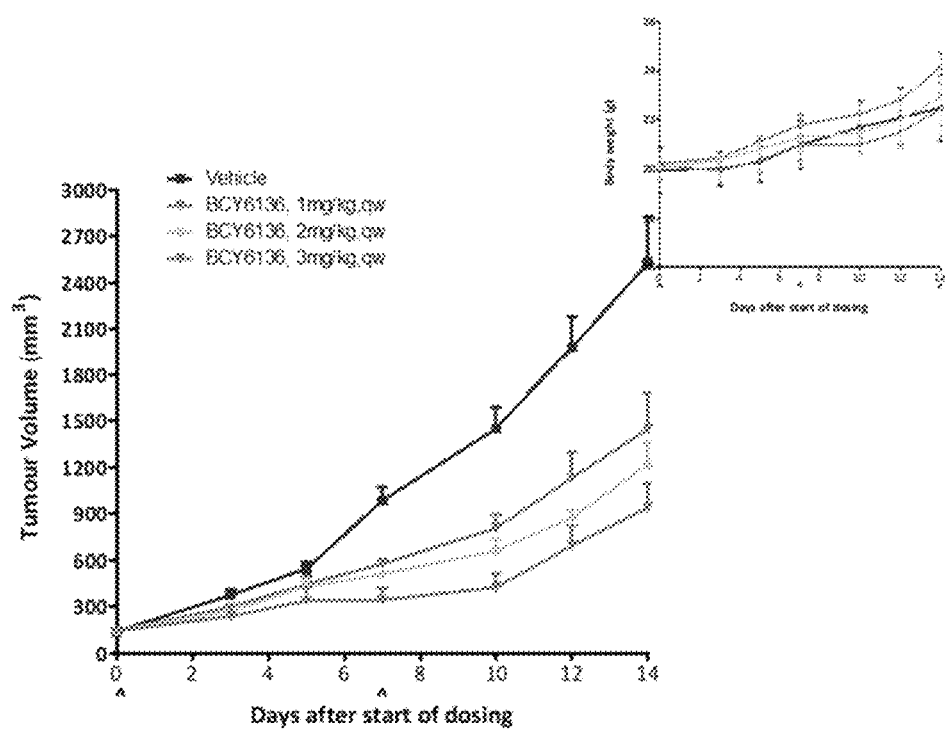
FIG. 23: Body weight changes and tumor volume traces after administering BCY6136 to female CB17-SCID mice bearing MOLP-8 xenograft. Data points represent group mean body weight.
Figure 24:
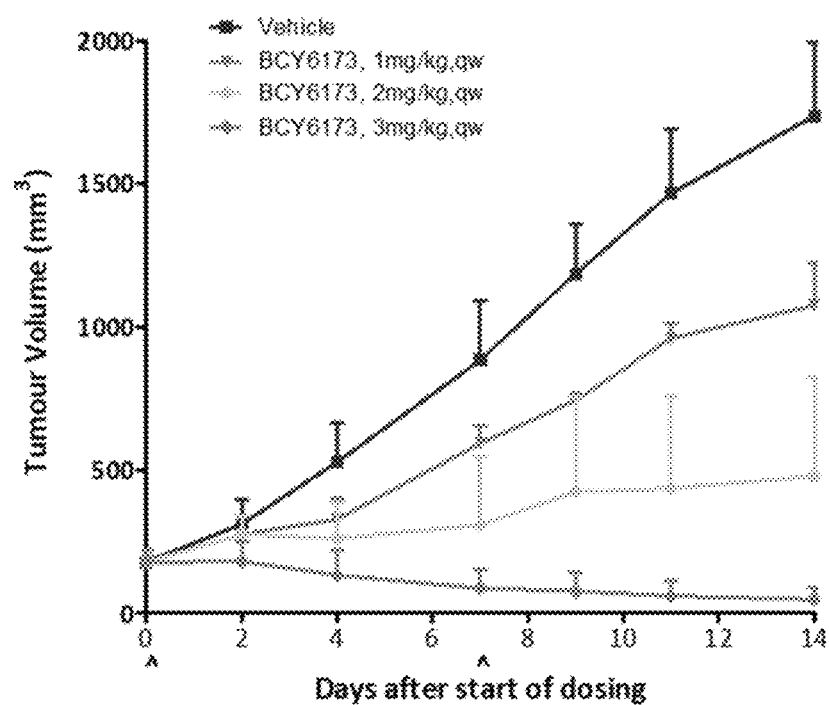
FIGS. 24 to 29: Body weight changes and tumor volume traces after administering BCY6173 (FIG. 24), BCY6135 (FIG. 25), BCY6136 (FIG. 26), BCY6174 (FIG. 27), BCY6175 (FIG. 28) and ADC (FIG. 29) to female BALB/c nude mice bearing HT1080 xenograft. Data points represent group mean body weight.
Figure 25:
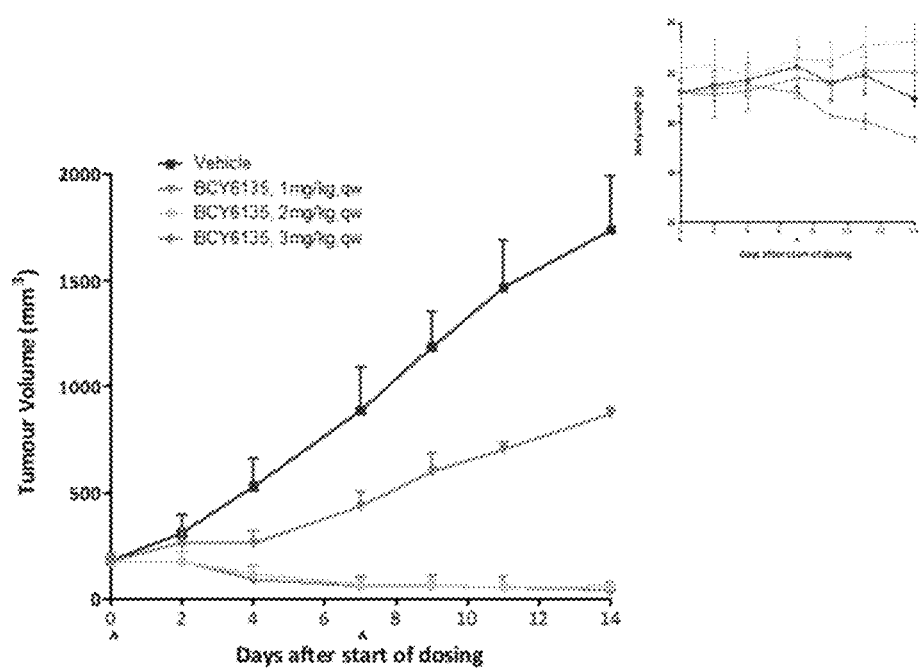
Figure 26:
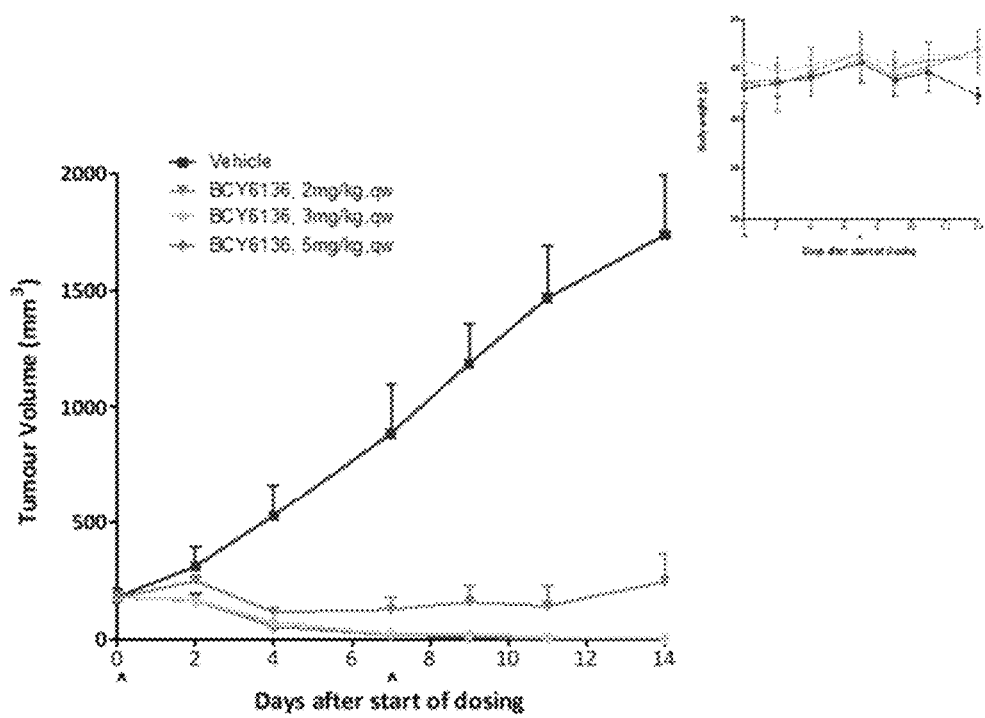
Figure 27:
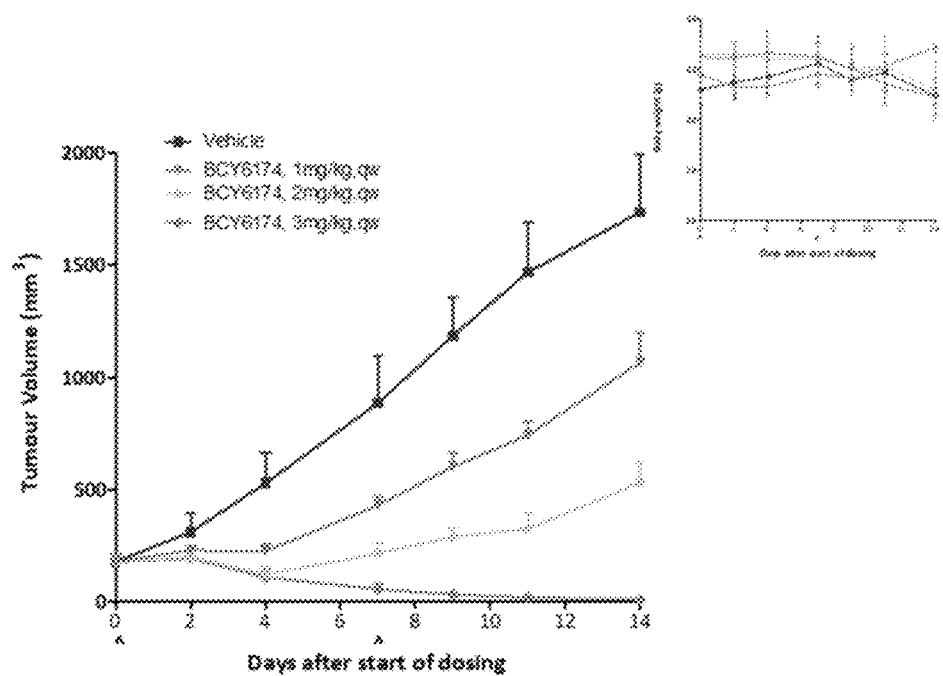
Figure 28:
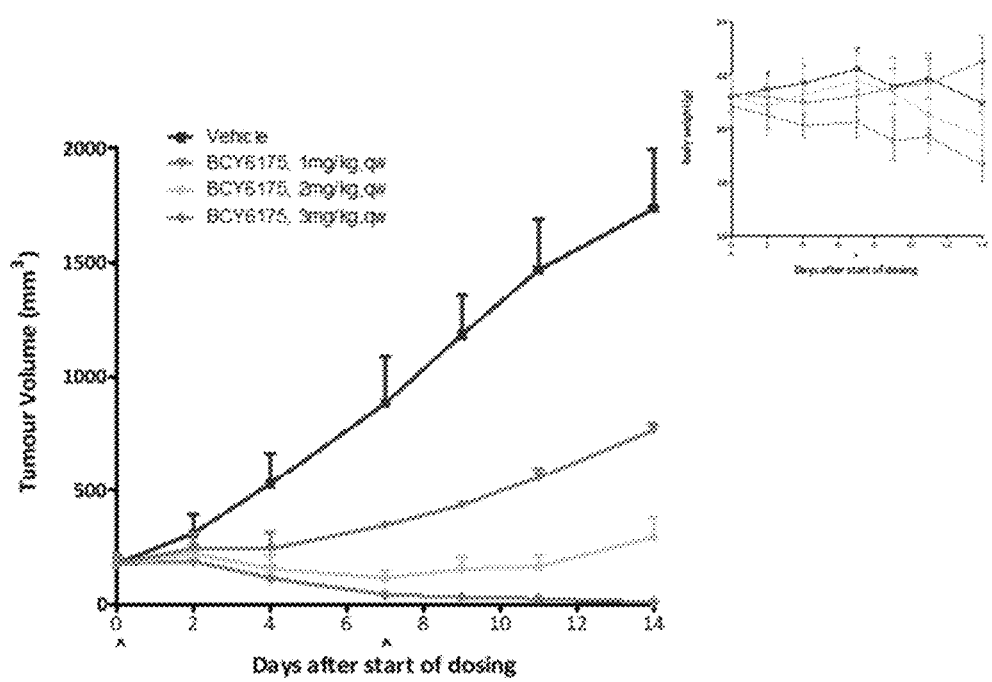
Figure 29:
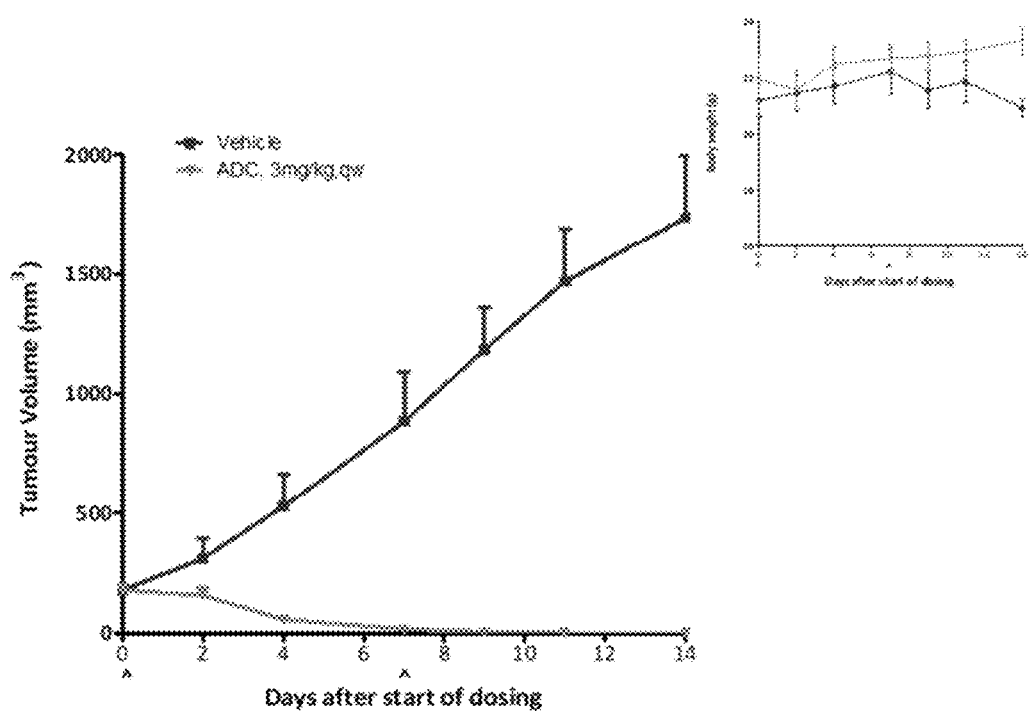

In a still yet further embodiment, the drug conjugate is BCY6136. Data is presented herein in Studies 7 and 8 which show that BCY6136 showed significant and potent anti-tumor activity in the PC-3 xenograft prostate cancer model (see FIGS. 5 and 6 and Tables 16 to 19). Data is also provided herein which show that BCY6136 demonstrated potent antitumor activity in the NCI-H1975 xenograft lung cancer (NSCLC) model (see FIG. 8 and Tables 20 to 25). Data is also presented herein in Studies 10 and 11 which show that BCY6136 demonstrated potent anti-tumor effect in both large and small tumour size LU-01-0251 PDX lung cancer (NSCLC) models (see FIGS. 9 and 10 and Tables 26 to 29) wherein complete tumor regression was observed. Data is also presented herein in Study 12 which show that BCY6136 demonstrated significant anti-tumor effect in the LU-01-0046 PDX lung cancer (NSCLC) model (see FIG. 11 and Tables 30 and 31) wherein complete tumor regression was observed for BCY6136. Data is also presented herein in Study 13 which show that BCY6136 demonstrated dose dependent anti-tumor activity in the LU-01-0046 PDX lung cancer (NSCLC) model (see FIG. 12 and Tables 32 and 33). Data is also presented herein in Study 14 which show BCY6136 eradicated tumors in the LU-01-0046 PDX lung cancer (NSCLC) model (see FIGS. 13 to 15 and Tables 34 to 37). Data is also presented herein in Studies 15 and 16 which demonstrate the effects of BCY6136 in two models which make use of cell lines with low/negligible EphA2 expression (namely Lu-01-0412 and Lu-01-0486). This data is shown in FIGS. 23 and 24 and Tables 38 to 41 and demonstrate that BCY6136 had no effect upon tumor regression in either cell line but BCYs BCY8245 and BCY8781, which bind to a target highly expressed in the Lu-01-0412 cell line, completely eradicated the tumour. Data is presented herein in Study 17 which show that BCY6136 demonstrated potent antitumor activity in the MDA-MB-231 xenograft breast cancer model (see FIG. 18 and Tables 42 to 45). Data is also presented herein in Study 18 which demonstrates the effects of BCY6136 in a breast cancer model which makes use of a cell line with low/negligible EphA2 expression (namely EMT6). This data is shown in FIG. 19 and Tables 46 and 47 and demonstrates that BCY6136 had no effect upon tumor regression in this cell line. Data is also presented herein in Study 19 which show that BCY6136 demonstrated significant antitumor activity in the NCI-N87 xenograft gastric cancer model (see FIG. 20 and Tables 48 and 49). Data is also presented herein in Study 20 which show that BCY6136 demonstrated significant antitumor activity in the SK-OV-3 xenograft ovarian cancer model (see FIG. 21 and Tables 50 and 51) compared with the ADC MEDI-547 which demonstrated moderate antitumour activity. Data is also presented herein in Study 21 which show that BCY6136 demonstrated significant antitumor activity in the OE-21 xenograft oesophageal cancer model (see FIG. 22 and Tables 52 and 53). Data is also presented herein in Study 22 which show that BCY6136 demonstrated dose-dependent antitumor activity in the MOLP-8 xenograft multiple myeloma model (see FIG. 23). Data is also presented herein in Study 23 which show that BCY6136 demonstrated potent antitumor activity in the HT-1080 xenograft fibrosarcoma model (see FIGS. 24 to 28 and Tables 56 and 57).

Synthesis

The peptides of the present invention may be manufactured synthetically by standard techniques followed by reaction with a molecular scaffold in vitro. When this is performed, standard chemistry may be used. This enables the rapid large scale preparation of soluble material for further downstream experiments or validation. Such methods could be accomplished using conventional chemistry such as that disclosed in Timmerman et al (supra).

Thus, the invention also relates to manufacture of polypeptides or conjugates selected as set out herein, wherein the manufacture comprises optional further steps as explained below. In one embodiment, these steps are carried out on the end product polypeptide/conjugate made by chemical synthesis.

Optionally amino acid residues in the polypeptide of interest may be substituted when manufacturing a conjugate or complex.

Peptides can also be extended, to incorporate for example another loop and therefore introduce multiple specificities.

To extend the peptide, it may simply be extended chemically at its N-terminus or C-terminus or within the loops using orthogonally protected lysines (and analogues) using standard solid phase or solution phase chemistry. Standard (bio)conjugation techniques may be used to introduce an activated or activatable N- or C-terminus. Alternatively additions may be made by fragment condensation or native chemical ligation e.g. as described in (Dawson et al. 1994. Synthesis of Proteins by Native Chemical Ligation. Science 266:776-779), or by enzymes, for example using subtiligase as described in (Chang et al Proc Natl Acad Sci USA. 1994 Dec. 20; 91(26):12544-8 or in Hikari et al Bioorganic & Medicinal Chemistry Letters Volume 18, Issue 22, 15 Nov. 2008, Pages 6000-6003).

Alternatively, the peptides may be extended or modified by further conjugation through disulphide bonds. This has the additional advantage of allowing the first and second peptide to dissociate from each other once within the reducing environment of the cell. In this case, the molecular scaffold could be added during the chemical synthesis of the first peptide so as to react with the three cysteine groups; a further cysteine or thiol could then be appended to the N or C-terminus of the first peptide, so that this cysteine or thiol only reacted with a free cysteine or thiol of the second peptide, forming a disulfide-linked bicyclic peptide-peptide conjugate.

Similar techniques apply equally to the synthesis/coupling of two bicyclic and bispecific macrocycles, potentially creating a tetraspecific molecule.

Furthermore, addition of other functional groups or effector groups may be accomplished in the same manner, using appropriate chemistry, coupling at the N- or C-termini or via side chains. In one embodiment, the coupling is conducted in such a manner that it does not block the activity of either entity.

Pharmaceutical Compositions

According to a further aspect of the invention, there is provided a pharmaceutical composition comprising a peptide ligand or a drug conjugate as defined herein in combination with one or more pharmaceutically acceptable excipients.

Generally, the present peptide ligands will be utilised in purified form together with pharmacologically appropriate excipients or carriers. Typically, these excipients or carriers include aqueous or alcoholic/aqueous solutions, emulsions or suspensions, including saline and/or buffered media. Parenteral vehicles include sodium chloride solution, Ringers dextrose, dextrose and sodium chloride and lactated Ringers. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringers dextrose. Preservatives and other additives, such as antimicrobials, antioxidants, chelating agents and inert gases, may also be present (Mack (1982) Remington's Pharmaceutical Sciences, 16th Edition).

The peptide ligands of the present invention may be used as separately administered compositions or in conjunction with other agents. These can include antibodies, antibody fragments and various immunotherapeutic drugs, such as cylcosporine, methotrexate, adriamycin or cisplatinum and immunotoxins. Pharmaceutical compositions can include "cocktails" of various cytotoxic or other agents in conjunction with the protein ligands of the present invention, or even combinations of selected polypeptides according to the present invention having different specificities, such as polypeptides selected using different target ligands, whether or not they are pooled prior to administration.

The route of administration of pharmaceutical compositions according to the invention may be any of those commonly known to those of ordinary skill in the art. For therapy, the peptide ligands of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. Preferably, the pharmaceutical compositions according to the invention will be administered by inhalation. The dosage and frequency of administration will depend on the age, sex and condition of the patient, concurrent administration of other drugs, counterindications and other parameters to be taken into account by the clinician.

The peptide ligands of this invention can be lyophilised for storage and reconstituted in a suitable carrier prior to use. This technique has been shown to be effective and art-known lyophilisation and reconstitution techniques can be employed. It will be appreciated by those skilled in the art that lyophilisation and reconstitution can lead to varying degrees of activity loss and that levels may have to be adjusted upward to compensate.

The compositions containing the present peptide ligands or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 5.0 mg of selected peptide ligand per kilogram of body weight, with doses of 0.05 to 2.0 mg/kg/dose being more commonly used. For prophylactic applications, compositions containing the present peptide ligands or cocktails thereof may also be administered in similar or slightly lower dosages.

A composition containing a peptide ligand according to the present invention may be utilised in prophylactic and therapeutic settings to aid in the alteration, inactivation, killing or removal of a select target cell population in a mammal. In addition, the peptide ligands described herein may be used extracorporeally or in vitro selectively to kill, deplete or otherwise effectively remove a target cell population from a heterogeneous collection of cells. Blood from a mammal may be combined extracorporeally with the selected peptide ligands whereby the undesired cells are killed or otherwise removed from the blood for return to the mammal in accordance with standard techniques.

Therapeutic Uses

The bicyclic peptides of the invention have specific utility as EphA2 binding agents.

Eph receptor tyrosine kinases (Ephs) belong to a large group of receptor tyrosine kinases (RTKs), kinases that phosphorylate proteins on tyrosine residues. Ephs and their membrane bound ephrin ligands (ephrins) control cell positioning and tissue organization (Poliakov et al. (2004) Dev Cell 7, 465-80). Functional and biochemical Eph responses occur at higher ligand oligomerization states (Stein et al. (1998) Genes Dev 12, 667-678).

Among other patterning functions, various Ephs and ephrins have been shown to play a role in vascular development. Knockout of EphB4 and ephrin-B2 results in a lack of the ability to remodel capillary beds into blood vessels (Poliakov et al., supra) and embryonic lethality. Persistent expression of some Eph receptors and ephrins has also been observed in newly-formed, adult micro-vessels (Brantley-Sieders et al. (2004) Curr Pharm Des 10, 3431-42; Adams (2003) J Anat 202, 105-12).

The de-regulated re-emergence of some ephrins and their receptors in adults also has been observed to contribute to tumor invasion, metastasis and neo-angiogenesis (Nakamoto et al. (2002) Microsc Res Tech 59, 58-67; Brantley-Sieders et al., supra). Furthermore, some Eph family members have been found to be over-expressed on tumor cells from a variety of human tumors (Brantley-Sieders et al., supra); Marme (2002) Ann Hematol 81 Suppl 2, S66; Booth et al. (2002) Nat Med 8, 1360-1).

EPH receptor A2 (ephrin type-A receptor 2) is a protein that in humans is encoded by the EPHA2 gene.

EphA2 is upregulated in multiple cancers in man, often correlating with disease progression, metastasis and poor prognosis e.g.: breast (Zelinski et al (2001) Cancer Res. 61, 2301-2306; Zhuang et al (2010) Cancer Res. 70, 299-308; Brantley-Sieders et al (2011) PLoS One 6, e24426), lung (Brannan et al (2009) Cancer Prev Res (Phila) 2, 1039-1049; Kinch et al (2003) Clin Cancer Res. 9, 613-618; Guo et al (2013) J Thorac Oncol. 8, 301-308), gastric (Nakamura et al (2005) Cancer Sci. 96, 42-47; Yuan et al (2009) Dig Dis Sci 54, 2410-2417), pancreatic (Mudali et al (2006) Clin Exp Metastasis 23, 357-365), prostate (Walker-Daniels et al (1999) Prostate 41, 275-280), liver (Yang et al (2009) Hepatol Res. 39, 1169-1177) and glioblastoma (Wykosky et al (2005) Mol Cancer Res. 3, 541-551; Li et al (2010) Tumour Biol. 31, 477-488).

The full role of EphA2 in cancer progression is still not defined although there is evidence for interaction at numerous stages of cancer progression including tumour cell growth, survival, invasion and angiogenesis. Downregulation of EphA2 expression suppresses tumour cancer cell propagation (Binda et al (2012) Cancer Cell 22, 765-780), whilst EphA2 blockade inhibits VEGF induced cell migration (Hess et al (2001) Cancer Res. 61, 3250-3255), sprouting and angiogenesis (Cheng et al (2002) Mol Cancer Res. 1, 2-11; Lin et al (2007) Cancer 109, 332-40) and metastatic progression (Brantley-Sieders et al (2005) FASEB J. 19, 1884-1886).

An antibody drug conjugate to EphA2 has been shown to significantly diminish tumour growth in rat and mouse xenograft models (Jackson et al (2008) Cancer Research 68, 9367-9374) and a similar approach has been tried in man although treatment had to be discontinued for treatment related adverse events (Annunziata et al (2013) Invest New drugs 31, 77-84).

Polypeptide ligands selected according to the method of the present invention may be employed in in vivo therapeutic and prophylactic applications, in vitro and in vivo diagnostic applications, in vitro assay and reagent applications, and the like. Ligands having selected levels of specificity are useful in applications which involve testing in non-human animals, where cross-reactivity is desirable, or in diagnostic applications, where cross-reactivity with homologues or paralogues needs to be carefully controlled. In some applications, such as vaccine applications, the ability to elicit an immune response to predetermined ranges of antigens can be exploited to tailor a vaccine to specific diseases and pathogens.

Substantially pure peptide ligands of at least 90 to 95% homogeneity are preferred for administration to a mammal, and 98 to 99% or more homogeneity is most preferred for pharmaceutical uses, especially when the mammal is a human. Once purified, partially or to homogeneity as desired, the selected polypeptides may be used diagnostically or therapeutically (including extracorporeally) or in developing and performing assay procedures, immunofluorescent stainings and the like (Lefkovite and Pernis, (1979 and 1981) Immunological Methods, Volumes I and II, Academic Press, NY).

According to a further aspect of the invention, there is provided a peptide ligand or a drug conjugate as defined herein, for use in preventing, suppressing or treating a disease or disorder characterised by overexpression of EphA2 in diseased tissue (such as a tumour).

According to a further aspect of the invention, there is provided a method of preventing, suppressing or treating a disease or disorder characterised by overexpression of EphA2 in diseased tissue (such as a tumour), which comprises administering to a patient in need thereof an effector group and drug conjugate of the peptide ligand as defined herein.

In one embodiment, the EphA2 is mammalian EphA2. In a further embodiment, the mammalian EphA2 is human EphA2.

In one embodiment, the disease or disorder characterised by overexpression of EphA2 in diseased tissue is selected from cancer.

Examples of cancers (and their benign counterparts) which may be treated (or inhibited) include, but are not limited to tumours of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, colon, rectum and anus), liver (hepatocellular carcinoma), gall bladder and biliary system, exocrine pancreas, kidney, lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, cervix, myometrium, endometrium, thyroid (for example thyroid follicular carcinoma), adrenal, prostate, skin and adnexae (for example melanoma, basal cell carcinoma, squamous cell carcinoma, keratoacanthoma, dysplastic naevus); haematological malignancies (i.e. leukemias, lymphomas) and premalignant haematological disorders and disorders of borderline malignancy including haematological malignancies and related conditions of lymphoid lineage (for example acute lymphocytic leukemia [ALL], chronic lymphocytic leukemia [CLL], B-cell lymphomas such as diffuse large B-cell lymphoma [DLBCL], follicular lymphoma, Burkitt's lymphoma, mantle cell lymphoma, T-cell lymphomas and leukaemias, natural killer [NK] cell lymphomas, Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenousleukemia [AML], chronic myelogenousleukemia [CML], chronic myelomonocyticleukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocyticleukemia); tumours of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumours, benign and malignant histiocytomas, and dermatofibrosarcomaprotuberans; tumours of the central or peripheral nervous system (for example astrocytomas, gliomas and glioblastomas, meningiomas, ependymomas, pineal tumours and schwannomas); endocrine tumours (for example pituitary tumours, adrenal tumours, islet cell tumours, parathyroid tumours, carcinoid tumours and medullary carcinoma of the thyroid); ocular and adnexal tumours (for example retinoblastoma); germ cell and trophoblastic tumours (for example teratomas, seminomas, dysgerminomas, hydatidiform moles and choriocarcinomas); and paediatric and embryonal tumours (for example medulloblastoma, neuroblastoma, Wilms tumour, and primitive neuroectodermal tumours); or syndromes, congenital or otherwise, which leave the patient susceptible to malignancy (for example Xeroderma Pigmentosum).

In a further embodiment, the cancer is selected from: breast cancer, lung cancer, gastric cancer, pancreatic cancer, prostate cancer, liver cancer, glioblastoma and angiogenesis.

In a further embodiment, the cancer is selected from: prostate cancer, lung cancer (such as non-small cell lung carcinomas (NSCLC)), breast cancer (such as triple negative breast cancer), gastric cancer, ovarian cancer, oesophageal cancer, multiple myeloma and fibrosarcoma.

In a yet further embodiment, the cancer is prostate cancer. Data is presented herein in Studies 7 and 8 which show that BCY6136 showed significant and potent anti-tumor activity in the PC-3 xenograft prostate cancer model (see FIGS. 5 and 6 and Tables 16 to 19).

In a yet further embodiment, the drug conjugate is useful for preventing, suppressing or treating solid tumours such as fibrosarcomas and breast, and non-small cell lung carcinomas.

In a yet further embodiment, the cancer is selected from lung cancer, such as non-small cell lung carcinomas (NSCLC). Data is presented herein in Study 9 which show that BCY6136 demonstrated potent antitumor activity in the NCI-H1975 xenograft lung cancer (NSCLC) model (see FIG. 8 and Tables 20 to 25). Data is also presented herein in Studies 10 and 11 which show that BCY6136 demonstrated potent anti-tumor effect in both large and small tumour size LU-01-0251 PDX lung cancer (NSCLC) models (see FIGS. 9 and 10 and Tables 26 to 29) wherein complete tumor regression was observed. Data is also presented herein in Study 12 which show that BCY6136 demonstrated significant anti-tumor effect in the LU-01-0046 PDX lung cancer (NSCLC) model (see FIG. 11 and Tables 30 and 31) wherein complete tumor regression was observed for BCY6136. Data is also presented herein in Study 13 which show that BCY6136 demonstrated dose dependent anti-tumor activity in the LU-01-0046 PDX lung cancer (NSCLC) model (see FIG. 12 and Tables 32 and 33). Data is also presented herein in Study 14 which show that BCY6173 demonstrated anti-tumor activity and BCY6136 and BCY6175 eradicated tumors in the LU-01-0046 PDX lung cancer (NSCLC) model (see FIGS. 13 to 15 and Tables 34 to 37). Data is also presented herein in Studies 15 and 16 which demonstrate the effects of BCY6136 in two models which make use of cell lines with low/negligible EphA2 expression (namely Lu-01-0412 and Lu-01-0486). This data is shown in FIGS. 23 and 24 and Tables 38 to 41 and demonstrate that BCY6136 had no effect upon tumor regression in either cell line but BCYs BCY8245 and BCY8781, which bind to a target highly expressed in the Lu-01-0412 cell line, completely eradicated the tumour. In a further embodiment, the cancer is breast cancer. In a yet further embodiment, the breast cancer is triple negative breast cancer. Data is presented herein in Study 17 which show that BCY6136 demonstrated potent antitumor activity in the MDA-MB-231 xenograft breast cancer model (see FIG. 18 and Tables 42 to 45). Data is also presented herein in Study 18 which demonstrates the effects of BCY6136 in a breast cancer model which makes use of a cell line with low/negligible EphA2 expression (namely EMT6). This data is shown in FIG. 19 and Tables 46 and 47 and demonstrates that BCY6136 had no effect upon tumor regression in this cell line. In an alternative embodiment, the breast cancer is Herceptin resistant breast cancer. Without being bound by theory, EphA2 is believed to be implicated in the resistance to Herceptin, therefore, an EphA2-targeting entity has potential utility in patients who have failed to respond to Herceptin.

In a further embodiment, the cancer is gastric cancer. Data is presented herein in Study 19 which show that BCY6136 demonstrated significant antitumor activity in the NCI-N87 xenograft gastric cancer model (see FIG. 20 and Tables 48 and 49).

In a further embodiment, the cancer is ovarian cancer. Data is presented herein in Study 20 which show that BCY6136 demonstrated significant antitumor activity in the SK-OV-3 xenograft ovarian cancer model (see FIG. 21 and Tables 50 and 51) compared with the ADC MEDI-547 which demonstrated moderate antitumour activity.

In a further embodiment, the cancer is oesophageal cancer. Data is presented herein in Study 21 which show that BCY6136 demonstrated significant antitumor activity in the OE-21 xenograft oesophageal cancer model (see FIG. 22 and Tables 52 and 53).

In a further embodiment, the cancer is multiple myeloma. Data is presented herein in Study 22 which show that BCY6136 demonstrated dose-dependent antitumor activity in the MOLP-8 xenograft multiple myeloma model (see FIG. 23).

In a further embodiment, the cancer is fibrosarcoma. Data is presented herein in Study 23 which show that BCY6173, BCY6135, BCY6174 and BCY6175 demonstrated dose dependent antitumor activity and BCY6136 demonstrated potent antitumor activity in the HT-1080 xenograft fibrosarcoma model (see FIGS. 24 to 28 and Tables 56 and 57).

References herein to the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the effectiveness of the peptide ligands in protecting against or treating the disease are available. The use of animal model systems is facilitated by the present invention, which allows the development of polypeptide ligands which can cross react with human and animal targets, to allow the use of animal models.

Furthermore, data is presented herein in Study 3 which demonstrates an association between copy number variation (CNV) and gene expression for EphA2 from multiple tumor types. Thus, according to a further aspect of the invention, there is provided a method of preventing, suppressing or treating cancer, which comprises administering to a patient in need thereof an effector group and drug conjugate of the peptide ligand as defined herein, wherein said patient is identified as having an increased copy number variation (CNV) of EphA2.

In one embodiment, the cancer is selected from those identified herein as having increased CNV of EphA2. In a further embodiment, the cancer is breast cancer.

The invention is further described below with reference to the following examples.

Examples

| Abbreviations | Name | Precursor Name | Precursor CAS | Supplier |
| --- | --- | --- | --- | --- |
| β-Ala | β-Alanine | Fmoc-β-alanine | 35737-10-1 | Fluorochem |
| D-Asp | D-Aspartic acid | Fmoc-D-aspartic acid 4-tert-butyl ester | 112883-39-3 | Sigma aldrich Sigma |
| Fl | 5(6)-carboxyfluorescein | | | |
| HArg | HomoArginine | Fmoc-L-HomoArg(Pbf)-OH | 401915-53-5 | Fluorochem |
| HyP | Hydroxyproline | Fmoc-Hydroxyproline(tBu)-OH | 122996-47-8 | Sigma |
| Sar | Sarcosine, such that Sar$_x$ represents x Sar residues | Fmoc-Sarcosine-OH | 77128-70-2 | Sigma |

Materials and Methods

Peptide Synthesis tides were synthesized by solid phase synthesis. Rink Amide MBHA Resin was used. To a mixture containing Rink Amide MBHA (0.4-0.45 mmol/g) and Fmoc-Cys(Trt)-OH (3.0 eq) was added DMF, then DIC (3 eq) and HOAt (3 eq) were added and mixed for 1 hour. 20% piperidine in DMF was used for deblocking. Each subsequent amino acid was coupled with 3 eq using activator reagents, DIC (3.0 eq) and HOAT (3.0 eq) in DMF. The reaction was monitored by ninhydrin color reaction or tetrachlor color reaction. After synthesis completion, the peptide resin was washed with DMF×3, MeOH×3, and then dried under $N_2$ bubbling overnight. The peptide resin was then treated with 92.5% TFA/2.5% TIS/2.5%/EDT/2.5%/$H_2O$ for 3 h. The peptide was precipitated with cold isopropyl ether and centrifuged (3 min at 3000 rpm). The pellet was washed twice with isopropyl ether and the crude peptide was dried under vacuum for 2 hours and then lyophilised. The lyophilised powder was dissolved in of ACN/$H_2O$ (50:50), and a solution of 100 mM TATA in ACN was added, followed by ammonium bicarbonate in $H_2O$ (1M) and the solution mixed for 1 h. Once the cyclisation was complete, the reaction was quenched with 1M aq. Cysteine hydrochloride (10 eq relative to TATA), then mixed and left to stand for an hour. The solution was lyophilised to afford crude product. The crude peptide was purified by Preparative HPLC and lyophilized to give the product All amino acids, unless noted otherwise, were used in the L-configurations.

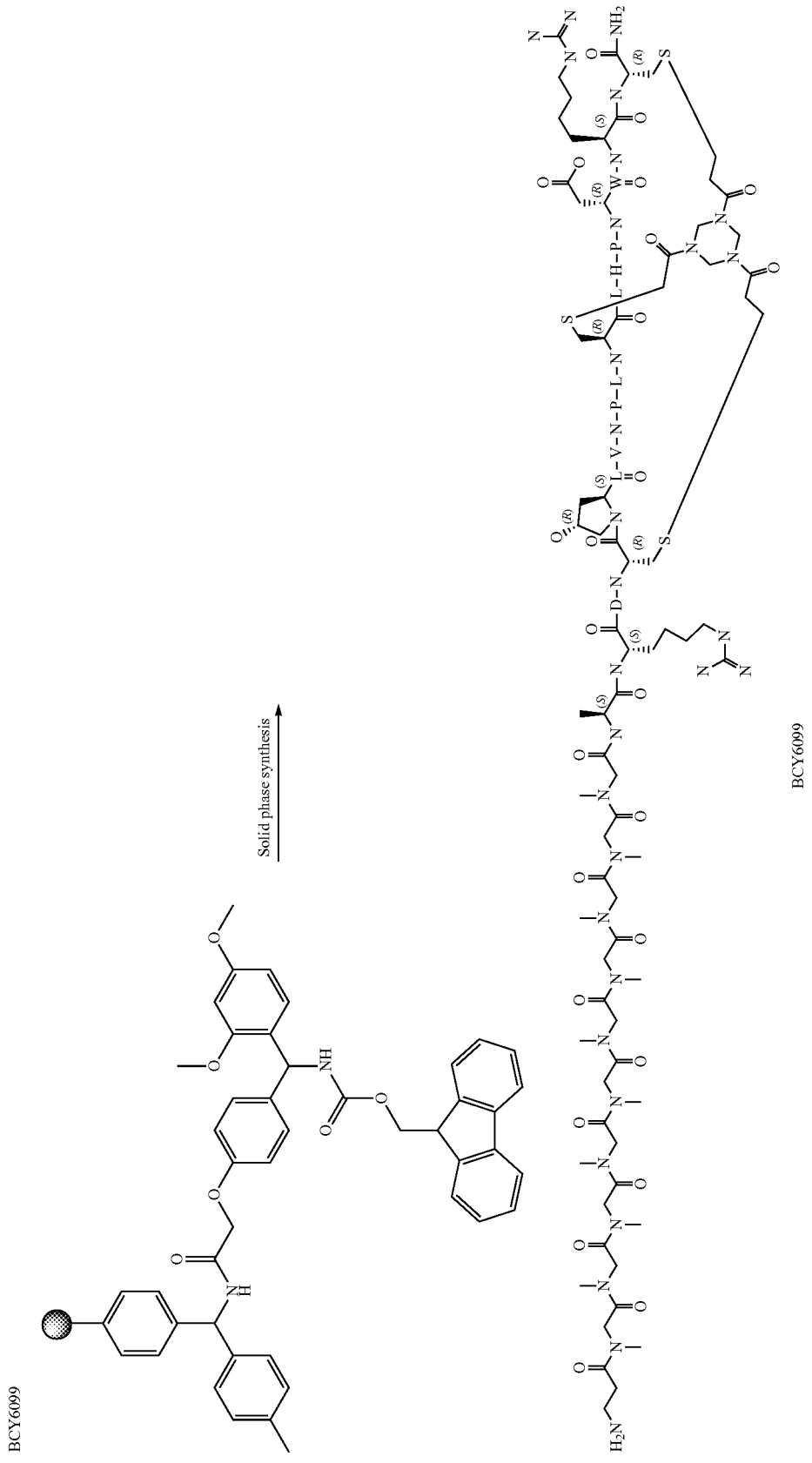

Sequence: (β-Ala)-Sar$_{10}$-(SEQ ID NO: 2)-CONH$_2$ 8.0 g of resin was used to generate 2.1 a BCY6099 (99.2% purity; 16.3% yield) as a white solid.

| BCY6099 Analytical Data | |
|---|---|
| Mobile Phase: | A: 0.1% TFA in H$_2$O B: 0.1% TFA in ACN |
| Flow: | 1.0 ml/min |
| Column: | Gemini-NX C18 5 μm 110A 150 * 4.6 mm |
| Instrument: | Agilent 1200 HPLC-BE(1-614) |
| Method: | 15-45% B over 20 minutes, then 3 min 95% B |
| Retention Time: | 11.31 min |
| LCMS (ESI): | m/z 1061.8 [M + 3H]$^{3+}$, 796.5 [M + 4H]$^{4+}$ |
| Peptide mw | 3183.68 |

Preparation of Bicyclic Peptide Drug Conjugates

The general schematic for preparing Bicycle drug conjugates (BDCs) is shown in FIG. 1 and Table A describes the component targeting bicycle and linker/toxin within each BDC.

TABLE A

| BDC (BCY Number) | Targetting Bicycle (BCY Number) | Linker/Toxin |
|---|---|---|
| 6135 | 6099 | DM1-SS- |
| 6136 | 6099 | ValCit-MMAE |
| 6173 | 6099 | DM1-SS(SO$_3$H)- |
| 6174 | 6099 | ValLys-MMAE |
| 6175 | 6099 | MMAE-D-Ala-Phe-Lys- |

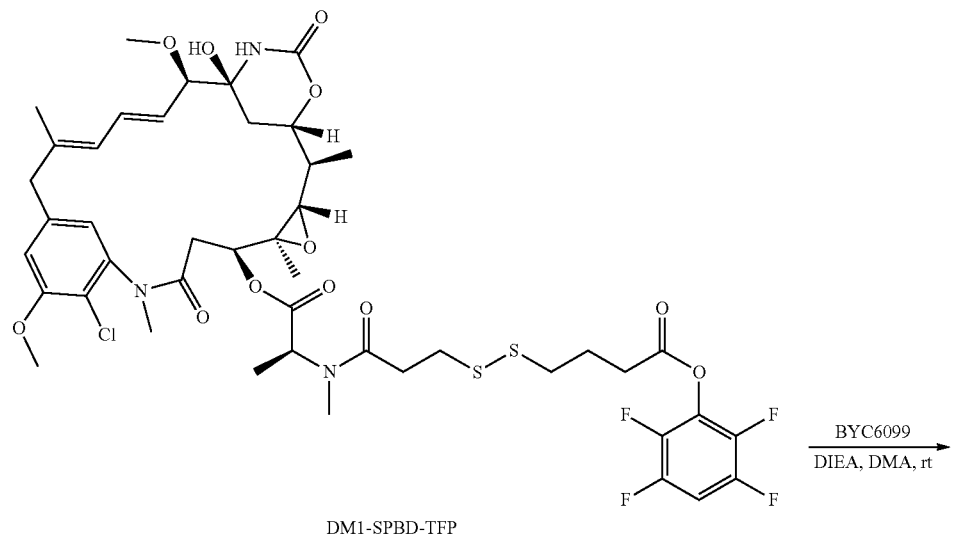

BCY6135

DM1-SPBD-TFP

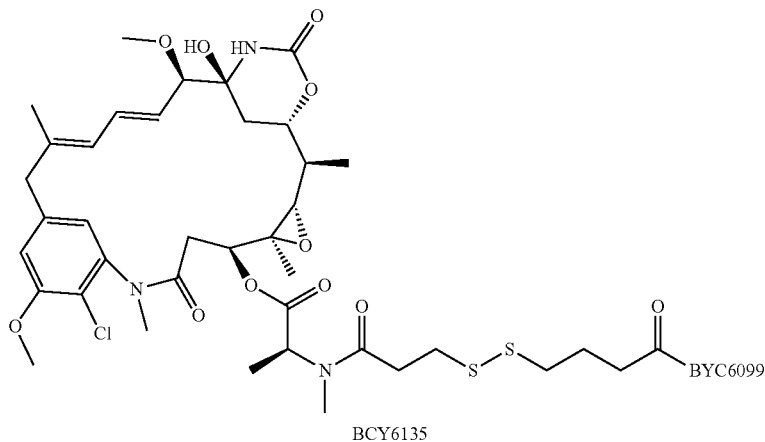

BCY6135

BCY6099 (114.1 mg, 35.84 μmol) was used as the bicycle reagent. 22.4 mg Compound BCY6135 (5.30 μmol, 17.74% yield. 95.14% purity) was obtained as a white solid.

|  | BCY6135 Analytical Data |
|---|---|
| Mobile Phase: | A: 0.1% TFA in $H_2O$ B: 0.1% TFA in ACN |
| Flow: | 1.0 ml/min |
| Column: | Gemini-NX C18 5 μm 110A 150 * 4.6 mm |
| Instrument: | Agilent 1200 HPLC-BE(1-614) |
| Method: | 28-68% B over 30 minutes, then 3 min 95% B |
| Retention Time: | 9.81 |
| LCMS (ESI): | m/z 1341.5 $[M + 3H]^{3+}$, 805.0 $[M + 5H]^{5+}$ |
| Peptide mw | 4021.08 |

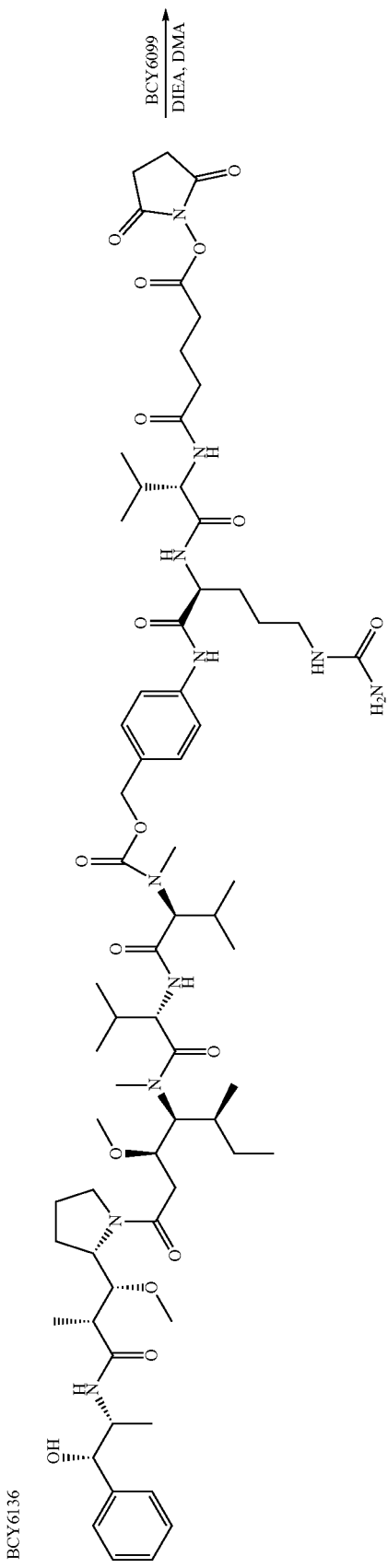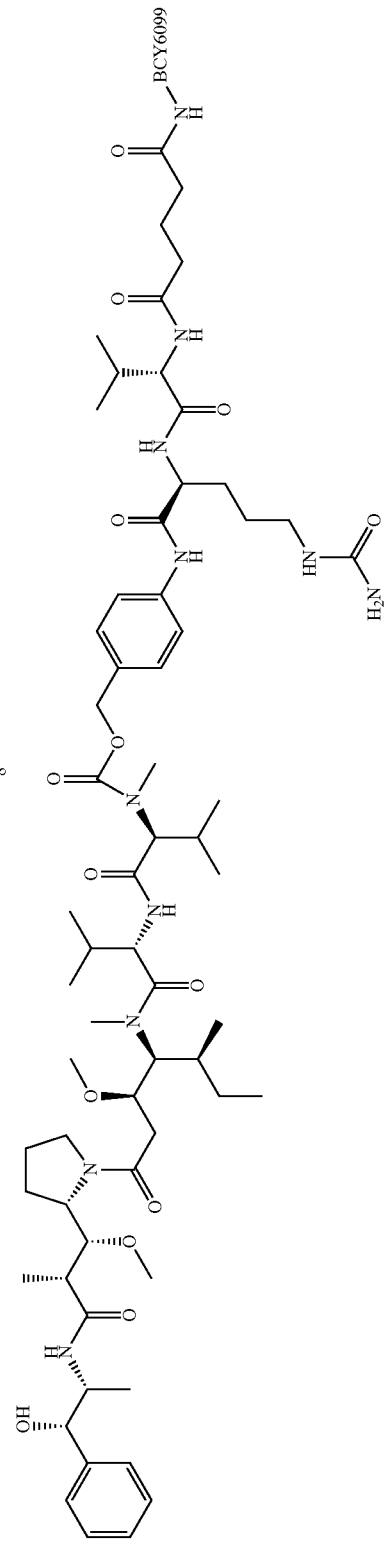

BCY6099 (71.5 mg, 22.48 μmol) was used as the bicycle reagent. Compound BCY6136 (40.9 mg, 9.05 μmol, 40.27% yield, 97.42% purity) was obtained as a white solid.

| BCY6136 Analytical Data | |
|---|---|
| Mobile Phase: | A: 0.1% TFA in $H_2O$ B: 0.1% TFA in ACN |
| Flow: | 1.0 ml/min |
| Column: | Gemini-NX C18 5 μm 110A 150 * 4.6 mm |
| Instrument: | Agilent 1200 HPLC-BE(1-614) |
| Method: | 28-68% B over 30 minutes, then 3 min 95% B |
| Retention Time: | 11.35 min |
| LCMS (ESI): | m/z 1468.1 $[M + 3H]^{3+}$, 1101.2 $[M + 4H]^{4+}$, 881.3 $[M + 5H]^{5+}$ |
| Peptide mw | 4404.2 |

BCY6099 (200.15 mg, 62.89 μmol) was used as the bicycle reagent. 57.1 mg compound BCY6173 (3.40 μmol, 22.79% yield, 95.80% purity) was obtained as a white solid.

| BCY6173 Analytical Data | |
|---|---|
| Mobile Phase: | A: 0.1% TFA in $H_2O$ B: 0.1% TFA in ACN |
| Flow: | 1.0 ml/min |
| Column: | Gemini-NX C18 5 μm 110A 150 * 4.6 mm |
| Instrument: | Agilent 1200 HPLC-BE(1-614) |
| Method: | 28-68% B over 30 minutes, then 3 min 95% B |
| Retention Time: | 10.30 min |
| LCMS (ESI): | m/z 1361.9 $[M + 3H - H_2O]^{3+}$, 1021.8 $[M + 4H - H_2O]^{4+}$ |
| Peptide mw | 4101.15 |

BCY6173

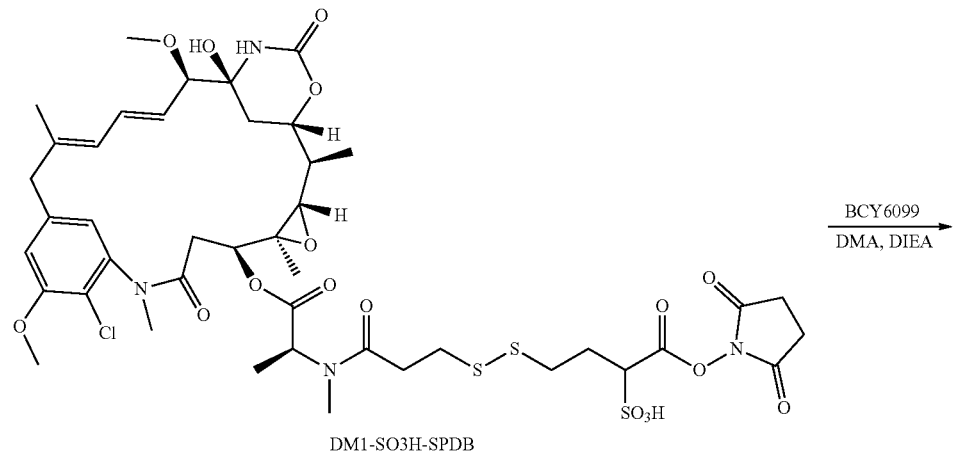

DM1-SO3H-SPDB

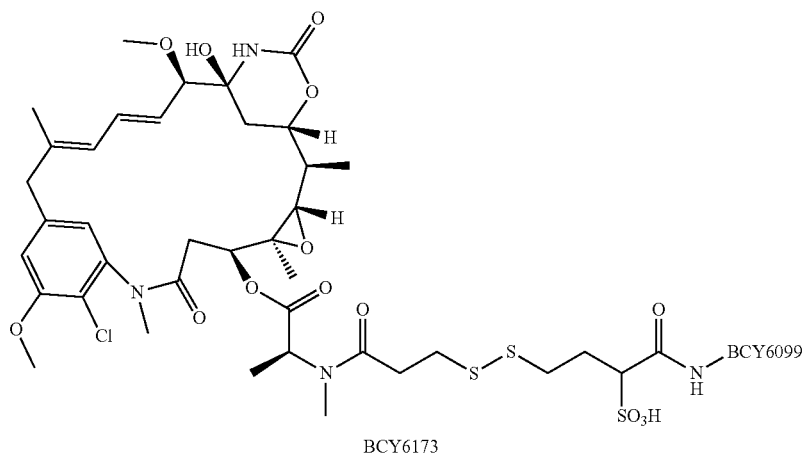

BCY6173

BCY6174

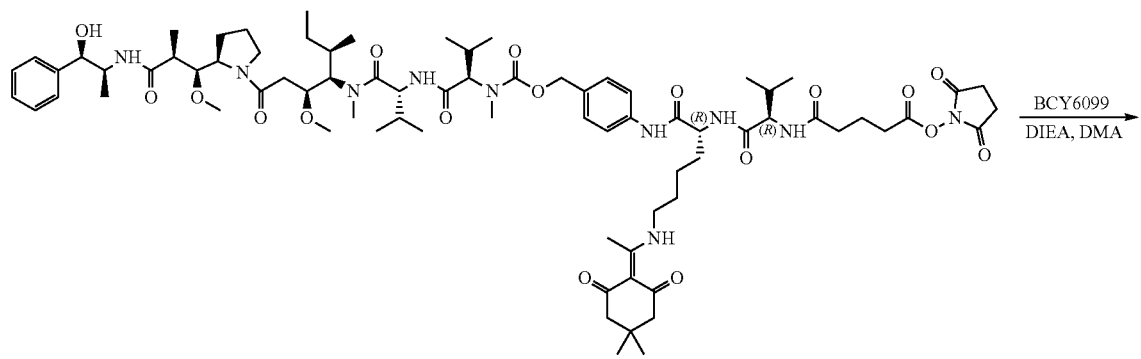

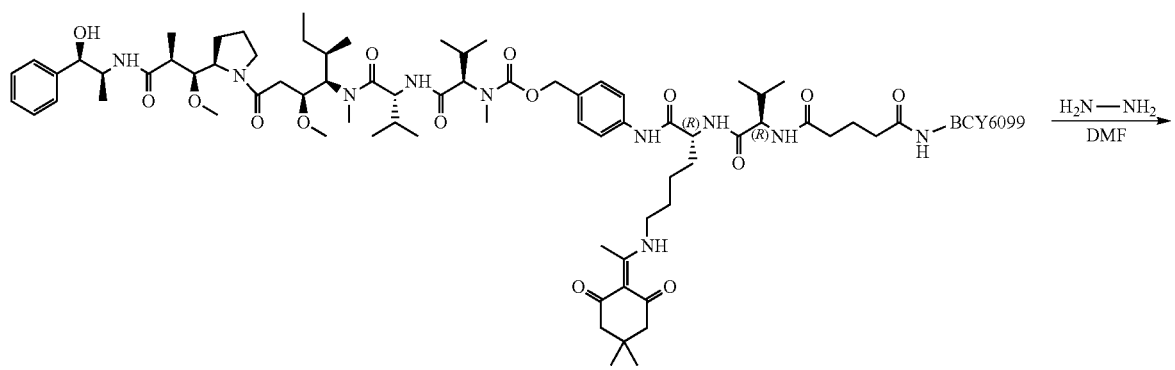

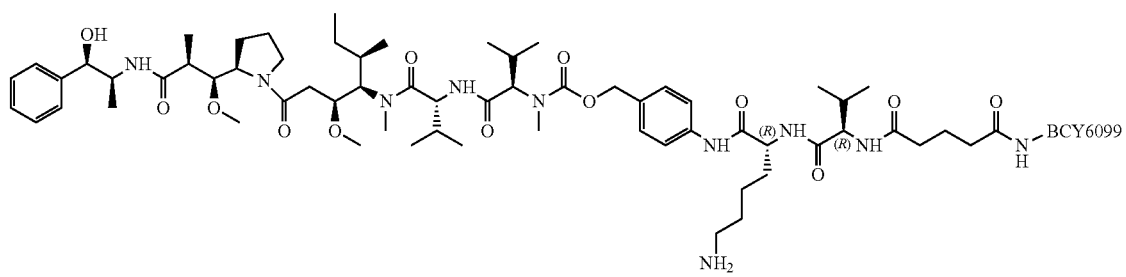

BCY6099 (389.77 mg, 122.47 μmol, 1.2 eq) was used as the bicycle reagent. Dde-BCY6174 (0.250 g, 55.10 μmol, 53.99% yield) was obtained as a white solid.

| LCMS (ESI): | m/z 1513.0 [M + 3H]$^{3+}$, 1135.0 [M + 4H]$^{4+}$, 908.2 [M + 5H]$^{5+}$ |
|---|---|
| Molecular weight | 4538.38 |

Dde-BCY6174 (0.250 g, 55.10 μmol, 1.0 eq) was deprotected using hydrazine according to the general procedure to give BCY6174 (0.1206 g, 27.45 μmol, 49.82% yield) as a white solid.

| BCY6174 Analytical Data | |
|---|---|
| Mobile Phase: | A: 0.1% TFA in H$_2$O B: 0.1% TFA in ACN |
| Flow: | 1.0 ml/min |
| Column: | Gemini-NX C18 5 μm 110A 150 * 4.6 mm |
| Instrument: | Agilent 1200 HPLC-BE(1-614) |
| Method: | 28-68% B over 30 minutes, then 3 min 95% B |
| Retention Time: | 9.85 min |
| LCMS (ESI): | m/z 1458.5 [M + 3H]$^{3+}$, 1094.1 [M + 4H]$^{4+}$, 875.4 [M + 5H]$^{5+}$ |
| Peptide mw | 4373.17 |

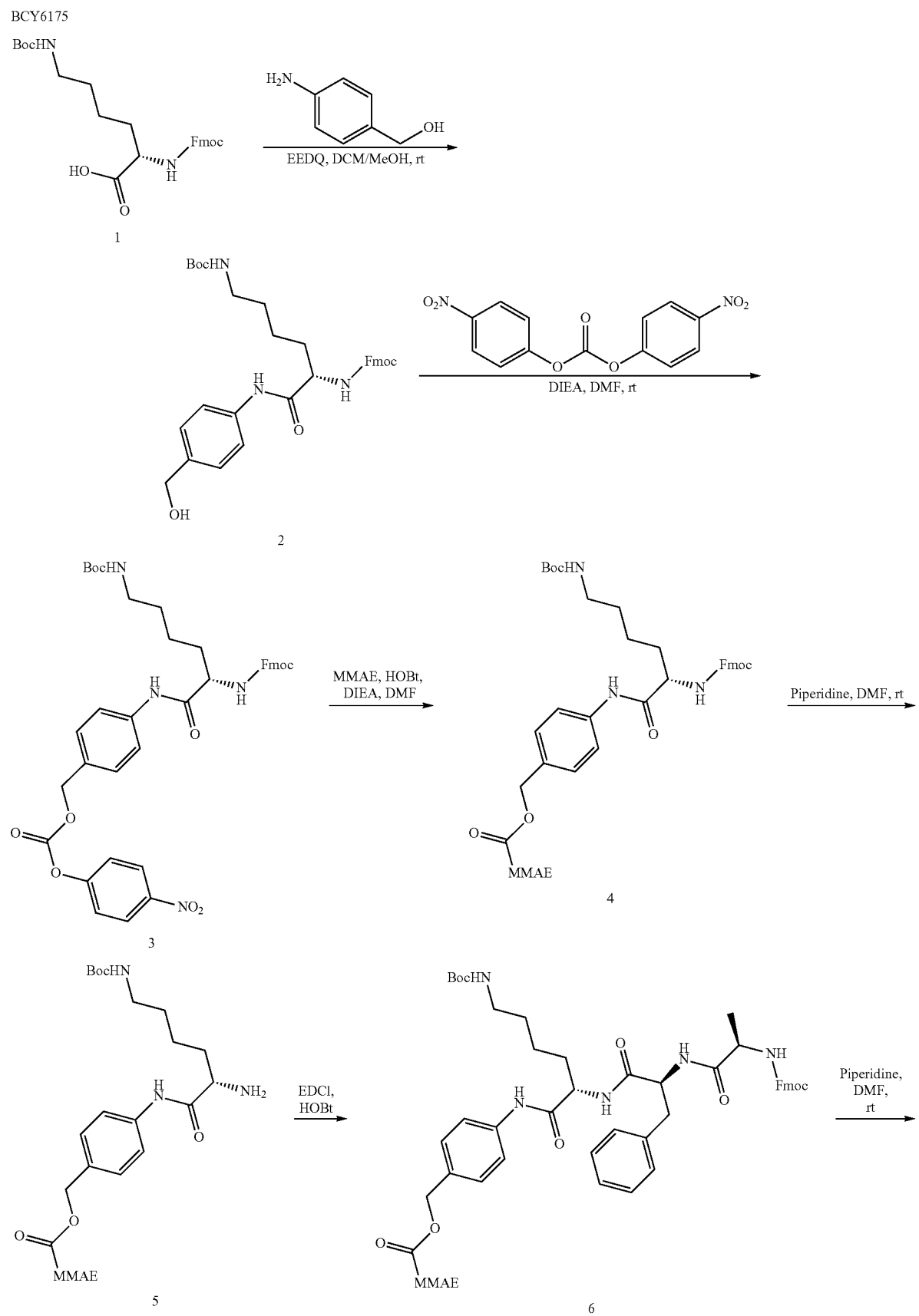

-continued
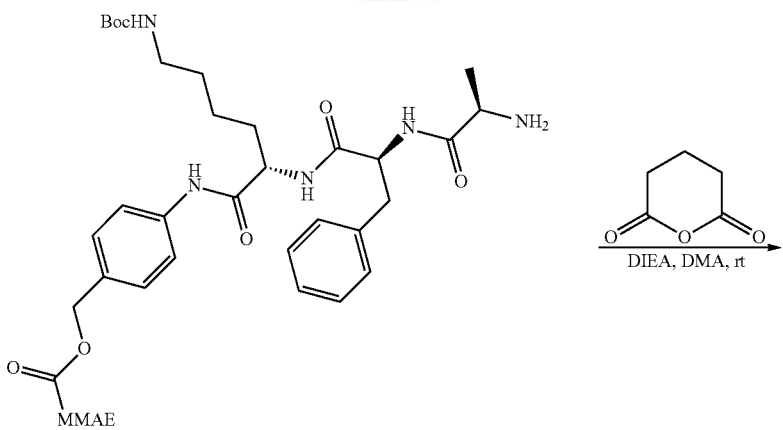
7
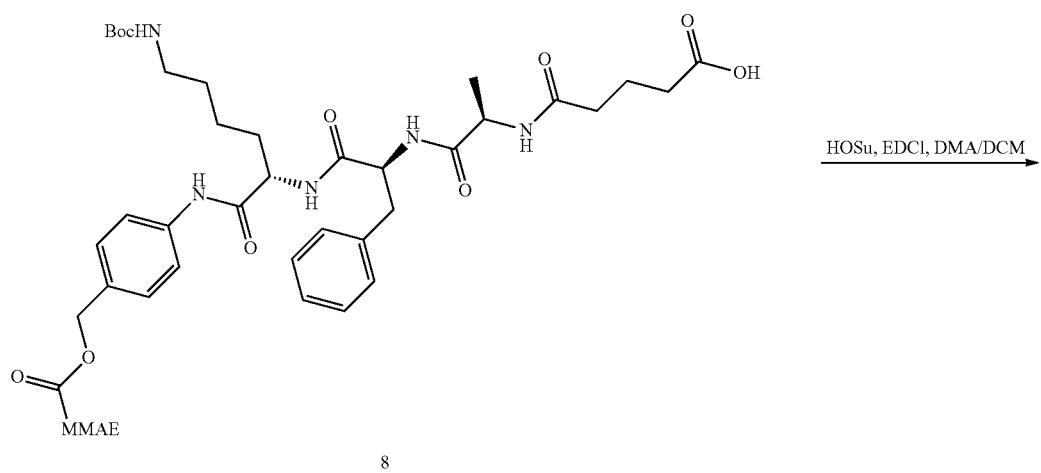
8
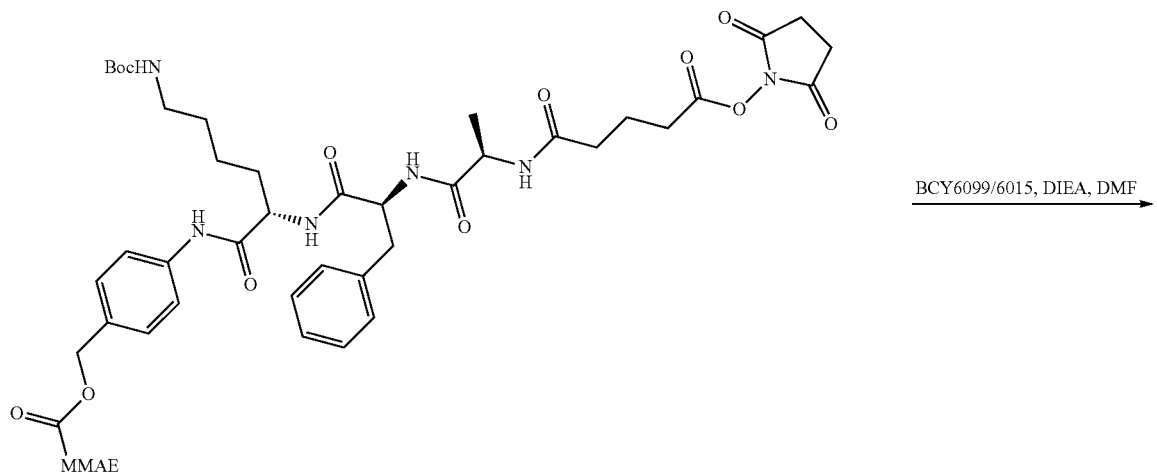
9

-continued

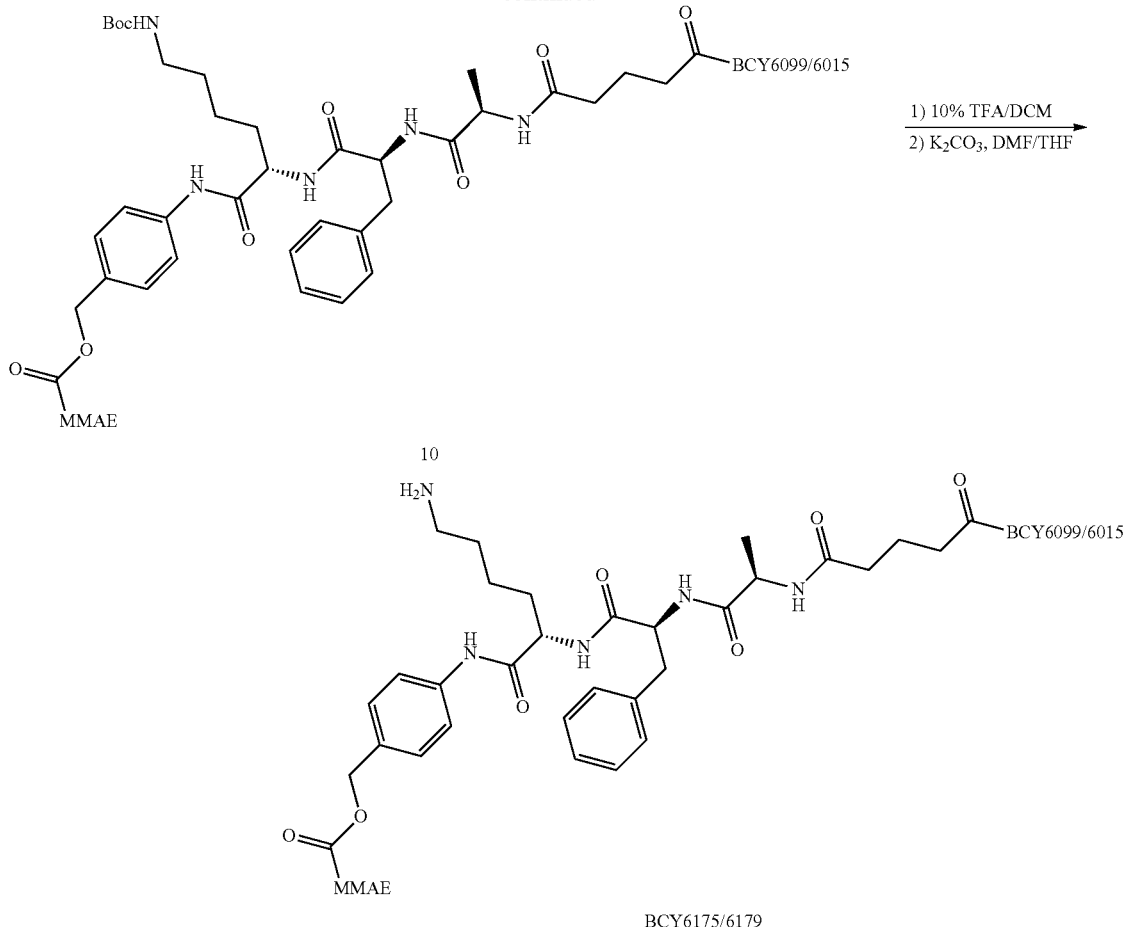

General Procedure for Preparation of Compound 10A

To a solution of BCY6099 (195.15 mg, 61.32 μmol, 1.1 eq) in DMA (3 mL) were added DIEA (21.61 mg, 167.23 μmol, 29.13 μL, 3 eq) and compound 9 (0.085 g, 55.74 μmol, 1.0 eq). The mixture was stirred at 25° C. for 16 hr. LC-MS showed compound 9 was consumed completely and one main peak with desired m/z was detected. The reaction mixture was concentrated under reduced pressure to remove solvent to afford a residue (light yellow oil). The reaction was directly purified by prep-HPLC (neutral condition). Compound 10A (0.160 g, 34.84 μmol, 62.50% yield) was obtained as a white solid.

General Procedure for Preparation of BCY6175

To a solution of compound 10A in DCM (4.5 mL) was added TFA (4.5 mL). The mixture was stirred at 0° C. for 30 min. LC-MS showed compound 10A was consumed completely and one main peak with desired m/z was detected. The reaction mixture was concentrated under reduced pressure to remove solvent to afford a residue, which was purified by prep-HPLC (TFA condition). Compound BCY6175 (61.40 mg, 13.56 μmol, 31.13% yield) was obtained as a white solid.

Biological Data

Study 1: Fluorescence Polarisation Measurements (a) Direct Binding Assay

Peptides with a fluorescent tag (either fluorescein, SIGMA or Alexa Fluor488™, Fisher Scientific) were diluted to 2.5 nM in PBS with 0.01% tween 20 or 50 mM HEPES with 100 mM NaCl and 0.01% tween pH 7.4 (both referred to as assay buffer). This was combined with a titration of protein in the same assay buffer as the peptide to give 1 nM peptide in a total volume of 25 μL in a black walled and bottomed low bind low volume 384 well plates, typically 5 μL assay buffer, 10 μL protein (Table 1) then 10 μL fluorescent peptide. One in two serial dilutions were used to give 12 different concentrations with top concentrations ranging from 500 nM for known high affinity binders to 10 μM for low affinity binders and selectivity assays. Measurements were conducted on a BMG PHERAstar FS equipped with an "FP 485 520 520" optic module which excites at 485 nm and detects parallel and perpendicular emission at 520 nm. The PHERAstar FS was set at 25° C. with 200 flashes per well and a positioning delay of 0.1 second, with each well measured at 5 to 10 minute intervals for 60 minutes. The gain used for analysis was determined for each tracer at the end of the 60 minutes where there was no protein in the well. Data was analysed using Systat Sigmaplot version 12.0. mP values were fit to a user defined quadratic equation to generate a Kd value: f=ymin+(ymax−ymin)/Lig*((x+Lig+Kd)/2-sqrt((((x+Lig+Kd)/2)^2)−(Lig*x))). "Lig" was a defined value of the concentration of tracer used.

(b) Competition Binding Assay

Peptides without a fluorescent tag were tested in competition with a peptide with a fluorescent tag and a known Kd (Table 2). Reference Compound A has the sequence FI-G-Sar$_5$-ACPWGPAWCPVNRPGCA (FI-G-Sar$_5$-(SEQ ID NO:

4)). Reference Compound B has the sequence FI-G-Sar$_5$-ACPWGPFWCPVNRPGCA (FI-G-Sar$_5$-(SEQ ID NO: 5)). Reference Compound C has the sequence FI-G-Sar$_5$-AD-VTCPWGPFWCPVNRPGCA (FI-G-Sar$_5$-(SEQ ID NO: 6)). Each of Reference Compounds A, B and C contain a TBMB molecular scaffold.

Peptides were diluted to an appropriate concentration in assay buffer as described in the direct binding assay with a maximum of 5% DMSO, then serially diluted 1 in 2. Five μL of diluted peptide was added to the plate followed by 10 μL of human or mouse EphA2 (Table 1) at a fixed concentration which was dependent on the fluorescent peptide used (Table 2), then 10 μL fluorescent peptide added. Measurements were conducted as for the direct binding assay, however the gain was determined prior to the first measurement. Data analysis was in Systat Sigmaplot version 12.0 where the mP values were fit to a user defined cubic equation to generate a Ki value:

f=ymin+(ymax−ymin)/Lig*(Lig*((2*((Klig+Kcomp+Lig+Comp−Prot*c)^2−3*(Kcomp*(Lig−Prot*c)+Klig*(Comp−Prot*c)+Klig*Kcomp))^0.5*COS(ARCCOS((−2*(Klig+Kcomp+Lig+Comp−Prot*c)^3+9*(Klig+Kcomp+Lig+Comp−Prot*c)*(Kcomp*(Lig−Prot*c)+Klig*(Comp−Prot*c)+Klig*Kcomp)−27*(−1*Klig*Kcomp*Prot*c))/(2*((((Klig+Kcomp+Lig+Comp−Prot*c)^2−3*(Kcomp*(Lig−Prot*c)+Klig*(Comp−Prot*c)+Klig*Kcomp))^3)^0.5)))/3))−(Klig+Kcomp+Lig+Comp−Prot*c)))/(3*Klig)+((2*((Klig+Kcomp+Lig+Comp−Prot*c)^2−3*(Kcomp*(Lig−Prot*c)+Klig*(Comp−Prot*c)+Klig*Kcomp))^0.5*COS(ARCCOS((−2*(Klig+Kcomp+Lig+Comp−Prot*c)^3+9*(Klig+Kcomp+Lig+Comp−Prot*c)*(Kcomp*(Lig−Prot*c)+Klig*(Comp−Prot*c)+Klig*Kcomp)−27*(−1*Klig*Kcomp*Prot*c))/(2*((((Klig+Kcomp+Lig+Comp−Prot*c)^2−3*(Kcomp*(Lig−Prot*c)+Klig*(Comp−Prot*c)+Klig*Kcomp))^3)^0.5)))/3))−(Klig+Kcomp+Lig+Comp−Prot*c)))). "Lig", "KLig" and "Prot" were all defined values relating to: fluorescent peptide concentration, the Kd of the fluorescent peptide and EphA2 concentration respectively.

TABLE 1

Ephrin receptors and source

| Receptor (domain) | Species | Format/tag | Supplier | Catalogue number |
|---|---|---|---|---|
| EphA1 (Ecto) | Human | Fc fusion | R&D systems | 7146-A1 |
| EphA2 (Ecto) | Human | C-terminal polyHis | R&D systems | 3035-A2 |
| EphA2 (Ecto) | Human | C-terminal polyHis | In-house | N/A |
| EphA2 (Ecto) | Mouse | Fc fusion | R&D Systems | 639-A2 |
| EphA2 (Ecto) | Mouse | C-terminal polyHis | Sino Biological | 50586-M08H |
| EphA2 (ligand binding) | Rat | C-terminal polyHis | In-house | N/A |
| EphA2 (ligand binding) | Dog | C-terminal polyHis | In-house | N/A |
| EphA3 (Ecto) | Human | Fc fusion | R&D systems | 6444-A3 |
| EphA3 (Ecto) | Human | N-terminal polyHis | In-house | N/A |
| EphA3 (Ecto) | Rat | C-terminal polyHis | Sino Biological | 80465-R08H |
| EphA4 (Ecto) | Human | Fc fusion | R&D systems | 6827-A4 |
| EphA4 (Ecto) | Human | C-terminal polyHis | Sino Biological | 11314-H08H |
| EphA4 (Ecto) | Rat | C-terminal polyHis | Sino Biological | 80123-R08H |
| EphA6 (Ecto) | Human | Fc fusion | R&D systems | 5606-A6 |
| EphA7 (Ecto) | Human | Fc fusion | R&D systems | 6756-A7 |
| EphB1 (Ecto) | Rat | Fc fusion | R&D systems | 1596-B1 |
| EphB4 (Ecto) | human | C-terminal polyHis | R&D systems | 3038-B4 |

TABLE 2

Final concentrations of fluorescent peptide and EphA2 as used with Competition Binding Assays

| Fluorescent peptide | Concentration of fluorescent peptide (nM) | Concentration of Human EphA2 (nM) | Concentration of Mouse EphA2 (nM) |
|---|---|---|---|
| Reference Compound A | 10 | 75 | |
| Reference Compound B | 1 | 30 | |
| Reference Compound C | 0.8 (human) 1 (mouse) | 2.4 | 50 |

Certain peptide ligands of the invention were tested in the above mentioned assays and the results are shown in Tables 3 and 4:

TABLE 3

Biological Assay Data for Peptide Ligand of the Invention
(TATA peptides Competition Binding Assay)

| | | | Ki, nM ± 95% CI | |
|---|---|---|---|---|
| | | | Human EphA2 | Human EphA2 |
| Bicycle Compound Number | Sequence | Scaffold | Fluorescent Peptide, Reference Compound C | |
| BCY6099 | (β-Ala)-Sar$_{10}$-A(HArg)DC(HyP)LVNPLCLHP(D-Asp)W(HArg)C (SEQ ID NO: 2) | TATA | 4.94 ± 1.41 | 57.6 ± 24.86 |

TABLE 4

Biological Assay Data for Peptide Ligands of the Invention (BDC competition binding data with TATA Scaffolds)

| BDC Compound Number | Bicycle precursor | General Formula | Scaffold | Ki, nM, Human EphA2 Fluorescent Peptide, Reference Compound C |
|---|---|---|---|---|
| BCY6027 | BCY6099 | Formula (A) | TATA | 10.23 |
| BCY6028 | BCY6099 | Formula (B) | TATA | 13.04 |

Study 2: Fluorescence Polarisation Measurements (Alternative Protocol)

(a) Competition Binding

Peptides without a fluorescent tag were tested in competition with a peptide with a fluorescent tag and a known Kd (Table 9). Five μL of increasing (2 fold) concentrations of test compound was added to the plate followed by 10 μL of EphA2 protein (Table 8) at a fixed concentration which was dependent on the fluorescent peptide used (Table 9), then 10 μL fluorescent peptide added. Buffer was assay buffer as above with DMSO <1%. Measurements were conducted on a BMG PHERAstar FS equipped with an "FP 485 520 520" optic module which excites at 485 nm and detects parallel and perpendicular emission at 520 nm. The PHERAstar FS was set at 25° C. with 200 flashes per well and a positioning delay of 0.1 second, with each well measured at 5 to 10 minute intervals for 60 minutes. Alternatively, measurements were done on at similar time intervals on a Perkin Elmer Envision equipped with FITC FP Dual Mirror, FITC FP 480 excitation filter and FITC FP P-pol 535 and FITC FP S-pol emission filters with 30 flashes and a G-Factor of 1.2. Data analysis was in Systat Sigmaplot version 12.0 or 13.0 where the mP values at 60 minutes were fit to a user defined cubic equation to generate a Ki value:

f=ymin+(ymax−ymin)/Lin(Lin(2*((Klig+Kcomp+Lig+Comp−Prot*c)^2−3*(Kcomp*(Lig−Prot*c)+Klig*(Comp−Prot*c)+Klig*Kcomp))^0.5*COS(ARCCOS((−2*(Klig+Kcomp+Lig+Comp−Prot*c)^3+9*(Klig+Kcomp+Lig+Comp−Prot*c)*(Kcomp*(Lig−Prot*c)+Klig*(Comp−Prot*c)+Klig*Kcomp)−27*(−1*Klig*Kcomp*Prot*c))/(2*(((Klig+Kcomp+Lig+Comp−Prot*c)^2−3*(Kcomp*(Lig−Prot*c)+Klig*(Comp−Prot*c)+Klig*Kcomp))^3)^0.5))/3)−(Klig+Kcomp+Lig+Comp−Prot*c)))/((3*Klig)+((2*((Klig+Kcomp+Lig+Comp−Prot*c)^2−3*(Kcomp*(Lig−Prot*c)+Klig*(Comp−Prot*c)+Klig*Kcomp))^0.5*COS(ARCCOS((−2*(Klig+Kcomp+Lig+Comp−Prot*c)^3+9*(Klig+Kcomp+Lig+Comp−Prot*c)*(Kcomp*(Lig−Prot*c)+Klig*(Comp−Prot*c)+Klig*Kcomp)−27*(−1*Klig*Kcomp*Prot*c))/(2*((((Klig+Kcomp+Lig+Comp−Prot*c)^2−3*(Kcomp*(Lig−Prot*c)+Klig*(Comp−Prot*c)+Klig*Kcomp))^3)^0.5)))/3))−(Klig+Kcomp+Lig+Comp−Prot*c)))). "Lig", "KLig" and "Prot" were all defined values relating to: fluorescent peptide concentration, the Kd of the fluorescent peptide and EphA2 concentration respectively.

TABLE 5

Eph receptors and source

| Receptor (domain) | Species | Format/tag | Supplier | Catalogue number |
|---|---|---|---|---|
| EphA2 (Ecto) | Human | C-terminal polyHis | R&D systems | 3035-A2 |
| EphA2 (Ecto) | Human | C-terminal polyHis | In-house | N/A |
| EphA2 (Ecto) | Mouse | C-terminal polyHis | Sino Biological | 50586-M08H |
| EphA2 (ligand binding) | Rat | C-terminal polyHis | In-house | N/A |

TABLE 6

Final concentrations of fluorescent peptide and EphA2 as used with competition binding assays

| Fluorescent peptide | Concentration of fluorescent peptide (nM) | Concentration of human EphA2 (nM) | Concentration of mouse EphA2 (nM) | Concentration of rat EphA2 (nM) |
|---|---|---|---|---|
| Reference Compound C | 0.8 | 2.4 or 25 | 50 or 15 nM | 25 |

Certain peptide ligands and bicycle drug conjugates of the invention were tested in the above mentioned competition binding assay and the results are shown in Table 7:

TABLE 7

Competition Binding with Selected Bicyclic Peptides

| Bicycle No. | Human Ki (nM) | Mouse Ki (nM) | Rat Ki (nM) |
|---|---|---|---|
| BCY6099 | 2.7 | 4.5 | 1.9 |

The results from the competition binding assay in Table 7 show that Bicycle peptides targeting human EphA2 (BCY6099) bind with high affinity to mouse and rat EphA2. These results show that the peptide of the invention can be used in in vivo mouse and rat efficacy and toxicology models.

TABLE 8

Competition Binding with Selected Bicycle Drug Conjugates (BDCs)

| Bicycle ID | Human Ki (nM) | Mouse Ki (nM) | Rat Ki (nM) |
|---|---|---|---|
| BCY6027 | 10.2 | | |
| BCY6028 | 13.0 | | |
| BCY6135 | 2.4 | 5.0 | 2.9 |
| BCY6136 | 1.9 | 5.5 | 3.2 |
| BCY6173 | 1.7 | 4.3 | 2.5 |
| BCY6174 | 1.7 | 3.9 | 3.0 |

Table 8 shows that certain Bicycle Drug Conjugates of the invention exhibit excellent cross reactivity between human, mouse and rodent EphA2. The peptide of the invention can therefore be used in mouse and rat efficacy and toxicology in vivo models.

(b) SPR Measurements

Non-Fc fusion proteins were biotinylated with EZ-Link™ Sulfo-NHS-LC-Biotin for 1 hour in 4 mM sodium acetate, 100 mM NaCl, pH 5.4 with a 3× molar excess of biotin over protein. The degree of labelling was determined using a Fluorescence Biotin Quantification Kit (Thermo) after dialysis of the reaction mixture into PBS. For analysis of peptide binding, a Biacore T200 instrument was used utilising a XanTec CMD500D chip. Streptavidin was immobilized on the chip using standard amine-coupling chemistry at 25° C. with HBS-N (10 mM HEPES, 0.15 M NaCl, pH 7.4) as the running buffer. Briefly, the carboxymethyl dextran surface was activated with a 7 min injection of a 1:1 ratio of 0.4 M 1-ethyl-3-(3-dimethylaminopropyl) carbodiimide hydrochloride (EDC)/0.1 M N-hydroxy succinimide (NHS) at a flow rate of 10 Ξl/min. For capture of streptavidin, the protein was diluted to 0.2 mg/ml in 10 mM sodium acetate (pH 4.5) and captured by injecting 120 μl onto the activated chip surface. Residual activated groups were blocked with a 7 min injection of 1 M ethanolamine (pH 8.5):HBS-N (1:1). Buffer was changed to PBS/0.05% Tween 20 and biotinylated EphA2 was captured to a level of 500-1500 RU using a dilution of protein to 0.2 μM in buffer. A dilution series of the peptides was prepared in this buffer with a final DMSO concentration of 0.5% with a top peptide concentration was 50 or 100 nM and 6 further 2-fold dilutions. The SPR analysis was run at 25° C. at a flow rate of 90 μl/min with 60 seconds association and 900-1200 seconds dissociation. Data were corrected for DMSO excluded volume effects. All data were double-referenced for blank injections and reference surface using standard processing procedures and data processing and kinetic fitting were performed using Scrubber software, version 2.0c (BioLogic Software). Data were fitted using simple 1:1 binding model allowing for mass transport effects where appropriate.

For binding of Bicycle Drug Conjugates a Biacore 3000 instrument was used. For biotinylated proteins immobilisation levels were 1500 RU and the top concentration was 100 nM. Otherwise the method was the same as described above using either the CMD500D or a CM5 chip (GE Healthcare). For the Fc-tagged proteins, a CM5 chip was activated as described above and then goat anti-human IgG antibody (Thermo-Fisher H10500) was diluted to 20 μg/ml in 10 mM sodium acetate pH5.0 and captured to approximately 3000 RU. The surface was then blocked as described above. Subsequent capture of the Fc-tagged proteins was carried out to obtain approximately 200-400 RU of the target protein. The proteins used are described below. All proteins were reconstituted as per manufacturer's suggested buffers and concentrations and captured using 5-10 μg/ml protein in PBS/0.05% Tween 20.

TABLE 9

| Receptor | Species | Format/tag | Supplier | Catalogue number |
|---|---|---|---|---|
| EphA1 | Human | Fc fusion | Sino Biologics | 15789-H02H |
| EphA2 | Human | 0.95 mol biotin/monomer | In house | N/A |
| EphA2 | Mouse | Fc fusion | R&D Systems | 639-A2 |
| EphA2 | Rat | 1.4 mol biotin/monomer | In house | N/A |
| EphA3 | Human | Fc fusion | R&D Systems | 6444-A3 |
| EphA3 | Mouse | Fc fusion | Sino Biologics | 51122-M02H |
| EphA3 | Rat | Fc fusion | Sino Biologics | 80465-R02H |
| EphA4 | Human | Fc fusion | Sino Biologics | 11314-H03H |
| EphA4 | Mouse | Fc fusion | Sino Biologics | 50575-M02H |
| EphA4 | Rat | Fc fusion | Sino Biologics | 80123-R02H |
| EphA5 | Human | 3.1 mol biotin/monomer | R&D Systems | 3036-A5 |
| EphA6 | Human | Fc fusion | R&D Systems | 5606-A6 |
| EphA7 | Human | Fc fusion | R&D Systems | 6756-A7 |
| EphB1 | Rat | Fc fusion | R&D Systems | 1596-B1 |
| EphB4 | Human | Fc fusion | Sino Biologics | 10235-H02H |

Certain peptide ligands and bicycle drug conjugates of the invention were tested in the above mentioned competition binding assay and the results are shown in Tables 10 to 12:

TABLE 10

SPR Binding Analysis with Selected Bicyclic Peptides and Bicycle Drug Conjugates of the Invention

| Bicycle/BDC No. | Human | | | | Mouse | | | | Rat | | | |
|---|---|---|---|---|---|---|---|---|---|---|---|---|
| | $K_D$ (nM) | $K_{off}$ (s−1) | $t_{1/2}$ (min) | $K_{on}$ (M−1s−1) | $K_D$ (nM) | $K_{off}$ (s−1) | $t_{1/2}$ (min) | $K_{on}$ (M−1s−1) | $K_D$ (nM) | $K_{off}$ (s−1) | $t_{1/2}$ (min) | $K_{on}$ (M−1s−1) |
| BCY6136 | 1.17 | 1.15E−03 | 10.0 | 9.86E+05 | 2.53 | 1.11E−03 | 10.4 | 4.37E+05 | 2.96 | 9.11E−04 | 12.6 | 3.07E+05 |
| BCY6173 | 0.73 | 1.24E−03 | 9.3 | 1.69E+06 | 2.95 | 1.14E−03 | 10.1 | 3.86E+05 | 1.10 | 9.60E−04 | 12.0 | 8.81E+05 |

Table 10 details binding affinities and kinetic parameters (Koff and Kon) for binding of selected Bicycle Drug Conjugates to human EphA2 determined using the SPR assay.

TABLE 11

SPR Binding Analysis with Selected Bicycle Drug Conjugates of the Invention with Human Eph Homologs

| BDC No. | EphA1 | EphA3 | EphA4 | EphA5 | EphA6 | EphA7 | EphB4 |
|---|---|---|---|---|---|---|---|
| BCY6136 | no binding @ 5 µM | no binding @ 5 µM | no binding @ 5 µM | no binding @ 25 µM | no binding @ 20 µM | no binding @ 20 µM | no binding @ 20 µM |
| BCY6173 | no binding @ 5 µM | no binding @ 5 µM | no binding @ 5 µM | no binding @ 25 µM | no binding @ 20 µM | no binding @ 20 µM | no binding @ 20 µM |

Table 11 illustrates binding results with four Bicycle Drug Conjugates (BCY6136 and BCY6173) in the SPR assay with closely related human Ephrin homologs. The results show that compounds of the invention exhibit no significant binding to closely related human homologs: EphA1, EphA3, EphA4, EphA5, EphA6, EphA7 and EphB4.

TABLE 12

SPR Binding Analysis with Selected Bicycle Drug Conjugates of the Invention with Mouse and Rat Eph Orthologs

| BDC No. | Mouse EphA3 | Mouse EphA4 | Rat EphA3 | Rat EphB1 |
|---|---|---|---|---|
| BCY6136 | no binding @ 20 µM | no binding @ 20 µM | no binding @ 20 µM | no binding @ 20 µM |
| BCY6173 | no binding @ 20 µM | no binding @ 20 µM | no binding @ 20 µM | no binding @ 20 µM |

The results in Table 12 show that certain Bicycle Drug Conjugates of the invention (BCY6136 and BCY6173) are also selective for mouse and rat EphA2 and exhibit no significant binding to closely related homologs: mouse EphA3 and EphA4; and rat EphA3 and EphB1.

Studies 3 and 7-23

In each of Studies 3 and 7-23, the following methodology was adopted for each study:

(a) Materials (i) Animals and Housing Condition

Animals

Species: Mus Musculus

Strain: Balb/c nude or CB17-SCID

Age: 6-8 weeks

Body weight: 18-22 g

Number of animals: 9-90 mice

Animal supplier: Shanghai Lingchang Biotechnology Experimental Animal Co. Limited Housing Condition The mice were kept in individual ventilation cages at constant temperature and humidity with 3-5 animals in each cage.

Temperature: 20-26° C.

Humidity 40-70%.

Cages: Made of polycarbonate. The size is 300 mm×180 mm×150 mm. The bedding material is corn cob, which is changed twice per week.

Diet: Animals had free access to irradiation sterilized dry granule food during the entire study period.

Water: Animals had free access to sterile drinking water.

Cage identification: The identification labels for each cage contained the following information: number of animals, sex, strain, the date received, treatment, study number, group number and the starting date of the treatment.

Animal identification: Animals were marked by ear coding.

(ii) Test and Positive Control Articles

| Number | Physical Description | Molecular Weight | Purity | Storage Condition |
|---|---|---|---|---|
| BCY6135 | Lyophilised powder | 4021 | 95.14% | Stored at −80° C. |
| BCY6136 | Lyophilised powder | 4402.23 | 97.5-98.6% | Stored at −80° C. |
| BCY6173 | Lyophilised powder | 4101.15 | 95.80% | Stored at −80° C. |
| BCY6174 | Lyophilised powder | 4537 | 99.50% | Stored at −80° C. |
| BCY6175 | Lyophilised powder | 4492.29 | 96.20% | Stored at −80° C. |
| BCY8245 | Lyophilised powder | 4173.85 | 99.30% | Stored at −80° C. |
| BCY8781 | Lyophilised powder | 4173.83 | 99.00% | Stored at −80° C. |
| ADC (MEDI-547)[1] | Solution (10.47 mg/ml concentration) | — | >99.00% | Stored at −80° C. |

[1]Full details of MEDI-547 (a fully human monoclonal antibody 1C1 (recognizing both human and murine EphA2) conjugated to MMAF via an mc linker) are described in Jackson et al (2008) Cancer Res 68, 9367-74.

(b) Experimental Methods and Procedures (i) Observations

All the procedures related to animal handling, care and the treatment in the study were performed according to the guidelines approved by the Institutional Animal Care and Use Committee (IACUC) of WuXi AppTec, following the guidance of the Association for Assessment and Accreditation of Laboratory Animal Care (AAALAC). At the time of routine monitoring, the animals were daily checked for any effects of tumor growth and treatments on normal behavior such as mobility, food and water consumption (by looking only), body weight gain/loss, eye/hair matting and any other abnormal effect as stated in the protocol. Death and observed clinical signs were recorded on the basis of the numbers of animals within each subset.

(ii) Tumor Measurements and the Endpoints

The major endpoint was to see if the tumor growth could be delayed or mice could be cured. Tumor volume was measured three times weekly in two dimensions using a caliper, and the volume was expressed in mm$^3$ using the formula: $V=0.5 \, a \times b^2$ where a and b are the long and short diameters of the tumor, respectively. The tumor size was then used for calculations of T/C value. The T/C value (in percent) is an indication of antitumor effectiveness; T and C are the mean volumes of the treated and control groups, respectively, on a given day.

TGI was calculated for each group using the formula: TGI $(\%)=[1-(T_i-T_0)/(V_i-V_0)]\times 100$; $T_i$ is the average tumor volume of a treatment group on a given day, $T_0$ is the average tumor volume of the treatment group on the day of treatment start, $V_i$ is the average tumor volume of the vehicle control group on the same day with $T_i$ and $V_0$ is the average tumor volume of the vehicle group on the day of treatment start.

(iii) Sample Collection

At the end of study the tumors of all groups were collected for FFPE.

(iv) Statistical Analysis

Summary statistics, including mean and the standard error of the mean (SEM), are provided for the tumor volume of each group at each time point.

Statistical analysis of difference in tumor volume among the groups was conducted on the data obtained at the best therapeutic time point after the final dose.

A one-way ANOVA was performed to compare tumor volume among groups, and when a significant F-statistics (a ratio of treatment variance to the error variance) was obtained, comparisons between groups were carried out with Games-Howell test. All data were analyzed using GraphPad Prism 5.0. $P<0.05$ was considered to be statistically significant.

Study 3: Investigation of Association Between Copy Number Variation (CNV) and Gene Expression for EphA2 from Multiple Tumour Types Methods 1. Select all studies in cBioPortal (http://www.cboportal.org/) and search for EPHA2.
    (a) Remove provisional studies.
    (b) Deselect studies with overlapping samples to prevent sample bias (based on warning in cBioPortal)—always keep PanCancer study if this is an option.
    (c) Studies selected for analysis (Table 13).

TABLE 13

Studies analysed from cBioPortal and units in study

| Study Name | Units |
| --- | --- |
| Breast Invasive Carcinoma (TCGA, PanCancer Atlas) | mRNA Expression Batch Normalized/Merged from Illumina HiSeq_RNASeqV2 syn4976369 |
| Lung Squamous Cell Carcinoma (TCGA, PanCancer Atlas) | mRNA Expression Batch Normalized/Merged from Illumina HiSeq_RNASeqV2 syn4976369 |
| Kidney Renal Papillary Cell Carcinoma (TCGA, PanCancer Atlas) | mRNA Expression, RSEM (Batch normalized from Illumina HiSeq_RNASeqV2) |
| Kidney Renal Clear Cell Carcinoma (TCGA, PanCancer Atlas) | mRNA Expression, RSEM (Batch normalized from Illumina HiSeq_RNASeqV2) |
| Colon Adenocarcinoma (TCGA, PanCancer Atlas) | RSEM (Batch normalized from Illumina HiSeq_RNASeqV2) |
| Head and Neck Squamous Cell Carcinoma (TCGA, PanCancer Atlas) | mRNA Expression, RSEM (Batch normalized from Illumina HiSeq_RNASeqV2) |
| Bladder Urothelial Carcinoma (TCGA, PanCancer Atlas) | RSEM (Batch normalized from Illumina HiSeq_RNASeqV2) |
| Uveal Melanoma (TCGA, PanCancer Atlas) | mRNA Expression Batch Normalized/Merged from Illumina HiSeq_RNASeqV2 syn4976369 |
| Lung Adenocarcinoma (TCGA, PanCancer Atlas) | mRNA Expression, RSEM (Batch normalized from Illumina HiSeq_RNASeqV2) |
| Ovarian Serous Cystadenocarcinoma (TCGA, PanCancer Atlas) | mRNA Expression Batch Normalized/Merged from Illumina HiSeq_RNASeqV2 syn4976369 |
| Breast Cancer (METABRIC, Nature 2012 & Nat Commun 2016) | mRNA expression (microarray) |
| Mesothelioma (TCGA, PanCancer Atlas) | mRNA Expression Batch Normalized/Merged from Illumina HiSeq_RNASeqV2 syn4976369 |
| Colorectal Adenocarcinoma (TCGA, Nature 2012) | RNA Seq RPKM |
| Cervical Squamous Cell Carcinoma (TCGA, PanCancer Atlas) | RSEM (Batch normalized from Illumina HiSeq_RNASeqV2) |
| Sarcoma (TCGA, PanCancer Atlas) | mRNA Expression Batch Normalized/Merged from Illumina HiSeq_RNASeqV2 syn4976369 |
| Cancer Cell Line Encyclopedia (Novartis/Broad, Nature 2012) | mRNA expression (microarray) |
| Rectum Adenocarcinoma (TCGA, PanCancer Atlas) | mRNA Expression Batch Normalized/Merged from Illumina HiSeq_RNASeqV2 syn4976369 |
| Liver Hepatocellular Carcinoma (TCGA, PanCancer Atlas) | EPHA2: mRNA Expression, RSEM (Batch normalized from Illumina HiSeq_RNASeqV2) |
| Stomach Adenocarcinoma (TCGA, PanCancer Atlas) | mRNA Expression Batch Normalized/Merged from Illumina HiSeq_RNASeqV2 syn4976369 |
| Uterine Corpus Endometrial Carcinoma (TCGA, PanCancer Atlas) | mRNA Expression Batch Normalized/Merged from Illumina HiSeq_RNASeqV2 syn4976369 |
| Skin Cutaneous Melanoma (TCGA, PanCancer Atlas) | mRNA Expression Batch Normalized/Merged from Illumina HiSeq_RNASeqV2 syn4976369 |
| Prostate Adenocarcinoma (TCGA, PanCancer Atlas) | mRNA Expression, RSEM (Batch normalized from Illumina HiSeq_RNASeqV2) |
| Kidney Chromophobe (TCGA, PanCancer Atlas) | mRNA Expression, RSEM (Batch normalized from Illumina HiSeq_RNASeqV2) |

TABLE 13-continued

Studies analysed from cBioPortal and units in study

| Study Name | Units |
| --- | --- |
| Pediatric Wilms' Tumor (TARGET, 2018) | Epha2: mRNA expression (RNA-Seq RPKM) |
| Pheochromocytoma and Paraganglioma (TCGA, PanCancer Atlas) | mRNA Expression Batch Normalized/Merged from Illumina HiSeq_RNASeqV2 syn4976369 |
| Thyroid Carcinoma (TCGA, PanCancer Atlas) | mRNA Expression Batch Normalized/Merged from Illumina HiSeq_RNASeqV2 syn4976369 |
| Esophageal Adenocarcinoma (TCGA, PanCancer Atlas) | RSEM (Batch normalized from Illumina HiSeq_RNASeqV2) |
| Cholangiocarcinoma (TCGA, PanCancer Atlas) | RSEM (Batch normalized from Illumina HiSeq_RNASeqV2) |
| Brain Lower Grade Glioma (TCGA, PanCancer Atlas) | RSEM (Batch normalized from Illumina HiSeq_RNASeqV2) |
| Thymoma (TCGA, PanCancer Atlas) | mRNA Expression Batch Normalized/Merged from Illumina HiSeq_RNASeqV2 syn4976369 |
| Pediatric Acute Lymphoid Leukemia - Phase II (TARGET, 2018) | Epha2: mRNA expression (RNA-Seq RPKM) |
| Diffuse Large B-Cell Lymphoma (TCGA, PanCancer Atlas) | mRNA Expression, RSEM (Batch normalized from Illumina HiSeq_RNASeqV2) |
| Glioblastoma Multiforme (TCGA, PanCancer Atlas) | mRNA Expression, RSEM (Batch normalized from Illumina HiSeq_RNASeqV2) |
| Metastatic Prostate Cancer, SU2C/PCF Dream Team (Robinson et al., Cell 2015) | mRNA expression/capture (RNA Seq RPKM) |
| Acute Myeloid Leukemia (TCGA, PanCancer Atlas) | mRNA Expression, RSEM (Batch normalized from Illumina HiSeq_RNASeqV2) |
| Testicular Germ Cell Tumors (TCGA, PanCancer Atlas) | mRNA Expression Batch Normalized/Merged from Illumina HiSeq_RNASeqV2 syn4976369 |
| Adrenocortical Carcinoma (TCGA, PanCancer Atlas) | RSEM (Batch normalized from Illumina HiSeq_RNASeqV2) |
| Uterine Carcinosarcoma (TCGA, PanCancer Atlas) | mRNA Expression Batch Normalized/Merged from Illumina HiSeq_RNASeqV2 syn4976369 |
| Pancreatic Adenocarcinoma (TCGA, PanCancer Atlas) | mRNA Expression Batch Normalized/Merged from Illumina HiSeq_RNASeqV2 syn4976369 |
| Prostate Adenocarcinoma (MSKCC, Cancer Cell 2010) | mRNA Expression |
| Prostate Adenocarcinoma (Fred Hutchinson CRC, Nat Med 2016) | mRNA expression |

2. Export CNV and RNA expression data from cBioPortal.
3. Test if CNVs are statistically significantly associated with changes in mRNA expression for EphA2 (log 2 not applied).
   (a) Run non-parametric Kruskal-Wallis test in GraphPad Prism (7.04) and R/R studio (threshold for significance: p<0.01).
      (i) GraphPad Prism: set up column table, run non-parametric test with no matching or pairing and do not assume Gaussian distribution.
      (ii) Packages used in R:
         1. XLConnect
         2. dplyr
         3. Kruskal-Wallis Rank Sum Test: Kruskal.test.
4. Adjust for multiple comparisons (include all possible comparisons even if n=1 within a group) in R/Rstudio using Dunn's test (threshold for significance: p<0.025).
   (a) dunn.test with multiple comparison method="bonferonni".

Results

The results are shown in Table 14 below. Across 41 publicly available datasets compiled in cBioPortal that report both Copy Number Variation (CNV) and mRNA gene expression for EphA2, there are numerous cancer types where cases have been reported with EphA2 shallow-deletions (<2 copies). Although less common, in these same cancer types a subset of tumors harbored EphA2 deep deletions (>1 copy loss or biallelic loss), EphA2 gains (2-3 copies) or EphA2 amplifications (>3 copies). Indications where >33% of tumors had either shallow-deletions or deep deletions in EphA2 included: kidney chromophobe, cholangiocarcinoma, pheochromocytoma and paraganglioma, lung squamous cancer, breast, rectum, brain lower grade glioma, liver, adrenocortical carcinoma, mesothelioma, esophageal adenocarcinoma and colon cancer. In contrast, there were no studies where >33% of samples had either gains or amplification in EphA2. Taken together these results demonstrate that deletions in EphA2 DNA are found across a variety of indications.

Approximately one third of all samples analyzed in the 41 studies harbored EphA2 CNVs. Based on this high percentage of CNVs across studies, and the high percentage of shallow deletions within specific tumor types, statistical testing was performed to identify possible associations between copy number changes and RNA expression. Tumors per indication were allocated to 1 of 5 classes:
   a) Deep deletion;
   b) Shallow deletion;
   c) Diploid;
   d) Gain; or
   e) Amplification.

Kruskall-Wallis testing was then performed to detect if the distributions of mRNA expression values per classes differed between classes (P<0.01). For those TCGA data sets with P<0.01 and to identify which classes were different to one another post-hoc testing was performed by calculating Z-statistics with adjusted P-values calculated (Bonferroni).

For simplicity of interpretation pair-wise comparisons vs. diploid per indication were reviewed (although all pair-wise P-values were calculated). 19/41 of these studies had a Kruskall-Wallis p-value of <0.01 demonstrating that copy number is statistically significantly associated with RNA expression. Of these 19 studies, 17 of them had a Bonferroni adjusted P<0.025 for Diploid vs. Shallow Deletion indicating an association of decreased EphA2 mRNA expression with decreased EphA2 copy number. Only 2 of these 19 studies had a Bonferroni adjusted P<0.025 for Diploid vs. Gain and both were breast cancer studies. Furthermore, one of these breast cancer studies (Breast Invasive Carcinoma (TCGA, PanCancer Atlas)) had a Bonferroni adjusted P<0.025 for both Diploid vs. Shallow Deletion and Diploid vs. Gain suggesting that copy number alterations may have a strong impact on EphA2 RNA expression in breast cancer.

The central dogma of genetics suggests that reduced copy number in EphA2 lead to reduced RNA and protein expression. Therefore, the observed associations between copy number loss of EphA2 and reduced mRNA expression in a variety of tumor types suggest that EphA2 protein expression may also be reduced. Similarly, copy number gains of EphA2 in breast cancer that were associated with increased mRNA expression may also suggest increased EphA2 protein expression. Moreover, higher EphA2 protein expression (measured by FACS) is associated with increased efficacy of certain EphA2 bicyclic drug conjugates of the invention (measured by tumor volume) in preclinical in vivo models. Taken together if copy number alterations that are associated with mRNA expression changes do predict protein expression levels then patients with tumors containing copy number deletions of EphA2 may be less likely to respond to EphA2 bicyclic drug conjugates of the invention. Similarly, if patients with tumor copy number gains in EphA2 (e.g. breast cancer) it is possible that these patients would be more likely to respond to EphA2 bicyclic drug conjugates of the invention. Therefore, if patients were stratified by EphA2 copy number status, then this information could be used to both exclude and select patients for treatment with EphA2 bicyclic drug conjugates of the invention to increase efficacy.

TABLE 14

Results of Investigation of Association between Copy Number Variation (CNV) and gene expression for EphA2

| Study name | Units | Number of samples/group (n = X) | | | | | Kruskal-wallis test | |
|---|---|---|---|---|---|---|---|---|
| | | Deep deletion | Shallow deletion | Diploid | Gain | Amplification | Kruskal-wallis statstic | p-value |
| Breast Invasive Carcinoma (TCGA, PanCancer Atlas) | mRNA Expression Batch Normalized/ Merged from Illumina HiSeq_RNASeqV2 syn4976369 | 5 | 415 | 511 | 61 | 2 | 80.816 | <2.2e−16 |
| Lung Squamous Cell Carcinoma (TCGA, PanCancer Atlas) | mRNA Expression Batch Normalized/ Merged from Illumina HiSeq_RNASeqV2 syn4976369 | 3 | 207 | 201 | 55 | 0 | 52.942 | 1.89E−11 |
| Kidney Renal Papillary Cell Carcinoma (TCGA, PanCancer Atlas) | mRNA Expression, RSEM (Batch normalized from Illumina HiSeq_RNASeqV2) | 1 | 48 | 224 | 0 | 1 | 42.161 | 3.71E−09 |
| Kidney Renal Clear Cell Carcinoma (TCGA, PanCancer Atlas) | mRNA Expression, RSEM (Batch normalized from Illumina HiSeq_RNASeqV2) | 0 | 69 | 278 | 5 | 0 | 38.342 | 4.72E−09 |
| Colon Adenocarcinoma (TCGA, PanCancer Atlas) | RSEM (Batch normalized from Illumina HiSeq_RNASeqV2) | 3 | 132 | 245 | 8 | 0 | 35.397 | 1.00E−07 |
| Head and Neck Squamous cell Carcinoma (TCGA, PanCancer Atlas) | mRNA Expression, RSEM (Batch normalized from Illumina HiSeq_RNASeqV2) | 3 | 86 | 345 | 54 | 0 | 32.72 | 3.69E−07 |

TABLE 14-continued

Results of Investigation of Association between Copy Number Variation (CNV) and gene expression for EphA2

| Cancer Type | Data Type | | | | | | |
|---|---|---|---|---|---|---|---|
| Bladder Urothelial Carcinoma (TCGA, PanCancer Atlas) | RSEM (Batch normalized from Illumina HiSeq_RNASeqV2) | 0 | 73 | 245 | 80 | 4 | 28.906 | 2.34E−06 |
| Uveal Melanoma (TCGA, PanCancer Atlas) | mRNA Expression Batch Normalized/ Merged from Illumina HiSeq_RNASeqV2 syn4976369 | 0 | 24 | 56 | 0 | 0 | 21.051 | 4.47E−06 |
| Lung Adenocarcinoma (TCGA, PanCancer Atlas) | mRNA Expression, RSEM (Batch normalized from Illumina HiSeq_RNASeqV2) | 1 | 115 | 263 | 121 | 3 | 28.874 | 8.29E−06 |
| Ovarian Serous Cystadenocarcinoma (TCGA, PanCancer Atlas) | mRNA Expression Batch Normalized/ Merged from Illumina HiSeq_RNASeqV2 syn4976369 | 0 | 59 | 78 | 60 | 4 | 25.349 | 1.31E−05 |
| Breast Cancer (METABRIC, Nature 2012 & Nat Commun 2016) | mRNA expression (microarray) | 1 | 491 | 1349 | 25 | 0 | 23.875 | 2.65E−05 |
| Mesothelioma (TCGA, PanCancer Atlas) | mRNA Expression Batch Normalized/ Merged from Illumina HiSeq_RNASeqV2 syn4976369 | 0 | 29 | 50 | 3 | 0 | 18.866 | 8.00E−05 |
| Colorectal Adenocarcinoma (TCGA, Nature 2012) | RNA Seq RPKM | 0 | 53 | 138 | 2 | 0 | 18.847 | 8.08E−05 |
| Cervical Squamous Cell Carcinoma (TCGA, PanCancer Atlas) | RSEM (Batch normalized from Illumina HiSeq_RNASeqV2) | 1 | 31 | 167 | 76 | 0 | 19.435 | 2.22E−04 |
| Sarcoma (TCGA, PanCancer Atlas) | mRNA Expression Batch Normalized/ Merged from Illumina HiSeq_RNASeqV2 syn4976369 | 0 | 43 | 113 | 70 | 4 | 19.389 | 2.27E−04 |
| Cancer Cell Line Encyclopedia (Novartis/Broad, Nature 2012) | mRNA expression (microarray) | 17 | 279 | 418 | 150 | 13 | 20.977 | 0.00032 |
| Rectum Adenocarcinoma (TCGA, PanCancer Atlas) | mRNA Expression Batch Normalized/ Merged from Illumina HiSeq_RNASeqV2 syn4976369 | 1 | 54 | 78 | 3 | 0 | 18.215 | 0.0003971 |
| Liver Hepatocellular Carcinoma (TCGA, PanCancer Atlas) | EPHA2: mRNA Expression, RSEM (Batch normalized from Illumina HiSeq_RNASeqV2) | 1 | 130 | 194 | 21 | 2 | 15.514 | 0.003745 |

TABLE 14-continued

Results of Investigation of Association between Copy Number Variation (CNV) and gene expression for EphA2

| | | | | | | | | |
|---|---|---|---|---|---|---|---|---|
| Stomach Adenocarcinoma (TCGA, PanCancer Atlas) | mRNA Expression Batch Normalized/ Merged from Illumina HiSeq_RNASeqV2 syn4976369 | 2 | 90 | 264 | 44 | 7 | 13.966 | 0.007404 |
| Uterine Corpus Endometrial Carcinoma (TCGA, PanCancer Atlas) | mRNA Expression Batch Normalized/ Merged from Illumina HiSeq_RNASeqV2 syn4976369 | 3 | 61 | 395 | 43 | 5 | 12.916 | 0.0117 |
| Skin Cutaneous Melanoma (TCGA, PanCancer Atlas) | mRNA Expression Batch Normalized/ Merged from Illumina HiSeq_RNASeqV2 syn4976369 | 2 | 70 | 216 | 72 | 3 | 12.242 | 0.01564 |
| Prostate Adenocarcinoma (TCGA, PanCancer Atlas) | mRNA Expression, RSEM (Batch normalized from Illumina HiSeq_RNASeqV2) | 0 | 44 | 438 | 4 | 1 | 10.112 | 0.01764 |
| Kidney Chromophobe (TCGA, PanCancer Atlas) | mRNA Expression, RSEM (Batch normalized from Illumina HiSeq_RNASeqV2) | 0 | 52 | 12 | 1 | 0 | 7.8781 | 0.01947 |
| Pediatric Wilms' Tumor (TARGET, 2018) | Epha2: mRNA expression (RNA-Seq RPKM) | 0 | 22 | 74 | 5 | 0 | 7.4912 | 0.02362 |
| Pheochromocytoma and Paraganglioma (TCGA, PanCancer Atlas) | mRNA Expression Batch Normalized/ Merged from Illumina HiSeq_RNASeqV2 syn4976369 | 4 | 96 | 60 | 1 | 0 | 8.8074 | 0.03196 |
| Thyroid Carcinoma (TCGA, PanCancer Atlas) | mRNA Expression Batch Normalized/ Merged from Illumina HiSeq_RNASeqV2 syn4976369 | 0 | 4 | 474 | 2 | 0 | 5.1773 | 0.08 |
| Esophageal Adenocarcinoma (TCGA, PanCancer Atlas) | RSEM (Batch normalized from Illumina HiSeq_RNASeqV2) | 1 | 64 | 83 | 32 | 1 | 7.6886 | 0.1037 |
| Cholangiocarcinoma (TCGA, PanCancer Atlas) | RSEM (Batch normalized from Illumina HiSeq_RNASeqV2) | 2 | 27 | 7 | 0 | 0 | 4.1691 | 0.1244 |
| Brain Lower Grade Glioma (TCGA, PanCancer Atlas) | RSEM (Batch normalized from Illumina HiSeq_RNASeqV2) | 0 | 191 | 303 | 13 | 0 | 4.0473 | 0.1322 |

TABLE 14-continued

Results of Investigation of Association between Copy Number Variation (CNV) and gene expression for EphA2

| Cancer | Data | | | | | | | |
|---|---|---|---|---|---|---|---|---|
| Thymoma (TCGA, PanCancer Atlas) | mRNA Expression Batch Normalized/ Merged from Illumina HiSeq_RNASeqV2 syn4976369 | 0 | 8 | 110 | 1 | 0 | 4.0322 | 1.33E−01 |
| Pediatric Acute Lymphoid Leukemia-Phase II (TARGET, 2018) | Epha2: mRNA expression (RNA-Seq RPKM) | 1 | 6 | 70 | 4 | 0 | 5.5309 | 0.1368 |
| Diffuse Large B-Cell Lymphoma (TCGA, PanCancer Atlas) | mRNA Expression, RSEM (Batch normalized from Illumina HiSeq_RNASeqV2) | 0 | 4 | 33 | 0 | 0 | 1.744 | 0.1866 |
| Glioblastoma Multiforme (TCGA, PanCancer Atlas) | mRNA Expression, RSEM (Batch normalized from Illumina HiSeq_RNASeqV2) | 0 | 13 | 104 | 28 | 0 | 2.9376 | 0.2302 |
| Metastatic Prostate Cancer, SU2C/PCF Dream Team (Robinson et al., Cell 2015) | mRNA expression/ capture (RNA Seq RPKM) | 2 | 21 | 87 | 7 | 0 | 4.069 | 0.254 |
| Acute Myeloid Leukemia (TCGA, PanCancer Atlas) | mRNA Expression, RSEM (Batch normalized from Illumina HiSeq_RNASeqV2) | 0 | 1 | 160 | 4 | 0 | 2.4016 | 0.301 |
| Testicular Germ Cell Tumors (TCGA, PanCancer Atlas) | mRNA Expression Batch Normalized/ Merged from Illumina HiSeq_RNASeqV2 syn4976369 | 1 | 29 | 92 | 22 | 0 | 3.3144 | 0.3456 |
| Adrenocortical Carcinoma (TCGA, PanCancer Atlas) | RSEM (Batch normalized from Illumina HiSeq_RNASeqV2) | 0 | 28 | 47 | 1 | 0 | 2.0003 | 0.3678 |
| Uterine Carcinosarcoma (TCGA, PanCancer Atlas) | mRNA Expression Batch Normalized/ Merged from Illumina HiSeq_RNASeqV2 syn4976369 | 0 | 16 | 22 | 16 | 2 | 2.44 | 0.4862 |
| Pancreatic Adenocarcinoma (TCGA, PanCancer Atlas) | mRNA Expression Batch Normalized/ Merged from Illumina HiSeq_RNASeqV2 syn4976369 | 2 | 50 | 106 | 9 | 1 | 3.3833 | 4.96E−01 |
| Prostate Adenocarcinoma (MSKCC, Cancer Cell 2010) | mRNA Expression | 0 | 5 | 77 | 3 | 0 | 1.3139 | 0.5184 |

TABLE 14-continued

Results of Investigation of Association between Copy Number Variation (CNV) and gene expression for EphA2

| | | | | | | | |
|---|---|---|---|---|---|---|---|
| Prostate Adenocarcinoma (Fred Hutchinson CRC, Nat Med 2016) | mRNA expression | 0 | 39 | 84 | 10 | 0 | 0.028351 0.9859 |

| | | Pairwise comparison, Z statistic (adjusted p-value), Bonferonni | | | |
|---|---|---|---|---|---|
| Study name | Units | Deep Deletion-Diploid | Diploid-Shallow deletion | Diploid-Gain | Amplification-Diploid |
| Breast Invasive Carcinoma (TCGA, PanCancer Atlas) | mRNA Expression Batch Normalized/ Merged from Illumina HiSeq_RNASeqV2 syn4976369 | 0.176118 (1.0000) | 6.460580 (0.0000)* | −4.603180 (0.0000)* | 0.713978 (1.0000) |
| Lung Squamous Cell Carcinoma (TCGA, PanCancer Atlas) | mRNA Expression Batch Normalized/ Merged from Illumina HiSeq_RNASeqV2 syn4976369 | −1.584610 (0.3392) | 6.786501 (0.0000)* | −0.019607 (1.0000) | N/A |
| Kidney Renal Papillary Cell Carcinoma (TCGA, PanCancer Atlas) | mRNA Expression, RSEM (Batch normalized from Illumina HiSeq_RNASeqV2) | −1.586207 (0.3381) | 6.097375 (0.0000)* | N/A | 1.549107 (0.3641) |
| Kidney Renal Clear Cell Carcinoma (TCGA, PanCancer Atlas) | mRNA Expression, RSEM (Batch normalized from Illumina HiSeq_RNASeqV2) | N/A | 6.133219 (0.0000)* | −0.487059 (0.9393) | N/A |
| Colon Adenocarcinoma (TCGA, PanCancer Atlas) | RSEM (Batch normalized from Illumina HiSeq_RNASeqV2) | −2.158194 (0.0927) | 5.670600 (0.0000)* | 0.781046 (1.0000) | N/A |
| Head and Neck Squamous cell Carcinoma (TCGA, PanCancer Atlas) | mRNA Expression, RSEM (Batch normalized from Illumina HiSeq_RNASeqV2) | −2.444914 (0.0435) | 4.680789 (0.0000)* | −1.530670 (0.3776) | N/A |
| Bladder Urothelial Carcinoma (TCGA, PanCancer Atlas) | RSEM (Batch normalized from Illumina HiSeq_RNASeqV2) | N/A | 5.203251 (0.0000)* | 0.211744 (1.0000) | 0.581704 (1.0000) |
| Uveal Melanoma (TCGA, PanCancer Atlas) | mRNA Expression Batch Normalized/ Merged from Illumina HiSeq_RNASeqV2 syn4976369 | N/A | 4.588095 (0.0000)* | N/A | N/A |
| Lung Adenocarcinoma (TCGA, PanCancer Atlas) | mRNA Expression, RSEM (Batch normalized from Illumina HiSeq_RNASeqV2) | −0.690460 (1.0000) | 4.280100 (0.0001)* | −0.626707 (1.0000) | 2.276458 (0.1141) |

TABLE 14-continued

Results of Investigation of Association between Copy Number Variation (CNV) and gene expression for EphA2

| | | | | | |
|---|---|---|---|---|---|
| Ovarian Serous Cystadenocarcinoma (TCGA, PanCancer Atlas) | mRNA Expression Batch Normalized/ Merged from Illumina HiSeq_RNASeqV2 syn4976369 | N/A | 4.390097 (0.0000)* | −0.239249 (1.0000) | 0.240543 (1.0000) |
| Breast Cancer (METABRIC, Nature 2012 & Nat Commun 2016) | mRNA expression (microarray) | 0.568937 (1.0000) | 2.274564 (0.0688) | −4.115288 (0.0001)* | N/A |
| Mesothelioma (TCGA, PanCancer Atlas) | mRNA Expression Batch Normalized/ Merged from Illumina HiSeq_RNASeqV2 syn4976369 | N/A | 4.319425 (0.0000)* | 0.170478 (1.0000) | N/A |
| Colorectal Adenocarcinoma (TCGA, Nature 2012) | RNA Seq RPKM | N/A | 4.298092 (0.0000)* | −0.338975 (1.0000) | N/A |
| Cervical Squamous Cell Carcinoma (TCGA, PanCancer Atlas) | RSEM (Batch normalized from Illumina HiSeq_RNASeqV2) | −1.618248 (0.3168) | 3.42960 (0.0018)* | −1.446339 (0.4442) | N/A |
| Sarcoma (TCGA, PanCancer Atlas) | mRNA Expression Batch Normalized/ Merged from Illumina HiSeq_RNASeqV2 syn4976369 | N/A | 3.666949 (0.0007)* | −0.852454 (1.0000) | 0.953027 (1.0000) |
| Cancer Cell Line Encyclopedia (Novartis/Broad, Nature 2012) | mRNA expression (microarray) | −2.084879 (0.1854) | −3.615935 (0.0015)* | −2.007004 (0.2237) | −0.108880 (1.0000) |
| Rectum Adenocarcinoma (TCGA, PanCancer Atlas) | mRNA Expression Batch Normalized/ Merged from Illumina HiSeq_RNASeqV2 syn4976369 | −1.926519 (0.1621) | 3.877166 (0.0003)* | 1.167400 (0.7291) | N/A |
| Liver Hepatocellular Carcinoma (TCGA, PanCancer Atlas) | EPHA2: mRNA Expression, RSEM (Batch normalized from Illumina HiSeq_RNASeqV2) | 0.302341 (1.0000) | 3.697248 (0.0011)* | −0.336659 (1.0000) | 0.454454 (1.0000) |
| Stomach Adenocarcinoma (TCGA, PanCancer Atlas) | mRNA Expression Batch Normalized/ Merged from Illumina HiSeq_RNASeqV2 syn4976369 | −2.072978 (0.1909) | 1.606072 (0.5413) | −1.750466 (0.4002) | 1.602806 (0.5449) |
| Uterine Corpus Endometrial Carcinoma (TCGA, PanCancer Atlas) | mRNA Expression Batch Normalized/ Merged from Illumina HiSeq_RNASeqV2 syn4976369 | −1.905863 (0.2833) | 1.039307 (1.0000) | −1.597383 (0.5509) | 2.268798 (0.1164) |

TABLE 14-continued

Results of Investigation of Association between Copy Number Variation (CNV) and gene expression for EphA2

| Cancer | Data Type | Col1 | Col2 | Col3 | Col4 |
|---|---|---|---|---|---|
| Skin Cutaneous Melanoma (TCGA, PanCancer Atlas) | mRNA Expression Batch Normalized/ Merged from Illumina HiSeq_RNASeqV2 syn4976369 | 1.094526 (1.0000) | 2.674493 (0.0374) | 0.095966 (1.0000) | 1.692628 (0.4526) |
| Prostate Adenocarcinoma (TCGA, PanCancer Atlas) | mRNA Expression, RSEM (Batch normalized from Illumina HiSeq_RNASeqV2) | N/A | 2.905502 (0.0110)* | 1.374609 (0.5078) | −0.082790 (1.0000) |
| Kidney Chromophobe (TCGA, PanCancer Atlas) | mRNA Expression, RSEM (Batch normalized from Illumina HiSeq_RNASeqV2) | N/A | 2.498340 (0.0187)* | 1.863169 (0.0937) | N/A |
| Pediatric Wilms' Tumor (TARGET, 2018) | Epha2: mRNA expression (RNA-Seq RPKM) | N/A | 2.690766 (0.0107)* | −0.173274 (1.0000) | N/A |
| Pheochromocytoma and Paraganglioma (TCGA, PanCancer Atlas) | mRNA Expression Batch Normalized/ Merged from Illumina HiSeq_RNASeqV2 syn4976369 | −1.411567 (0.4742) | 2.201344 (0.0831) | 1.946134 (0.1549) | N/A |
| Thyroid Carcinoma (TCGA, PanCancer Atlas) | mRNA Expression Batch Normalized/ Merged from Illumina HiSeq_RNASeqV2 syn4976369 | N/A | 2.221884 (0.0394) | 0.503577 (0.9218) | N/A |
| Esophageal Adenocarcinoma (TCGA, PanCancer Atlas) | RSEM (Batch normalized from Illumina HiSeq_RNASeqV2) | −1.462679 (0.7178) | 0.910990 (1.0000) | −1.682311 (0.4625) | −0.362298 (1.0000) |
| Cholangiocarcinoma (TCGA, PanCancer Atlas) | RSEM (Batch normalized from Illumina HiSeq_RNASeqV2) | −2.037840 (0.0623) | 0.972100 (0.4965) | N/A | N/A |
| Brain Lower Grade Glioma (TCGA, PanCancer Atlas) | RSEM (Batch normalized from Illumina HiSeq_RNASeqV2) | N/A | 0.722383 (0.7051) | −1.771514 (0.1147) | N/A |
| Thymoma (TCGA, PanCancer Atlas) | mRNA Expression Batch Normalized/ Merged from Illumina HiSeq_RNASeqV2 syn4976369 | N/A | 1.982334 (0.0712) | 0.369115 (1.0000) | N/A |
| Pediatric Acute Lymphoid Leukemia- Phase II (TARGET, 2018) | Epha2: mRNA expression (RNA-Seq RPKM) | 1.437404 (0.4518) | −0.805100 (1.0000) | 1.607586 (0.3238) | N/A |
| Diffuse Large B- Cell Lymphoma (TCGA, PanCancer Atlas) | mRNA Expression, RSEM (Batch normalized from Illumina HiSeq_RNASeqV2) | N/A | 1.320613 (0.0933) | N/A | N/A |

TABLE 14-continued

Results of Investigation of Association between Copy Number Variation (CNV) and gene expression for EphA2

| | | | | | |
|---|---|---|---|---|---|
| Glioblastoma Multiforme (TCGA, PanCancer Atlas) | mRNA Expression, RSEM (Batch normalized from Illumina HiSeq_RNASeqV2) | N/A | 1.428778 (0.2296) | −0.716110 (0.7109) | N/A |
| Metastatic Prostate Cancer, SU2C/PCF Dream Team (Robinson et al., Cell 2015) | mRNA expression/ capture (RNA Seq RPKM) | −1.812613 (0.2097) | 0.992571 (0.9628) | 0.314089 (1.0000) | N/A |
| Acute Myeloid Leukemia (TCGA, PanCancer Atlas) | mRNA Expression, RSEM (Batch normalized from Illumina HiSeq_RNASeqV2) | N/A | −1.539142 (0.1857) | −0.199532 (1.0000) | N/A |
| Testicular Germ Cell Tumors (TCGA, PanCancer Atlas) | mRNA Expression Batch Normalized/ Merged from Illumina HiSeq_RNASeqV2 syn4976369 | 0.574846 (1.0000) | −0.443110 (1.0000) | −1.751161 (0.2398) | N/A |
| Adrenocortical Carcinoma (TCGA, PanCancer Atlas) | RSEM (Batch normalized from Illumina HiSeq_RNASeqV2) | N/A | 1.346397 (0.2673) | 0.550103 (0.8734) | N/A |
| Uterine Carcinosarcoma (TCGA, PanCancer Atlas) | mRNA Expression Batch Normalized/ Merged from Illumina HiSeq_RNASeqV2 syn4976369 | N/A | 0.476071 (1.0000) | −0.550292 (1.0000) | 1.215102 (0.6730) |
| Pancreatic Adenocarcinoma (TCGA, PanCancer Atlas) | mRNA Expression Batch Normalized/ Merged from Illumina HiSeq_RNASeqV2 syn4976369 | −1.195082 (1.0000) | 0.159442 (1.0000) | −0.602558 (1.0000) | 1.217697 (1.0000) |
| Prostate Adenocarcinoma (MSKCC, Cancer Cell 2010) | mRNA Expression | N/A | −0.406579 (1.0000) | −1.089948 (0.4136) | N/A |
| Prostate Adenocarcinoma (Fred Hutchinson CRC, Nat Med 2016) | mRNA expression | N/A | 0.160404 (1.0000) | 0.079785 (1.0000) | N/A |

Study 4: In Vivo Efficacy of BCY6136 in CDX Xenograft Models

The study evaluated the therapeutic efficacy of BCY6136 in three Cancer Cell Line Derived (CDX) models: the HT1080 fibrosarcoma line, the MDA-MB-231 triple negative breast cancer line and the NCI-H1975 non-small cell lung cancer (NSCLC) line.

(a) Experimental Method

Balb/c mice were inoculated subcutaneously with tumour cells at the right flank and drug treatment started when the average tumour volume reached between 150 and 200 mm³. Tumour measurements and statistical analysis were performed as described above. Tumour bearing animals were treated once weekly with BCY6136 or vehicle.

(b) Discussion

Figure 4:
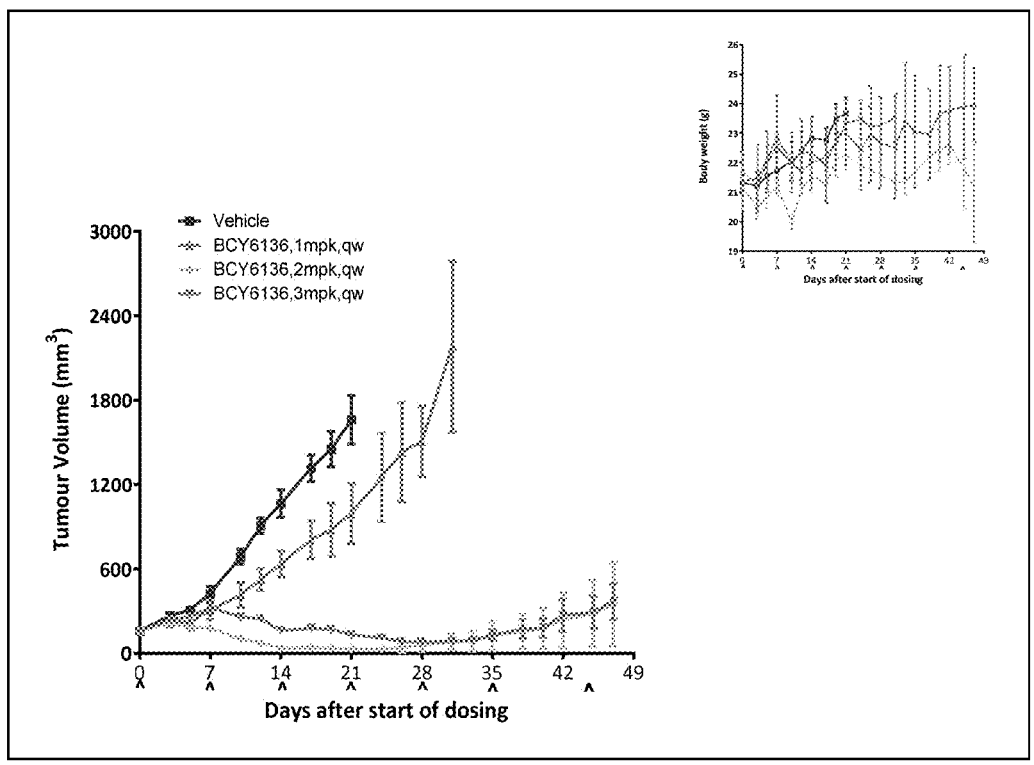
FIG. 4: Plot of mean tumour volume versus time for BCY6136 in MDA-MB-231 xenograft mice. Doses (1, 2 and 3 mg/kg) were administered on day 0, 7, 14, 21, 28, 35 and 45. Body weight changes during treatment indicative of tumour burden, drug-associated toxicology and overall animal health are illustrated in the top right inset.
Figure 5:
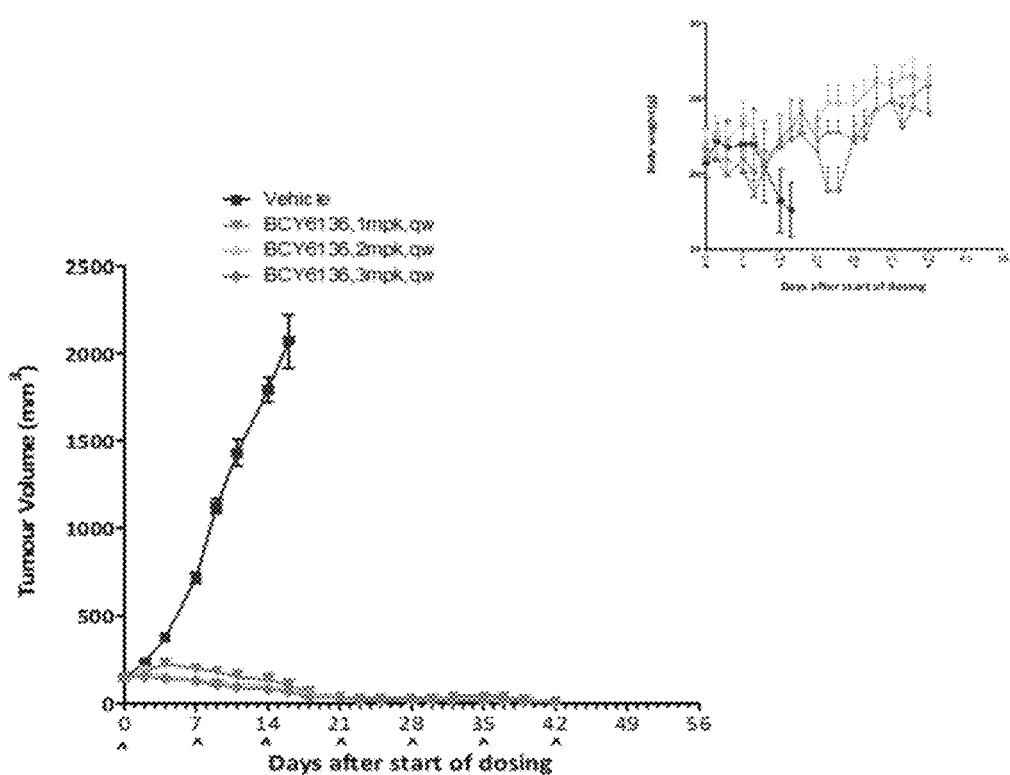
FIGS. 5 and 6: Body weight changes and tumor volume traces after administering BCY6136 (FIG. 5) and ADC (FIG. 6) to female BALB/c nude mice bearing PC-3 xenograft. Data points represent group mean body weight.
Figure 6:
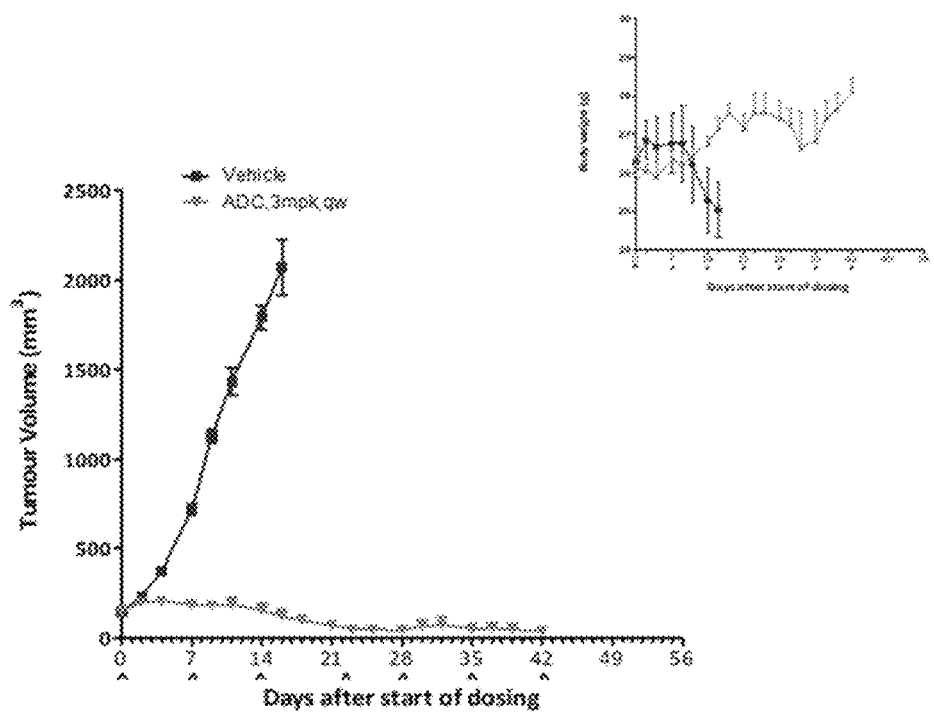

FIGS. 4-6 show that BCY6136 is effective in breast, lung and fibrosarcoma xenograft models following once weekly dosing.

Figure 2:
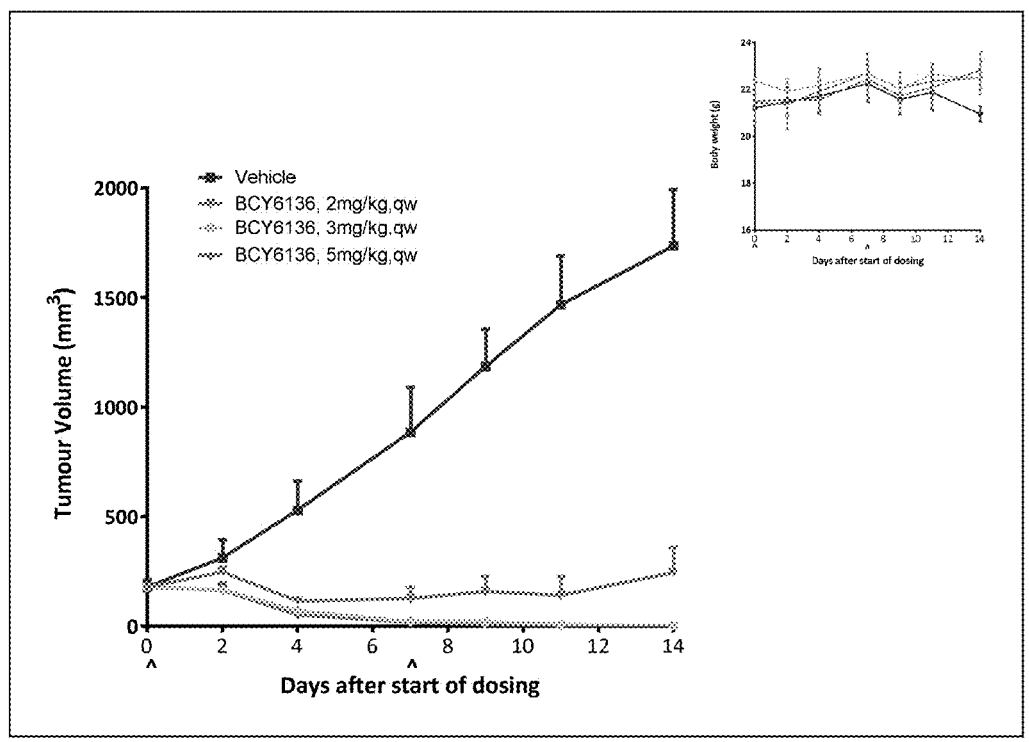
FIG. 2: Plot of mean tumour volume versus time for BCY6136 in HT1080 xenograft mice. Doses (2, 3 and 5 mg/kg) were administered on days 0 and 7. Body weight changes during treatment indicative of tumour burden, drug-associated toxicology and overall animal health are illustrated in the top right inset.

The HT1080 Fibrosarcoma Model:

In the HT1080 model complete regression of tumour growth was achieved by day 14 following once weekly dosing with BCY6136 on days 0 and 7 at 3 and 5 mg/kg (FIG. 2). Once weekly dosing with BCY6136 at 2 mg/kg on days 0 and 7 gave rise to tumour stasis (partial regression) (FIG. 2). BCY6136 treatment gave rise to no significant body weight loss (FIG. 2 inset) and there were no adverse clinical observations on drug treated mice throughout the study.

Figure 3:
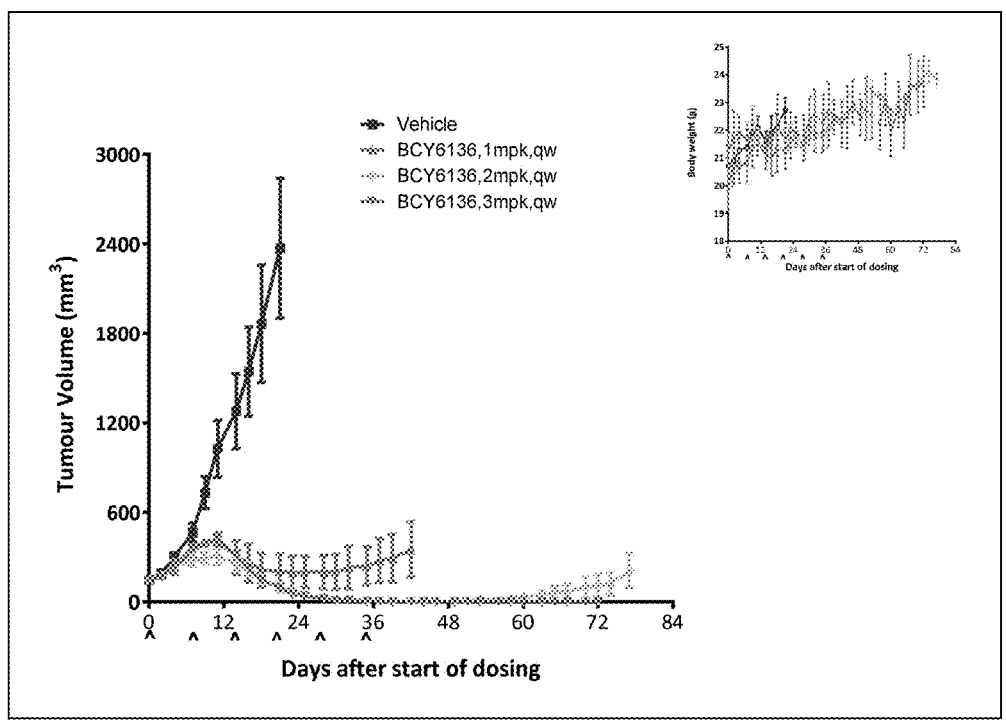
FIG. 3: Plot of mean tumour volume versus time for BCY6136 in NCI-H1975 xenograft mice. Doses (1, 2 and 3 mg/kg) were administered on days 0, 7, 14, 21, 28 and 35. Body weight changes during treatment indicative of tumour burden, drug-associated toxicology and overall animal health are illustrated in the top right inset.

The NCI-H1975 NSCLC Model:

Complete regression of tumour growth in the NCI-H1975 model was observed by around day 28 following 2 and 3 mg/kg once weekly dosing with BCY6136 (FIG. 3). Following dosing cessation on day 35 no tumour regrowth was observed in the 3 mg/kg treated animals from day 35 to day 72 when the 3 mg/kg arm measurements ended (FIG. 3). Dosing with BCY6136 at 2 mg/kg gave rise to complete regression in this model from around day 28. Following dosing cessation on day 35 there was no tumour regrowth until around day 51 at the 2 mg/kg dose. At this dose level moderate tumour re-growth was observed from around day 51 until study termination on day 77. 1 mg/kg treatment with BCY6136 gave rise to tumour stasis (partial regression) (FIG. 3). BCY6136 treatment gave rise to no significant body weight loss (FIG. 3 inset) and there were no adverse clinical observations on drug treated mice throughout the study.

The MDA-MB-231 Breast Model:

Tumour stasis (partial regression) was observed in the MDA-MB231 model following once weekly dosing at 2 and 3 mg/kg from days 0 to day 45 (FIG. 4). Some body weight loss (attributed to tumour burden) was observed in the 2 mg/kg treated animals (FIG. 4 inset).

These results demonstrate that BCY6136 gives rise to profound tumour growth inhibition in mice implanted with fibrosarcoma, breast and lung CDX xenografts following once daily dosing.

Study 5: Safety Studies in the Rat

Six (6) female rats were randomly assigned to 3 groups of 2 rats/group to determine the toxicity of BCY6136, following administered by IV bolus injection at 5, 7.5 and 10 mg/kg on days 1 and 8. The study was terminated on day 15.

No significant effects on coagulation parameters (Prothrombin time (sec), Activated partial thromboplastin time (sec) or Fibroginogen levels (g/L) were observed on days 2, 12 and 15 (data not shown). No in-life bleeding events were reported and no evidence of internal bleeding was detected following pathology examination.

Study 6: Safety Studies in the Cynomologous Monkeys

Twenty eight day toxicology studies with BCY6136 we conducted in cynomologous monkeys. BCY6136 was dosed at 1.0 and 2.0 mg/kg on days 1, 8, 15 and 22. Animals were euthanised and necropsied on day 29 (7 days after the final dose).

No significant effects on coagulation parameters relative to baseline were observed on days 18, 22 and 25 (data not shown) and day 29 (Table 15). No in-life bleeding events were reported and no evidence of internal bleeding was detected following pathology examination.

TABLE 15

Day 29 coagulation parameters following 1.0 and 2.0 mg/kg BCY6136 dosing to cynomolgus monkeys

| | 1.0 mg/kg × 4 | | 2.0 mg/kg × 4 | |
|---|---|---|---|---|
| | Baseline | Day 29 | Baseline | Day 29 |
| PT(s) | 13.4 | 11.7 | 9.4 | 9.7 |
| PT(s) | 11 | 9.2 | 11.2 | 11.0 |
| APTT(s) | 18.9 | 19.4 | 19.4 | 20.9 |
| APTT(s) | 16.1 | 15.7 | 18.7 | 18.2 |
| FIB(g/L) | 2.08 | 2.42 | 1.86 | 6.1 |
| FIB(g/L) | 2.28 | 2.35 | 1.82 | 3.1 |

Study 7: In Vivo Efficacy Study of BCY6136 and ADC in Treatment of PC-3 Xenograft in Balb/c Nude Mice (a) Study Objective The objective of the research is to evaluate the in vivo anti-tumor efficacy of BCY6136 in treatment of PC-3 xenograft.

(b) Experimental Design

| Group | Treatment | n | Dose (mg/kg) | Dosing Volume (μl/g) | Dosing Route | Schedule |
|---|---|---|---|---|---|---|
| 1 | Vehicle | 3 | — | 10 | iv | qw |
| 2 | BCY6136 | 3 | 1 | 10 | iv | qw |
| 3 | BCY6136 | 3 | 2 | 10 | iv | qw |
| 4 | BCY6136 | 3 | 3 | 10 | iv | qw |
| 5 | ADC | 3 | 3 | 10 | iv | qw |

(c) Experimental Methods and Procedures (i) Cell Culture

The PC-3 tumor cells will be maintained in F12K medium supplemented with 10% heat inactivated fetal bovine serum at 37° C. in an atmosphere of 5% $CO_2$ in air. The tumor cells will be routinely subcultured twice weekly. The cells growing in an exponential growth phase will be harvested and counted for tumor inoculation.

(ii) Tumor Inoculation

Each mouse will be inoculated subcutaneously at the right flank with PC-3 ($10*10^6$) tumor cells for tumor development. The animals will be randomized and treatment will be started when the average tumor volume reaches approximately 150 $mm^3$. The test article administration and the animal numbers in each group are shown in the following experimental design table.

(iii) Testing Article Formulation Preparation

| Test article | Con. (mg/ml) | Formulation |
|---|---|---|
| Vehicle | — | 50 mM Acetate/acetic acid pH 5 10% sucrose |
| BCY6136 | 0.1 | Dilute 90 μl 1 mg/ml BCY6136 stock with 810 μl vehicle buffer |
| | 0.2 | Dilute 180 μl 1 mg/ml BCY6136 stock with 720 μl vehicle buffer |
| | 0.3 | Dilute 270 μl 1 mg/ml BCY6136 stock with 630 μl vehicle buffer |
| ADC | 0.3 | Dilute 26 μl 10.47 mg/ml ADC stock with 874 μl ADC buffer |

(d) Results (i) Body Weight change and Tumor Growth Curve

Body weight and tumor growth curve are shown in FIGS. 5 and 6.

(ii) Tumor Volume Trace

Mean tumor volume over time in female Balb/c nude mice bearing PC-3 xenograft is shown in Table 16.

TABLE 16

Tumor volume trace over time

| Gr | Treatment | 0 | 2 | 4 | 7 | 9 | 11 | 14 | 16 | 18 | 21 |
|---|---|---|---|---|---|---|---|---|---|---|---|
| 1 | Vehicle, qw | 149 ± 9 | 235 ± 9 | 377 ± 9 | 718 ± 30 | 1126 ± 41 | 1431 ± 79 | 1792 ± 69 | 2070 ± 152 | | |
| 2 | BCY6136, 1 mpk, qw | 150 ± 11 | 185 ± 25 | 228 ± 31 | 201 ± 17 | 183 ± 23 | 153 ± 38 | 137 ± 33 | 107 ± 32 | 64 ± 28 | 45 ± 23 |
| 3 | BCY6136, 2 mpk, qw | 149 ± 18 | 179 ± 28 | 158 ± 22 | 137 ± 16 | 122 ± 15 | 114 ± 20 | 101 ± 16 | 79 ± 20 | 57 ± 19 | 42 ± 17 |
| 4 | BCY6136 3 mpk, qw | 149 ± 2 | 155 ± 8 | 144 ± 16 | 132 ± 20 | 107 ± 28 | 94 ± 23 | 83 ± 22 | 70 ± 27 | 38 ± 16 | 35 ± 17 |
| 5 | ADC 3 mpk, qw | 151 ± 27 | 203 ± 10 | 210 ± 12 | 189 ± 11 | 185 ± 16 | 190 ± 37 | 158 ± 36 | 124 ± 35 | 103 ± 27 | 74 ± 14 |

| Gr | Treatment | 23 | 25 | 28 | 30 | 32 | 35 | 37 | 39 | 42 |
|---|---|---|---|---|---|---|---|---|---|---|
| 1 | Vehicle, qw | | | | | | | | | |
| 2 | BCY6136, 1 mpk, qw | 35 ± 18 | 28 ± 14 | 37 ± 19 | 34 ± 17 | 42 ± 21 | 42 ± 23 | 43 ± 21 | 28 ± 14 | 18 ± 9 |
| 3 | BCY6136, 2 mpk, qw | 21 ± 11 | 22 ± 12 | 22 ± 12 | 24 ± 12 | 33 ± 16 | 22 ± 11 | 26 ± 14 | 22 ± 12 | 16 ± 9 |
| 4 | BCY6136 3 mpk, qw | 21 ± 10 | 23 ± 12 | 27 ± 14 | 22 ± 11 | 24 ± 12 | 20 ± 11 | 27 ± 14 | 12 ± 6 | 12 ± 6 |
| 5 | ADC 3 mpk, qw | 53 ± 16 | 50 ± 22 | 46 ± 23 | 70 ± 35 | 78 ± 39 | 53 ± 27 | 60 ± 30 | 53 ± 27 | 40 ± 22 |

(iii) Tumor Growth Inhibition Analysis Tumor growth inhibition rate for test articles in the PC-3 xenograft model was calculated based on tumor volume measurements at day 16 after the start of treatment.

TABLE 17

Tumor growth inhibition analysis

| Gr | Treatment | Tumor Volume (mm³)$^a$ | T/C$^b$ (%) | TGI (%) | P value compare with vehicle |
|---|---|---|---|---|---|
| 1 | Vehicle, qw | 2070 ± 152 | — | — | — |
| 2 | BCY6136, 1 mpk, qw | 107 ± 32 | 5.2 | 102.2 | p < 0.001 |
| 3 | BCY6136, 2 mpk, qw | 79 ± 20 | 3.8 | 103.6 | p < 0.001 |
| 4 | BCY6136, 3 mpk, qw | 70 ± 27 | 3.4 | 104.1 | p < 0.001 |
| 5 | ADC, 3 mpk, qw | 124 ± 35 | 6.0 | 101.4 | p < 0.001 |

$^a$Mean ± SEM.
$^b$Tumor Growth Inhibition is calculated by dividing the group average tumor volume for the treated group by the group average tumor volume for the control group (T/C).

(e) Results Summary and Discussion

In this study, the therapeutic efficacy of test articles in the PC-3 xenograft model was evaluated. The measured body weights and tumor volumes of all treatment groups at various time points are shown in the FIGS. 5 and 6 and Tables 16 and 17.

The mean tumor size of vehicle treated mice reached 2070 mm³ on day 16. BCY6136 at 1 mg/kg, qw (TV=107 mm³, TGI=102.2%, p<0.001), BCY6136 at 2 mg/kg, qw (TV=79 mm³, TGI=103.6%, p<0.001) and BCY6136 at 3 mg/kg, qw (TV=70 mm³, TGI=104.1%, p<0.001) showed potent anti-tumor effect. In this study, animal body weight was monitored regularly. All mice maintained their body weight well.

Study 8. In vivo efficacy study of BCY6136 in treatment of PC-3 xenograft in Balb/c Nude Mice (a) Study Objective The objective of the research is to evaluate the in vivo anti-tumor efficacy of BCY6136 in treatment of PC-3 xenograft in Balb/c nude mice.

(b) Experimental Design

| Group | Treatment | Dose (mg/kg) | N$^a$ | Dosing Route | Schedule |
|---|---|---|---|---|---|
| 1 | Vehicle | — | 4 | i.v. | qw × 4 weeks |
| 2 | BCY6136 | 0.167 | 4 | i.v. | qw × 4 weeks |
| 3$^b$ | BCY6136 | 0.5 | 4 | i.v. | qw × 4 weeks |
| 4 | BCY6136 | 1.5 | 4 | i.v. | qw × 4 weeks |
| 5$^b$ | BCY6136 | 0.5 | 4 | i.v. | q2w × 2 weeks |
| 6$^b$ | BCY6136 | 1.5 | 4 | i.v. | q2w × 2 weeks |
| 7 | EphA2-ADC | 0.33 | 4 | i.v. | qw × 4 weeks |
| 8 | EphA2-ADC | 1 | 4 | i.v. | qw × 4 weeks |
| 9 | EphA2-ADC | 3 | 4 | i.v. | qw × 4 weeks |
| 10$^c$ | Docetaxel | 15 | 4 | i.v. | qw × 4 weeks |

$^a$N, the number of animals in each group.
$^b$After 4 weeks' treatment demonstrated in the experimental design table, the mice of group 3, 5 and 6 were treated with BCY6136 1.5 mg/kg qw from day 52 during the monitoring schedule.
$^c$Due to the severe body weight loss of the Docetaxel treated mice after the first dosing, the treatment was suspended for 2 weeks, then a lower dosage (Docetaxel, 10 mg/kg) was performed on day 28. After that, the mice were treated with BCY6136 1.5 mg/kg qw from day 42 to day 70.

(c) Experimental Methods and Procedures (i) Cell Culture

The tumor cells were maintained in F-12K medium supplemented with 10% heat inactivated fetal bovine serum at 37° C. in an atmosphere of 5% $CO_2$ in air. The tumor cells were routinely subcultured twice weekly. The cells growing in an exponential growth phase were harvested and counted for tumor inoculation.

(ii) Tumor Inoculation

Each mouse was inoculated subcutaneously at the right flank with PC-3 tumor cells (10×10⁶) in 0.2 ml of PBS for tumor development. 52 animals were randomized when the average tumor volume reached 454 mm³. The test article administration and the animal numbers in each group were shown in the experimental design table.

(iii) Testing Article Formulation Preparation

| Test article | Purity | Conc. (mg/ml) | Formulation |
|---|---|---|---|
| Vehicle | — | — | 25 mM Histidine pH 7 10% sucrose |
| BCY6136 | 98.6% | — | 50 mM Acetate 10% sucrose pH 5 |
| | | 1 | Dissolve 2.70 mg BCY6136 in 2.662 ml Acetate buffer |
| | | 0.3 | Dilute 300 μl 1 mg/ml BCY6136 stock with 700 μl Acetate buffer[1] |
| | | 0.15 | Dilute 600 μl 0.3 mg/ml BCY6136 stock with 600 μl Acetate buffer |
| | | 0.05 | Dilute 200 μl 0.3 mg/ml BCY6136 stock with 1000 μl Acetate buffer |
| | | 0.0167 | Dilute 66.7 μl 0.3 mg/ml BCY6136 stock with 1133.3 μl Acetate buffer |
| EphA2-ADC | — | — | 25 mM Histidine pH 5.5 |
| | | 0.033 | Dilute 9.3 μl 4.24 mg/ml EphA2-ADC stock with 1191 μl His buffer |
| | | 0.1 | Dilute 28 μl 4.24 mg/ml EphA2-ADC stock with 1172 μl His buffer |
| | | 0.3 | Dilute 84.9 μl 4.24 mg/ml EphA2-ADC stock with 1115 μl His buffer |
| Docetaxel | — | 10 | Mix 0.5 ml 20 mg Docetaxel with 1.5 ml buffer |
| | | 1.5 | Dilute 180 μl 10 mg/ml Docetaxel stock with 1020 μl saline buffer |

[1] 50 mM Acetate 10% sucrose pH 5 3. 25 mM Histidine pH 5.5

Figure 7:
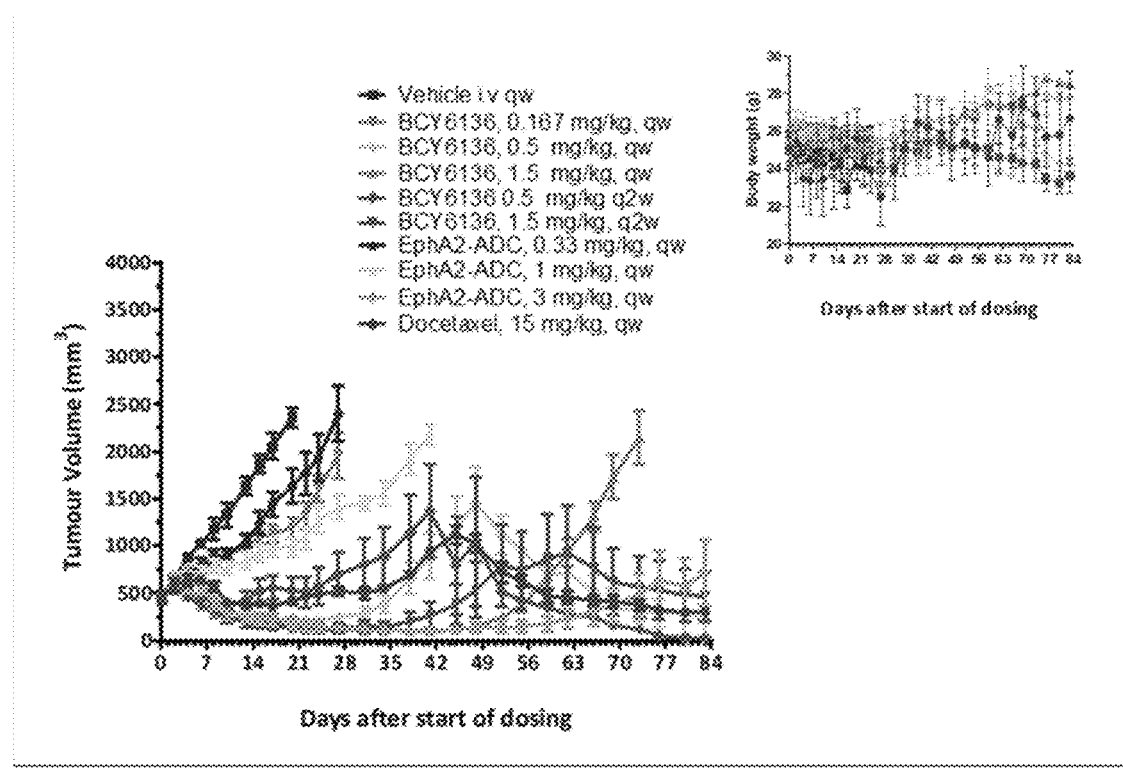
FIG. 7: Body weight changes and tumor volume traces after administering BCY6136, EphA2-ADC or Docetaxel to male Balb/c nude mice bearing PC-3 xenograft. Data points represent group mean body weight.

(c) Results
(i) Body Weight change and Tumor Growth Curve
Body weight and tumor growth curve is shown in FIG. 7.
(ii) Tumor Volume Trace
Mean tumor volume over time in male Balb/c nude mice bearing PC-3 xenograft is shown in Table 18.

TABLE 18

Tumor volume trace over time (Day 0 to day 20)

| Gr. | Treatment | Days after the start of treatment | | | | | |
|---|---|---|---|---|---|---|---|
| | | 0 | 2 | 4 | 6 | 8 | 10 |
| 1 | Vehicle, qw | 456 ± 25 | 648 ± 50 | 880 ± 23 | 1022 ± 29 | 1178 ± 118 | 1327 ± 133 |
| 2 | BCY6136 0.167 mpk, qw | 450 ± 33 | 631 ± 55 | 695 ± 78 | 739 ± 39 | 850 ± 68 | 904 ± 73 |
| 3 | BCY6136 0.5 mpk, qw | 451 ± 47 | 622 ± 96 | 519 ± 70 | 460 ± 55 | 398 ± 50 | 329 ± 38 |
| 4 | BCY6136 1.5 mpk, qw | 458 ± 49 | 587 ± 63 | 494 ± 54 | 363 ± 32 | 283 ± 32 | 237 ± 24 |
| 5 | BCY6136 0.5 mpk, q2w | 454 ± 37 | 643 ± 25 | 531 ± 37 | 458 ± 33 | 411 ± 32 | 382 ± 49 |
| 6 | BCY6136 1.5 mpk, q2w 1.5 mpk, qw | 452 ± 42 | 590 ± 75 | 457 ± 49 | 375 ± 44 | 328 ± 47 | 242 ± 63 |
| 7 | EphA2-ADC 0.33 mpk, qw | 457 ± 43 | 636 ± 57 | 712 ± 70 | 792 ± 78 | 870 ± 87 | 900 ± 58 |
| 8 | EphA2-ADC 1 mpk, qw | 450 ± 49 | 617 ± 48 | 673 ± 50 | 721 ± 61 | 782 ± 78 | 755 ± 67 |
| 9 | EphA2-ADC 3 mpk, qw | 452 ± 60 | 593 ± 98 | 643 ± 141 | 593 ± 106 | 433 ± 103 | 290 ± 81 |
| 10 | Docetaxel 15 mpk, qw | 453 ± 62 | 584 ± 72 | 632 ± 56 | 636 ± 48 | 568 ± 50 | 408 ± 31 |

| | | Days after the start of treatment | | | |
|---|---|---|---|---|---|
| Gr. | Treatment | 13 | 15 | 17 | 20 |
| 1 | Vehicle, qw | 1631 ± 93 | 1868 ± 90 | 2052 ± 139 | 2364 ± 102 |
| 2 | BCY6136 0.167 mpk, qw | 975 ± 47 | 1089 ± 74 | 1124 ± 92 | 1188 ± 111 |
| 3 | BCY6136 0.5 mpk, qw | 260 ± 33 | 249 ± 33 | 231 ± 38 | 234 ± 42 |
| 4 | BCY6136 1.5 mpk, qw | 192 ± 13 | 164 ± 16 | 155 ± 20 | 131 ± 19 |
| 5 | BCY6136 0.5 mpk, q2w | 430 ± 88 | 522 ± 124 | 560 ± 129 | 530 ± 147 |

TABLE 18-continued

Tumor volume trace over time (Day 0 to day 20)

| | | | | | |
|---|---|---|---|---|---|
| 6 | BCY6136 1.5 mpk, q2w 1.5 mpk, qw | 206 ± 61 | 197 ± 62 | 182 ± 55 | 128 ± 36 |
| 7 | EphA2-ADC 0.33 mpk, qw | 1049 ± 66 | 1242 ± 123 | 1443 ± 129 | 1637 ± 181 |
| 8 | EphA2-ADC 1 mpk, qw | 840 ± 93 | 913 ± 91 | 978 ± 100 | 981 ± 100 |
| 9 | EphA2-ADC 3 mpk, qw | 268 ± 64 | 232 ± 60 | 225 ± 66 | 184 ± 62 |
| 10 | Docetaxel 15 mpk, qw | 374 ± 26 | 388 ± 36 | 361 ± 25 | 419 ± 31 |

(iii) Tumor Growth Inhibition Analysis

Tumor growth inhibition rate for test articles in the PC-3 xenograft model was calculated based on tumor volume measurements at day 20 after the start of the treatment.

TABLE 19

Tumor growth inhibition analysis

| Gr | Treatment | Tumor Volume (mm³)[a] | T/C[b] (%) | TGI (%) | P value compared with vehicle |
|---|---|---|---|---|---|
| 1 | Vehicle, qw | 2364 ± 102 | — | — | — |
| 2 | BCY6136, 0.167 mpk, qw | 1188 ± 111 | 50.2 | 61.4 | p < 0.001 |
| 3 | BCY6136, 0.5 mpk, qw | 234 ± 42 | 9.9 | 111.4 | p < 0.001 |
| 4 | BCY6136, 1.5 mpk, qw | 131 ± 19 | 5.5 | 117.2 | p < 0.001 |
| 5 | BCY6136, 0.5 mpk, q2w | 530 ± 147 | 22.4 | 96.0 | p < 0.001 |
| 6 | BCY6136, 1.5 mpk, q2w | 128 ± 36 | 5.4 | 117.0 | p < 0.001 |
| 7 | EphA2-ADC, 0.33 mpk, qw | 1637 ± 181 | 69.2 | 38.1 | p < 0.001 |
| 8 | EphA2-ADC, 1 mpk, qw | 981 ± 100 | 41.5 | 72.2 | p < 0.001 |
| 9 | EphA2-ADC, 3 mpk, qw | 184 ± 62 | 7.8 | 114.0 | p < 0.001 |
| 10 | Docetaxel, 15 mpk, qw | 419 ± 31 | 17.7 | 101.8 | p < 0.001 |

[a]Mean ± SEM.
[b]Tumor Growth Inhibition is calculated by dividing the group average tumor volume for the treated group by the group average tumor volume for the control group (T/C).

(d) Results Summary and Discussion

In this study, the therapeutic efficacy of test articles in the PC-3 xenograft model was evaluated. The measured body weights and tumor volumes of all treatment groups at various time points are shown in the FIG. 7 and Tables 18 and 19.

The mean tumor size of vehicle treated mice reached 2364 mm³ on day 20. BCY6136 at 0.167 mg/kg, qw (TV=1188 mm³, TGI=61.4%, p<0.001), 0.5 mg/kg, q2w (TV=530 mm³, TGI=96.0%, p<0.001), 0.5 mg/kg, qw (TV=234 mm³, TGI=111.4%, p<0.001) and 1.5 mg/kg, qw (TV=131 mm³, TGI=117.2%, p<0.001) produced significant anti-tumor activity in dose or dose-frequency dependent manner on day 20. BCY6136 at 1.5 mg/kg, q2w (TV=128 mm³, TGI=117.0%, p<0.001) produced comparable anti-tumor activity with BCY6136 1.5 mg/kg qw. Among them, the mice treated with BCY6136, 0.5 mg/kg qw or BCY6136, 0.5 mg/kg q2w showed obvious tumor relapse after ceasing the treatment, further treatment with BCY6136, 1.5 mg/kg qw from day 52 worked well on the tumor regression. The mice treated with BCY6136, 1.5 mg/kg q2w also showed tumor relapse after ceasing the treatment, but further dosing didn't work on complete tumor regression. The mice treated with BCY6136, 1.5 mpk qw didn't show any tumor relapse until day 48.

EphA2-ADC at 0.33 mg/kg, qw (TV=1637 mm³, TGI=38.1%, p<0.001), 1 mg/kg, qw (TV=981 mm³, TGI=72.2%, p<0.001) and 3 mg/kg, qw (TV=184 mm³, TGI=114.0%, p<0.001) produced significant anti-tumor activity in dose dependent manner on day 20. The mice treated with EphA2-ADC, 3 mg/kg qw didn't show any tumor relapse until day 59.

Docetaxel at 15 mg/kg, qw (TV=419 mm³, TGI=101.8%, p<0.001) produced significant anti-tumor activity but caused severe animal body weight loss. After ceasing the treatment, the mice showed obvious tumor relapse. The treatment with BCY6136, 1.5 mg/kg qw from day 42 worked well on tumor regression of these mice.

Study 9. In Vivo Efficacy Test of BCY6136 in Treatment of NCI-H1975 Xenograft in Balb/c Nude Mice (a) Study Objective The objective of the research was to evaluate the in vivo anti-tumor efficacy of BCY6136 in treatment of NCI-H1975 xenograft model in Balb/c nude mice.

(b) Experimental Design

| Group | Treatment | n | Dose (mg/kg) | Dosing Volume (μl/g) | Dosing Route | Schedule |
|---|---|---|---|---|---|---|
| 1 | Vehicle | 3 | — | 10 | iv | qw |
| 2 | BCY6136 | 3 | 1 | 10 | iv | qw |
| 3 | BCY6136 | 3 | 2 | 10 | iv | qw |
| 4 | BCY6136 | 3 | 3 | 10 | iv | qw |

(c) Experimental Methods and Procedures (i) Cell Culture

The cells growing in an exponential growth phase were harvested and counted for tumor inoculation.

(ii) Tumor Inoculation

Each mouse was inoculated subcutaneously at the right flank with NCI-H1975 tumor cells (10×10^6) in 0.2 ml of PBS for tumor development. 36 animals were randomized when the average tumor volume reached 149 mm³. The test article administration and the animal numbers in each group were shown in the experimental design table.

(iii) Testing Article Formulation Preparation

| Treatment | Dose (mg/ml) | Formulation |
|---|---|---|
| Vehicle | | 50 mM Acetate, 10% sucrose pH = 5 |
| BCY6136 | 1 | Dissolve 3.79 mg BCY6136 in 3.695 ml formulation buffer |
| | 0.3 | Dilute 270 μl 1 mg/ml BCY6136 with 630 μl formulation buffer |
| | 0.2 | Dilute 180 μl 1 mg/ml BCY6136 with 720 μl formulation buffer |
| | 0.1 | Dilute 90 μl 1 mg/ml BCY6136 with 810 μl formulation buffer |

Figure 8:
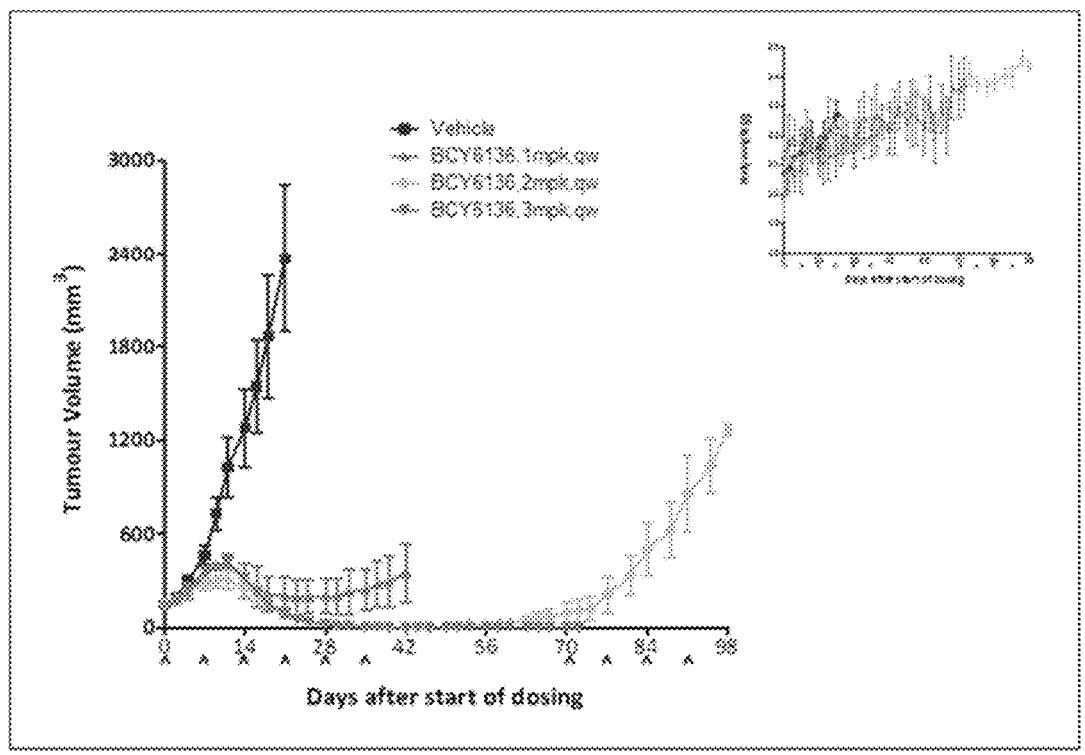
FIG. 8: Body weight changes and tumor volume trace after administering BCY6136 to female Balb/c nude mice bearing NCI-H1975 xenograft. Data points represent group mean tumor volume and body weight.

(iv) Sample Collection
On PG-D44, we fixed the tumors of Group 2 for FFPE.
At the end of study, we the tumors of Group 3 for FFPE.
(d) Results
(i) Body Weight change and Tumor Growth Curve
Body weight and tumor growth are shown in FIG. 8.
(ii) Tumor Volume Trace
Mean tumor volume over time in female Balb/c nude mice bearing NCI-H1975 xenograft is shown in Table 20 to 24.

TABLE 20

Tumor volume trace (PG-D 0~PG-D 17)

| Gr. | Treatment | Days after the start of treatment | | | | | | | |
|---|---|---|---|---|---|---|---|---|---|
| | | 0 | 2 | 4 | 7 | 9 | 11 | 14 | 17 |
| 1 | Vehicle, qw | 148 ± 4 | 195 ± 11 | 297 ± 33 | 466 ± 64 | 732 ± 107 | 1028 ± 192 | 1278 ± 252 | 1543 ± 298 |
| 2 | BCY6136, 1 mpk, qw | 150 ± 6 | 178 ± 20 | 232 ± 49 | 336 ± 43 | 400 ± 24 | 407 ± 42 | 299 ± 113 | 261 ± 127 |
| 3 | BCY6136, 2 mpk, qw | 150 ± 14 | 181 ± 26 | 237 ± 27 | 277 ± 36 | 297 ± 37 | 306 ± 55 | 256 ± 53 | 218 ± 49 |
| 4 | BCY6136, 3 mpk, qw | 148 ± 9 | 168 ± 10 | 231 ± 6 | 365 ± 16 | 390 ± 13 | 423 ± 42 | 319 ± 26 | 228 ± 16 |

TABLE 21

Tumor volume trace (PG-D 18~PG-D 35)

| Gr. | Treatment | Days after the start of treatment | | | | | | | |
|---|---|---|---|---|---|---|---|---|---|
| | | 18 | 21 | 23 | 25 | 28 | 30 | 33 | 35 |
| 1 | Vehicle, qw | 1864 ± 395 | 2371 ± 470 | — | — | — | — | — | — |
| 2 | BCY6136, 1 mpk, qw | 215 ± 113 | 205 ± 117 | 197 ± 113 | 200 ± 105 | 202 ± 112 | 202 ± 117 | 230 ± 142 | 241 ± 127 |
| 3 | BCY6136, 2 mpk, qw | 149 ± 31 | 99 ± 30 | 69 ± 22 | 42 ± 13 | 30 ± 10 | 16 ± 8 | 20 ± 9 | 4 ± 2 |
| 4 | BCY6136, 3 mpk, qw | 149 ± 17 | 94 ± 30 | 50 ± 15 | 41 ± 21 | 21 ± 8 | 6 ± 6 | 10 ± 6 | 3 ± 1 |

TABLE 22

Tumor volume trace (PG-D 37~PG-D 53)

| Gr. | Treatment | Days after the start of treatment | | | | | | | |
|---|---|---|---|---|---|---|---|---|---|
| | | 37 | 39 | 42 | 44 | 46 | 49 | 51 | 53 |
| 2 | BCY6136, 1 mpk, qw | 277 ± 149 | 294 ± 159 | 351 ± 188 | — | — | — | — | — |
| 3 | BCY6136, 2 mpk, qw | 7 ± 4 | 2 ± 1 | 1 ± 0 | 3 ± 1 | 2 ± 1 | 3 ± 2 | 6 ± 3 | 14 ± 10 |
| 4 | BCY6136, 3 mpk, qw | 3 ± 3 | 2 ± 1 | 1 ± 0 | 0 ± 0 | 0 ± 0 | 0 ± 0 | 1 ± 0 | 1 ± 0 |

TABLE 23

Tumor volume trace (PG-D 56~PG-D 74)

| Gr. | Treatment | Days after the start of treatment | | | | | | | |
|---|---|---|---|---|---|---|---|---|---|
| | | 56 | 58 | 60 | 63 | 65 | 67 | 70 | 72 | 74 |
| 3 | BCY6136, 2 mpk, qw | 16 ± 11 | 27 ± 18 | 34 ± 23 | 45 ± 31 | 63 ± 40 | 71 ± 47 | 95 ± 70 | 111 ± 73 | 122 ± 75 |
| 4 | BCY6136, 3 mpk, qw | 1 ± 0 | 1 ± 0 | 1 ± 0 | 0 ± 0 | 0 ± 0 | 0 ± 0 | 0 ± 0 | 0 ± 0 | — |

TABLE 24

Tumor volume trace (PG-D 77~PG-D 98)

| | | Days after the start of treatment | | | | | |
|---|---|---|---|---|---|---|---|
| Gr. | Treatment | 77 | 81 | 84 | 88 | 91 | 95 | 98 |
| 3 | BCY6136, 2 mpk, qw | 208 ± 112 | 337 ± 123 | 501 ± 172 | 626 ± 182 | 856 ± 245 | 1035 ± 169 | 1266 ± 39 |

(iii) Tumor Growth Inhibition Analysis

Tumor growth inhibition rate for BCY6136 in the NCI-H1975 xenograft model was calculated based on tumor volume measurements at day 21 after the start of treatment.

TABLE 25

Tumor growth inhibition analysis

| Gr | Treatment | Tumor Volume (mm³)[a] | T/C[b] (%) | TGI (%) | P value |
|---|---|---|---|---|---|
| 1 | Vehicle, qw | 2371 ± 470 | — | — | — |
| 2 | BCY6136, 1 mpk, qw | 205 ± 117 | 8.6 | 97.5 | p < 0.001 |
| 3 | BCY6136, 2 mpk, qw | 99 ± 30 | 4.2 | 102.3 | p < 0.001 |
| 4 | BCY6136, 3 mpk, qw | 94 ± 30 | 4.0 | 102.4 | p < 0.001 |

[a]Mean ± SEM.
[b]Tumor Growth Inhibition is calculated by dividing the group average tumor volume for the treated group by the group average tumor volume for the control group (T/C).

(e) Results Summary and Discussion

In this study, the therapeutic efficacy of BCY6136 in the NCI-H1975 xenograft model was evaluated. The measured body weights and tumor volumes of all treatment groups at various time points are shown in the FIG. 8 and Tables 20 to 25.

The mean tumor size of vehicle treated mice reached 2371 mm³ on day 21. BCY6136 at 1 mg/kg (TV=205 mm³, TGI=97.5%, p<0.001), 2 mg/kg (TV=99 mm³, TGI=102.3%, p<0.001) and 3 mg/kg (TV=94 mm³, TGI=102.4%, p<0.001) produced potent antitumor activity. BCY6136 at 2 mg/kg and 3 mg/kg eradicated the tumors or regressed the tumor to small size. The treatments was suspended from day 35, and the tumors in 3 mg/kg group didn't show obvious re-growth in following 5-6 weeks monitoring, however tumors in 2 mg/kg group showed obvious regrowth and didn't show significant tumor inhibition when resuming the dosing. In this study, mice maintained the bodyweight well.

Study 10. In Vivo Efficacy Study of BCY6136 in the LU-01-0251 PDX Model in Balb/c Nude Mice (a) Study Objective The objective of the research is to evaluate the in vivo anti-tumor efficacy of BCY6136 in the LU-01-0251 PDX model in Balb/c nude mice.

(b) Experimental Design

| Group | Treatment | n | Dose (mg/kg) | Dosing Volume (μl/g) | Dosing Route | Schedule |
|---|---|---|---|---|---|---|
| 1 | Vehicle | 5 | — | 10 | iv | qw |
| 2 | BCY6136 | 5 | 1 | 10 | iv | qw |
| 3 | BCY6136 | 5 | 2 | 10 | iv | qw |
| 4 | BCY6136 | 5 | 3 | 10 | iv | qw |
| 5 | ADC | 5 | 3 | 10 | iv | qw |

(c) Experimental Methods and Procedures (i) Tumor Inoculation

Each mouse was inoculated subcutaneously at the right flank with LU-01-0251 of tumor fragment (~30 mm³) for tumor development. The treatment was started when the average tumor volume reached 174 mm³ for efficacy study. The test article administration and the animal number in each group are shown in the experimental design table.

(ii) Testing Article Formulation Preparation

| Test article | Conc. (mg/ml) | Formulation |
|---|---|---|
| Vehicle | — | 50 mM Acetate 10% sucrose pH 5 |
| BCY6136 | 0.3 | Dissolve 6.11 mg BCY6136 in 20 ml Acetate buffer[1] |
| | 0.2 | Dilute 940 μl 0.3 mg/ml BCY6136 stock with 470 μl Acetate buffer |
| | 0.1 | Dilute 470 μl 0.3 mg/ml BCY6136 stock with 940 μl Acetate buffer |
| ADC | 0.3 | Dilute 43 μl 10.47 mg/ml ADC stock with 1457 μl ADC buffer[2] |

[1]Acetate buffer: 50 mM Acetate 10% sucrose pH 5
[2]ADC buffer: 20 mM Histidine pH 5.5

(d) Results (i) Body Weight change and Tumor Growth Curve

Figure 9:
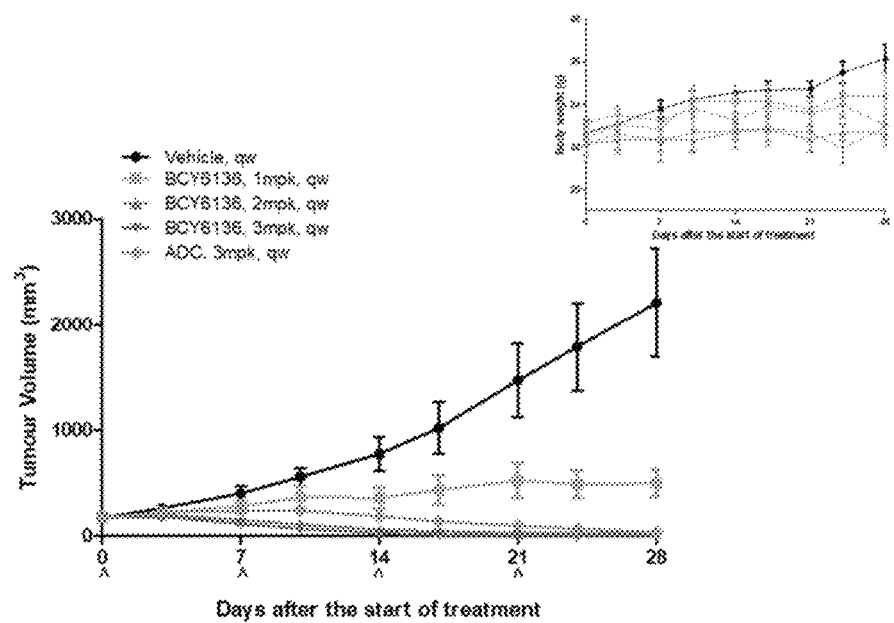
FIGS. 9 and 10: Body weight changes and tumor volume traces after administering BCY6136 and ADC to female Balb/c nude mice bearing LU-01-0251 xenograft. Data points represent group mean body weight.

Body weight and tumor growth curve are shown in FIG. 9.

(ii) Tumor Volume Trace

Mean tumor volume on day 28 after the start of treatment in female Balb/c nude mice bearing LU-01-0251 xenograft is shown in Table 26.

TABLE 26

Tumor volume trace over time

| Day | Group 1 Vehicle | Group 2 BCY6136, 1 mpk, qw | Group 3 BCY6136, 2 mpk, qw | Group 4 BCY6136, 3 mpk, qw | Group 5 ADC, 3 mpk, qw |
|---|---|---|---|---|---|
| 0 | 174 ± 17 | 175 ± 15 | 174 ± 17 | 175 ± 14 | 174 ± 16 |
| 3 | 264 ± 33 | 230 ± 29 | 205 ± 21 | 187 ± 19 | 227 ± 12 |
| 7 | 403 ± 68 | 281 ± 55 | 154 ± 21 | 118 ± 13 | 239 ± 42 |
| 10 | 562 ± 83 | 370 ± 104 | 111 ± 19 | 72 ± 12 | 241 ± 46 |
| 14 | 777 ± 163 | 362 ± 104 | 62 ± 17 | 30 ± 5 | 191 ± 47 |
| 17 | 1021 ± 246 | 437 ± 136 | 46 ± 13 | 17 ± 3 | 139 ± 39 |

TABLE 26-continued

Tumor volume trace over time

| Day | Group 1 Vehicle | Group 2 BCY6136, 1 mpk, qw | Group 3 BCY6136, 2 mpk, qw | Group 4 BCY6136, 3 mpk, qw | Group 5 ADC, 3 mpk, qw |
|---|---|---|---|---|---|
| 21 | 1472 ± 342 | 526 ± 167 | 30 ± 18 | 4 ± 3 | 101 ± 31 |
| 24 | 1790 ± 417 | 491 ± 132 | 32 ± 24 | 1 ± 1 | 70 ± 23 |
| 28 | 2208 ± 512 | 499 ± 128 | 32 ± 30 | 0 ± 0 | 39 ± 14 |

(iii) Tumor Growth Inhibition Analysis p Tumor growth inhibition rate for BCY6136 and ADC in the LU-01-0251 PDX model was calculated based on tumor volume measurements at day 28 after the start of the treatment.

TABLE 27

Tumor growth inhibition analysis

| Group | Treatment | Tumor Volume (mm$^3$)$^a$ | T/C$^b$ (%) | TGI (%) | P value |
|---|---|---|---|---|---|
| 1 | Vehicle, qw | 2208 ± 512 | — | — | — |
| 2 | BCY6136, 1 mpk, qw | 499 ± 128 | 22.6 | 84.0 | p < 0.001 |
| 3 | BCY6136, 2 mpk, qw | 32 ± 30 | 1.4 | 107.0 | p < 0.001 |
| 4 | BCY6136, 3 mpk, qw | 0 ± 0 | 0.0 | 108.6 | p < 0.001 |
| 5 | ADC, 3 mpk, qw | 39 ± 14 | 1.8 | 106.6 | p < 0.001 |

$^a$Mean ± SEM;
$^b$Tumor Growth Inhibition is calculated by dividing the group average tumor volume for the treated group by the group average tumor volume for the control group (T/C).

(e) Results Summary and Discussion

In this study, the therapeutic efficacy of BCY6136 and ADC in LU-01-0251 PDX model was evaluated. The measured body weight and tumor volume of all treatment groups at various time points are shown in the FIG. 9 and Tables 26 and 27.

In this study, the mean tumor volume of vehicle treated mice reached 2208 mm$^3$ on day 28 after the start of treatment. BCY6136 at 1 mg/kg, qw (TV=499 mm$^3$, TGI=84.0%, p<0.001), 2 mg/kg, qw (TV=32 mm$^3$, TGI=107.0%, p<0.001) and 3 mg/kg, qw (TV=0 mm$^3$, TGI=108.6%, p<0.001) produced dose-dependent anti-tumor activity. ADC at 3 mg/kg, qw (TV=39 mm$^3$, TGI=106.6%, p<0.001) showed significant anti-tumor activity.

Study 11: In Vivo Efficacy Study of BCY6136 in the LU-01-0251 PDX Model in Balb/c Nude Mice (a) Study Objective The objective of the research is to evaluate the in vivo anti-tumor efficacy of BCY6136 in the LU-01-0251 PDX model in Balb/c nude mice.

(b) Experimental Design

| Group | Treatment | n | Dose (mg/kg) | Dosing Volume (μl/g) | Dosing Route | Schedule |
|---|---|---|---|---|---|---|
| 1 | Vehicle | 5 | — | 10 | iv | Qw * 21 |
| 2 | BCY6136 | 5 | 1 | 10 | iv | Qw * 28 |
| 3$^a$ | BCY6136 | 5 | 2 | 10 | iv | Qw * 70 |
| 4$^b$ | BCY6136 | 5 | 3 | 10 | iv | Qw * 56 |
| 5$^c$ | ADC | 5 | 3 | 10 | iv | Qw * 70 |

$^a$The dosing schedule was kept from day 0 to day 70 for all the mice of this group, then the mouse 3-2 and mouse 3-4 were further dosed with BCY6136 3 mg/kg qw from day 77 while the treatment of the other 3 mice was suspended. The dosing schedule was kept from day 0 to day 56 for all the mice of this group.
$^b$The dosing schedule was kept from day 0 to day 70 for all the mice of this group.

(c) Experimental Methods and Procedures (i) Tumor Inoculation

Each mouse was inoculated subcutaneously at the right flank with LU-01-0251 of tumor fragment (~-30 mm$^3$) for tumor development. The treatment was started when the average tumor volume reached 960 mm$^3$ for efficacy study. The test article administration and the animal number in each group are shown in the experimental design table.

(ii) Testing Article Formulation Preparation

| Test article | Conc. (mg/ml) | Formulation |
|---|---|---|
| Vehicle | — | 25 mM Histidine 10% sucrose pH 7 |
| BCY6136 | 0.3 | 0.3 mg/ml BCY6136 was prepared as in Study 10 hereinbefore |
|  | 0.2 | Dilute 940 μl 0.3 mg/ml BCY6136 stock with 470 μl His-buffer$^1$ |
|  | 0.1 | Dilute 470 μl 0.3 mg/ml BCY6136 stock with 940 μl His-buffer |
| ADC | 0.3 | Dilute 43 μl 10.47 mg/ml ADC stock with 1457 μl ADC-buffer$^2$ |

$^1$His-buffer: 25 mM Histidine 10% sucrose pH 7
$^2$ADC-buffer: 20 mM Histidine pH 5.5

(iii) Sample Collection

Tumor of mouse #3-2 was collected for FFPE on Day 94. Tumors of mice #5-2 and 5-3 were collected and embed into 1 FFPE block on Day 140.

(d) Results (i) Body Weight change and Tumor Growth Curve

Figure 10:
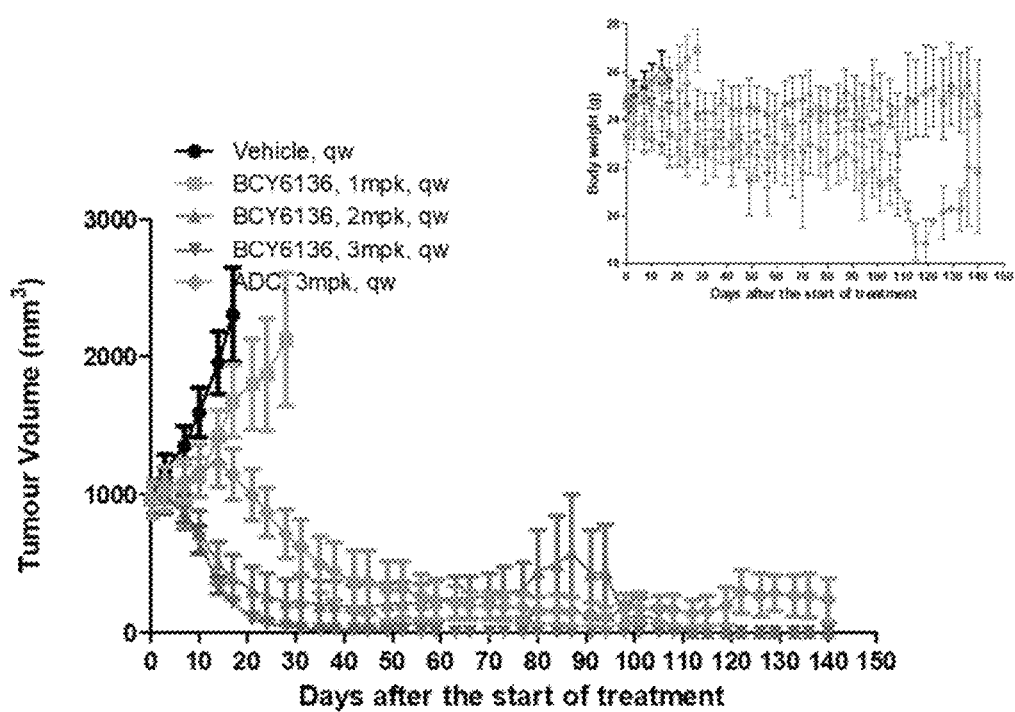

Body weight and tumor growth curve are shown in FIG. 10.

(ii) Tumor Volume Trace

Mean tumor volume on day 0 to day 28 after the start of treatment in female Balb/c nude mice bearing LU-01-0251 xenograft is shown in Table 28.

TABLE 28

Tumor volume trace over time

| Day | Group 1 Vehicle | Group 2 BCY6136, 1 mpk, qw | Group 3 BCY6136, 2 mpk, qw | Group 4 BCY6136, 3 mpk, qw | Group 5 ADC, 3 mpk, qw |
|---|---|---|---|---|---|
| 0  | 962 ± 102  | 963 ± 97   | 962 ± 137 | 960 ± 103 | 959 ± 124 |
| 3  | 1176 ± 108 | 1003 ± 121 | 973 ± 105 | 989 ± 128 | 1043 ± 158 |
| 7  | 1351 ± 142 | 1056 ± 151 | 873 ± 125 | 890 ± 98  | 1100 ± 156 |
| 10 | 1591 ± 179 | 1122 ± 139 | 722 ± 157 | 674 ± 96  | 1172 ± 188 |
| 14 | 1951 ± 225 | 1417 ± 191 | 503 ± 151 | 342 ± 64  | 1228 ± 174 |
| 17 | 2301 ± 344 | 1672 ± 262 | 398 ± 160 | 216 ± 43  | 1143 ± 186 |
| 21 |            | 1794 ± 328 | 307 ± 169 | 94 ± 26   | 996 ± 187 |
| 24 |            | 1867 ± 408 | 261 ± 168 | 62 ± 14   | 867 ± 178 |
| 28 |            | 2120 ± 483 | 217 ± 167 | 45 ± 16   | 713 ± 178 |

(iii) Tumor Growth Inhibition Analysis

Tumor growth inhibition rate for BCY6136 and ADC in the LU-01-0251 PDX model was calculated based on tumor volume measurements at day 17 after the start of the treatment.

TABLE 29

Tumor growth inhibition analysis

| Group | Treatment | Tumor Volume (mm$^3$)$^a$ | T/C$^b$ (%) | TGI (%) | P value |
|---|---|---|---|---|---|
| 1 | Vehicle, qw      | 2301 ± 344 | —    | —     | —        |
| 2 | BCY6136, 1 mpk, qw | 1672 ± 262 | 72.7 | 47.0  | p > 0.05 |
| 3 | BCY6136, 2 mpk, qw | 398 ± 160  | 17.3 | 142.1 | p < 0.001 |
| 4 | BCY6136, 3 mpk, qw | 216 ± 43   | 9.4  | 155.6 | p < 0.001 |
| 5 | ADC, 3 mpk, qw    | 1143 ± 186 | 49.7 | 86.3  | p < 0.01 |

$^a$Mean ± SEM;
$^b$Tumor Growth Inhibition is calculated by dividing the group average tumor volume for the treated group by the group average tumor volume for the control group (T/C).

(e) Results Summary and Discussion

In this study, the therapeutic efficacy of BCY6136 and ADC in LU-01-0251 PDX model was evaluated. The measured body weight and tumor volume of all treatment groups at various time points are shown in the FIG. 10 and Tables 28 and 29.

In this study, the treatment was started when the average tumor volume reached 960 mm$^3$. On day 17 after the start of treatment, the mean tumor volume of vehicle treated mice reached 2301 mm$^3$. BCY6136 at 1 mg/kg qw (TV=1672 mm$^3$, TGI=47.0%, p>0.05) didn't show obvious antitumor activity; BCY6136 at 2 mg/kg qw (TV=398 mm$^3$, TGI=142.1%, p<0.001) and 3 mg/kg qw (TV=216 mm$^3$, TGI=155.6%, p<0.001) produced dose-dependent anti-tumor activity on day 17.

After 70 days' treatment with BCY6136 at 2 mg/kg qw, 3 in 5 of these mice showed complete tumor regression, the other 2 mice showed obvious tumor relapse from day 42 to day 77. Then further treatment with BCY6136 3 mg/kg qw was performed to the two relapse tumors from day 7, one of tumor showed obvious tumor regress while another one showed resistance to the treatment.

After 56 days' treatment with BCY6136 at 3 mg/kg qw, all the mice of this group showed complete tumor regression.

ADC at 3 mg/kg qw (TV=1143 mm$^3$, TGI=86.3%, p<0.01) showed obvious anti-tumor activity on day 17, after another 53 day' treatment, these mice showed further but not complete tumor regression.

In this study, there were some mice showed sudden bodyweight loss, this may have the relationship with the long term feeding of the immune-deficiency mice.

Study 12: In Vivo Efficacy Study of BCY6136 in the LU-01-0046 NSCLC PDX Model in Balb/c Nude Mice (a) Study Objective The objective of the research is to evaluate the in vivo anti-tumor efficacy of BCY6136 in large LU-01-0046 PDX tumors in Balb/c nude mice.

(b) Experimental Design

| Group | Treatment | n | Dose (mg/kg) | Dosing Volume (μl/g) | Dosing Route | Schedule |
|---|---|---|---|---|---|---|
| 1 | Vehicle | 5 | — | 10 | iv | qw |
| 2 | BCY6136 | 5 | 1 | 10 | iv | qw |
| 3 | BCY6136 | 5 | 3 | 10 | iv | qw |
| 4 | ADC     | 5 | 3 | 10 | iv | qw |

(c) Experimental Methods and Procedures (i) Tumor Inoculation

Each mouse was inoculated subcutaneously at the right flank with LU-01-0046 of tumor fragment (~30 mm$^3$) for tumor development. The treatment was started when the average tumor volume reaches 1039 mm$^3$. The test article administration and the animal numbers in each group are shown in the experimental design table.

(ii) Testing Article Formulation Preparation

| Test article | Conc. (mg/ml) | Formulation |
|---|---|---|
| Vehicle | — | 50 mM Acetate 10% sucrose pH 5 |
| BCY6136 | 0.1 | Dilute 150 μl 1 mg/ml BCY6136 stock with 1350 μl Acetate buffer |
|         | 0.3 | Dilute 450 μl 1 mg/ml BCY6136 stock with 1050 μl Acetate buffer |
| ADC     | 0.3 | Dilute 43 μl 10.47 mg/ml ADC stock solution into 1457 μl with buffer$^2$ |

$^1$Acetate buffer: 50 mM Acetate 10% sucrose pH5
$^2$Dissolve 0.419 g His. hydrochloride in 100 ml water, use 1M HCl adjust PH to 5.5

(d) Results (i) Body Weight change and Tumor Growth Curve

Figure 11:
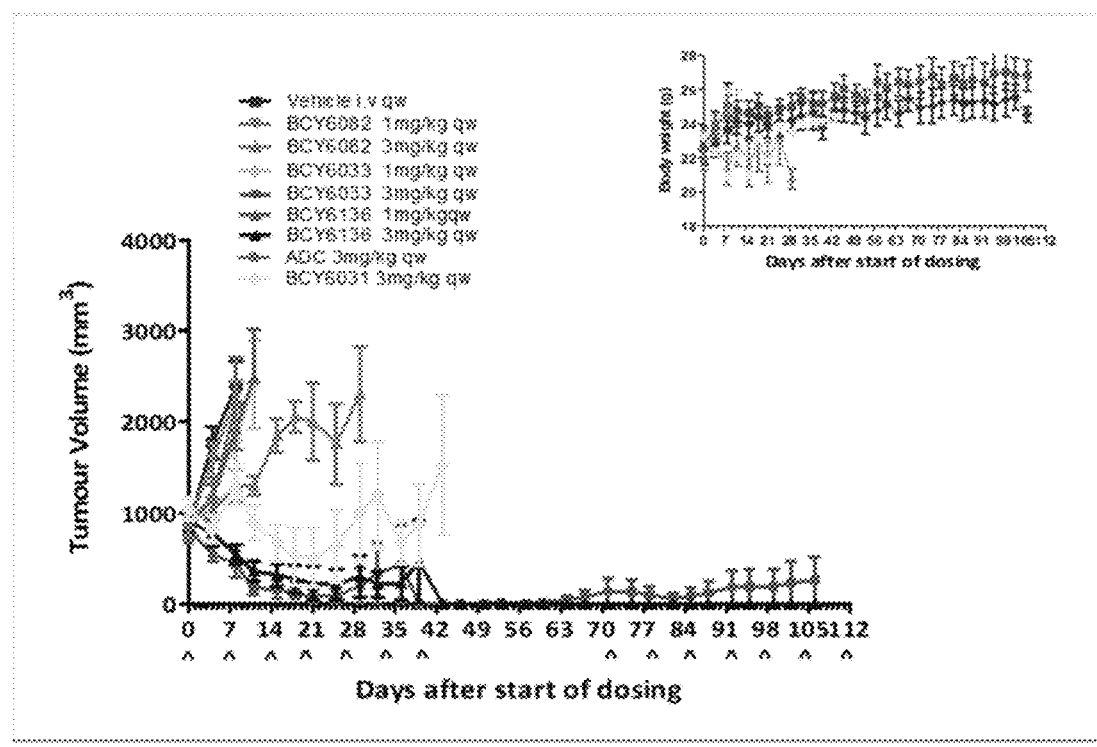
FIG. 11: Body weight changes and tumor volume traces after administering BCY6136 to female Balb/c nude mice bearing LU-01-0046. Data points represent group mean body weight.

Body weight and tumor growth curve are shown in FIG. 11.

(ii) Tumor Volume Trace

Mean tumor volume over time in female Balb/c nude mice bearing LU-01-0046 is shown in Table 30.

TABLE 30

Tumor volume trace over time (BCYs Section)

| | | Days after the start of treatment | | | | | |
|---|---|---|---|---|---|---|---|
| Group | Treatment | 0 | 4 | 8 | 11 | 15 | 18 | 22 |
| 1 | Vehicle, qw 3 mpk, qw | 1044 ± 115 | 1762 ± 178 | 2404 ± 262 | — | — | — | — |

TABLE 30-continued

Tumor volume trace over time (BCYs Section)

| | | Days after the start of treatment | | | | | | |
|---|---|---|---|---|---|---|---|---|
| Group | Treatment | 0 | 4 | 8 | 11 | 15 | 18 | 22 |
| 2 | BCY6136, 1 mpk, qw | 1037 ± 130 | 1163 ± 146 | 1927 ± 283 | 2483 ± 530 | — | — | — |
| 3 | BCY6136, 3 mpk, qw | 1036 ± 100 | 784 ± 146 | 548 ± 107 | 362 ± 110 | 325 ± 122 | 275 ± 152 | 233 ± 187 |
| 4 | ADC, 3 mpk, qw 3 mpk, qw | 1033 ± 114 | 1155 ± 230 | 2200 ± 505 | — | — | — | — |

Note:
the tumor volume trace didn't show after the day 22 for the group 2 and 4.

(iii) Tumor Growth Inhibition Analysis Tumor growth inhibition rate for test articles in the LU-01-0046 PDX model was calculated based on tumor volume measurements at day 22 and day 28 respectively for the two section studies after the start of the treatment.

TABLE 31

Tumor growth inhibition analysis (BCYs section on day 22)

| Group | Treatment | Tumor Volume | T/C$^b$ (%) | TGI (%) | P value |
|---|---|---|---|---|---|
| 1 | Vehicle, qw | 6186 ± 596* | — | — | — |
| 2 | BCY6136, 1 mpk, qw | 4564 ± 981* | 73.8 | 31.4 | p > 0.05 |
| 3 | BCY6136, 3 mpk, qw | 233 ± 187 | 3.8 | 115.6 | p < 0.001 |
| 4 | ADC, 3 mpk, qw | 5446 ± 1250* | 88.0 | 14.2 | p > 0.05 |

$^a$Mean ± SEM;
$^b$Tumor Growth Inhibition is calculated by dividing the average tumor volume of the treated group by the average tumor volume of the control group (T/C).
*Some groups was terminated before day 22, and the tumor size was calculated by exponential growth equation acquisition as below:
Vehicle group: Y = 995.4 × exp (0.1134 × X).
BCY6136, 1 mpk group: Y = 855.0 × exp (0.0974 × X).
ADC, 3 mpk group: Y = 757.4 × exp (0.1312 × X).

(e) Results Summary and Discussion

In this study, the therapeutic efficacy of test articles in large LU-01-0046 tumors was evaluated. The measured body weights and tumor volumes of all treatment groups at various time points are shown in the FIG. 11 and Tables 30 and 31.

In this study, the mean tumor size of vehicle treated mice was calculated as 6186 mm$^3$ on day 22. BCY6136 at 1 mg/kg and ADC at 3 mg/kg didn't show obvious anti-tumor activity when starting treatment from tumor size of 1000 mm$^3$.

BCY6136 (TV=233 mm$^3$, TGI=115.6%, p<0.001) at 3 mg/kg produced significant anti-tumor antitumor activity. In particular, BCY6136 eradicated 2/5 and 4/5 tumors completely.

Study 13: In Vivo Efficacy of BCY6136 in Balb/c Nude Mice Bearing LU-01-0046 NSCLC PDX Model (a) Study Objective The objective of the research was to evaluate the in vivo therapeutic efficacy of BCY6136 in Balb/c nude mice bearing LU-01-0046 NSCLC PDX model.

(b) Experimental Design

| Group | Treatment | n | Dose (mg/kg) | Dosing Route | Schedule |
|---|---|---|---|---|---|
| 1 | Vehicle | 5 | — | i.v. | qw * 2 w |
| 2 | BCY6136 | 5 | 1 | i.v. | qw * 3 w |
| 3 | BCY6136 | 5 | 2 | i.v. | qw * 4 w |
| 4 | BCY6136 | 5 | 3 | i.v. | qw * 4 w |
| 5 | ADC | 5 | 3 | i.v. | qw * 3 w |
| 6 | ADC | 5 | 5 | i.v. | qw * 3 w |

Note:
Groups were terminated when average tumor volume reached over 2000 mm$^3$ and tumors were harvested for FFPE: Group 1 on PG-D14, group 5 on PG-D18, group 2 & 6 on PG-D21 and group 3 & 4 on PG-D31.

(c) Experimental Methods and Procedures (i) Tumor Inoculation

Each mouse was inoculated subcutaneously at the right flank with certain kind of tumor fragment (~30 mm$^3$) for tumor development. The treatments were started when the average tumor volume reached approximately 198 mm$^3$. The test article administration and the animal numbers in each group are shown in the experimental design table.

(ii) Testing Article Formulation Preparation

| Gr | Compounds | Dose (mg/kg) | Con. (mg/ml) | Formulation |
|---|---|---|---|---|
| 1 | Vehicle | — | — | 50 mM Acetate, 10% Sucrose pH 5 (without DMSO) |
| 2 | BCY6136 | 1 | 0.1 | Dissolve 10.93 mg BCY6136 in 10.766 ml vehicle, ultrasonic simply to make the 1 mg/ml BCY6136 stock solution Dilute 150 μl 1 mg/ml BCY6136 stock solution with 1350 μl vehicle |
| 3 | BCY6136 | 2 | 0.2 | Dilute 300 μl 1 mg/ml BCY6136 stock solution with 1200 μl vehicle |
| 4 | BCY6136 | 3 | 0.3 | Dilute 450 μl 1 mg/ml BCY6136 stock solution with 1050 μl vehicle |

-continued

| Gr | Compounds | Dose (mg/kg) | Con. (mg/ml) | Formulation |
|---|---|---|---|---|
| Buffer 2: Dissolve 0.419 g His. hydrochloride in 100 ml water, use 1M HCl adjust pH to 5.5 |||||
| 5 | ADC | 3 | 0.3 | Dilute 43 μl 10.47 mg/ml ADC stock solution with 1457 μl with buffer 2 |
| 6 | ADC | 5 | 0.5 | Dilute 71.6 μl 10.47 mg/ml ADC stock solution with1428.4 μl with buffer 2 |

Note:
The dosing formulation frequently is fresh prepared timely.

(iii) Sample Collection

Groups were terminated when average tumor volume reached over 2000 mm³ and tumors were harvested for FFPE after the last measurement: Group 1 on PG-D14, group 5 on PG-D18, group 2 & 6 on PG-D21 and group 3 & 4 on PG-D31.

(d) Results (i) Body Weight Change and Tumor Growth Curve

Figure 12:
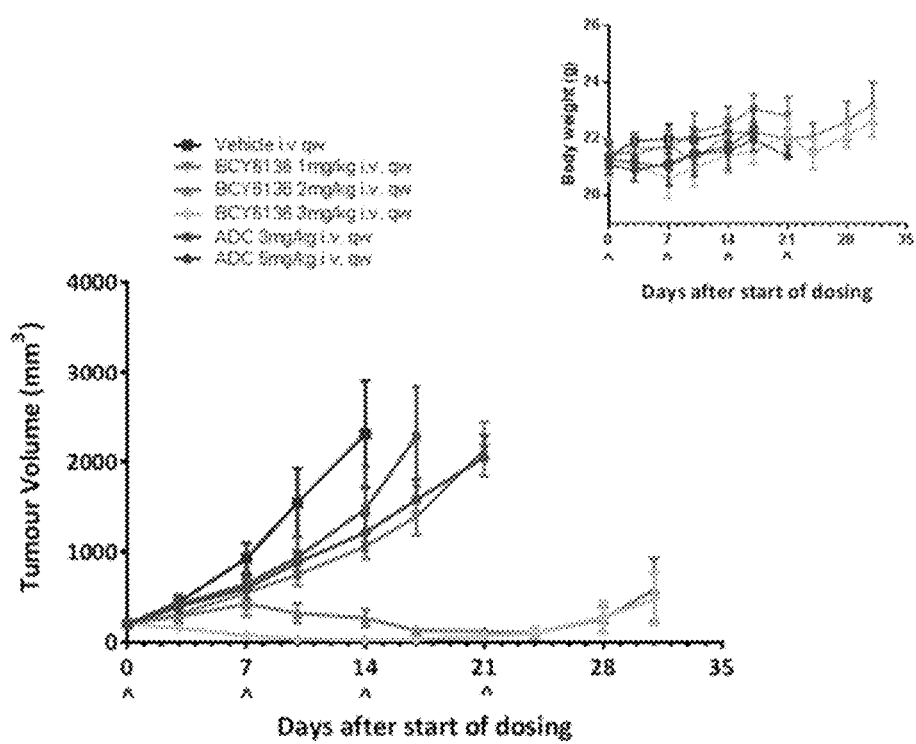
FIG. 12: Body weight changes and tumor volume traces after administering BCY6136 or ADC to female Balb/c nude mice bearing LU-01-0046 NSCLC PDX model. Data points represent group mean body weight.

Body weight and tumor growth curve are shown in FIG. 12.

(ii) Tumor Volume Trace

Mean tumor volume over time in female Balb/c nude mice bearing LU-01-0046 NSCLC PDX model is shown in Table 32.

TABLE 32

Tumor volume trace over time (mm³)

| | Gr | | | | | |
|---|---|---|---|---|---|---|
| | 1 | 2 | 3 | 4 | 5 | 6 |
| Treatment | Vehicle qw | BCY6136 1 mpk, qw | BCY6136 2 mpk, qw | BCY6136 3 mpk, qw | ADC 3 mpk, qw | ADC 5 mpk, qw |
| 0 | 201 ± 37 | 198 ± 39 | 201 ± 40 | 200 ± 46 | 195 ± 28 | 195 ± 40 |
| 3 | 441 ± 82 | 310 ± 59 | 283 ± 77 | 155 ± 40 | 418 ± 99 | 389 ± 68 |
| 7 | 927 ± 171 | 547 ± 88 | 423 ± 132 | 74 ± 19 | 643 ± 159 | 596 ± 116 |
| 10 | 1546 ± 377 | 747 ± 121 | 321 ± 108 | 31 ± 8 | 938 ± 230 | 882 ± 134 |
| 14 | 2307 ± 594 | 1058 ± 140 | 264 ± 95 | 26 ± 11 | 1475 ± 466 | 1215 ± 193 |
| 17 | — | 1390 ± 205 | 127 ± 41 | 26 ± 13 | 2281 ± 556 | 1576 ± 228 |
| 21 | — | 2138 ± 301 | 118 ± 34 | 64 ± 42 | — | 2049 ± 242 |
| 24 | — | — | 101 ± 40 | 99 ± 63 | — | — |
| 28 | — | — | 255 ± 140 | 276 ± 176 | — | — |
| 31 | — | — | 582 ± 346 | 477 ± 283 | — | — |

(iii) Tumor Growth Inhibition Analysis

Tumor growth inhibition rate for test articles in Balb/c nude mice bearing LU-01-0046 PDX model was calculated based on tumor volume measured on PG-D14.

TABLE 33

Tumor growth inhibition analysis

| Gr | Treatment | Tumor Volume (mm³)[a] | T/C (%)[b] | TGI (%)[c] | P value compared with vehicle |
|---|---|---|---|---|---|
| 1 | Vehicle qw | 2307 ± 594 | — | — | — |
| 2 | BCY6136 1 mpk, qw | 1058 ± 140 | 45.9 | 59.1 | p < 0.05 |
| 3 | BCY6136 2 mpk, qw | 264 ± 95 | 11.4 | 97.0 | p < 0.001 |
| 4 | BCY6136 3 mpk, qw | 26 ± 11 | 1.1 | 108.3 | p < 0.001 |
| 5 | ADC 3 mpk, qw | 1475 ± 466 | 63.9 | 39.2 | p > 0.05 |
| 6 | ADC 5 mpk, qw | 1215 ± 193 | 52.7 | 51.6 | p > 0.05 |

[a]Mean ± SEM.
[b]Tumor Growth Inhibition was calculated by dividing the group average tumor volume for the treated group by the group average tumor volume for the control group (T/C).
[c]TGI was calculated for each group using the formula: TGI (%) = [1 − ($T_i$ − $T_0$)/($V_i$ − $V_0$)] × 100

(e) Results Summary and Discussion

In the present study, the therapeutic efficacy of test articles in the LU-01-0046 PDX model was evaluated. The measured body weights and tumor volumes of all treatment groups at various time points were shown in the FIG. 12 and Tables 32 and 33.

The mean tumor size of vehicle treated mice reached 2307 mm$^3$ on PG-D14. BCY6136 at 1 mg/kg (TV=1058 mm$^3$, TGI=59.1%, p<0.05), at 2 mg/kg (TV=264 mm$^3$, TGI=97.0%, p<0.001) and at 3 mg/kg (TV=26 mm$^3$, TGI=108.3%, p<0.001) produced dose-dependent antitumor activity. ADC at 3 mg/kg and 5 mg/kg did not show obvious antitumor activity (p>0.05).

In this study, all of the group's animals maintained the body weight well.

Study 14: In Vivo Efficacy Study of BCY6136, BCY6173 and BCY6175 in the LU 0046 NSCLC PDX Model in Balb/c Nude Mice (a) Study Objective The objective of the research is to evaluate the in vivo anti-tumor efficacy of test articles in the LU-01-0046 NSCLC PDX model in Balb/c nude mice.

(b) Experimental Design

| Group | Treatment | n | Dose (mg/kg) | Dosing Volume (μl/g) | Dosing Route | Schedule |
|---|---|---|---|---|---|---|
| | | | Part 1 | | | |
| 1 | Vehicle | 5 | — | 10 | iv | qw |
| 2 | BCY6136 | 5 | ½ | 10 | iv | qw |
| 3 | BCY6136 | 5 | 3 | 10 | iv | qw |
| | | | Part 2 | | | |
| 4 | Vehicle | 5 | — | 10 | iv | qw |
| 5 | BCY6173 | 5 | 1 | 10 | iv | qw |
| 6 | BCY6173 | 5 | 3 | 10 | iv | qw |
| 7 | BCY6175 | 5 | 3 | 10 | iv | qw |

(c) Experimental Methods and Procedures (i) Tumor Inoculation

Each mouse was inoculated subcutaneously at the right flank with LU-01-0046 of tumor fragment (~30 mm$^3$) for tumor development. The treatment was started when the average tumor volume reaches 200 mm$^3$ for part 1 study and 192 mm$^3$ for part 2 study. The test article administration and the animal numbers in each group are shown in the experimental design table.

(ii) Testing Article Formulation Preparation

| Test article | Conc. (mg/ml) | Formulation |
|---|---|---|
| Vehicle | — | 50 mM Acetate 10% sucrose pH 5 |
| BCY6136 | 0.1 | Dilute 150 μl 1 mg/ml BCY6136 stock with 1350 μl Acetate buffer |
| | 0.3 | Dilute 450 μl 1 mg/ml BCY6136 stock with 1050 μl Acetate buffer |
| BCY6173 | 0.1 | Dissolve 3.65 mg BCY6173 in 3.5 ml Acetate buffer to make 1 mg/ml stock. Dilute 150 μl 1 mg/ml BCY6173 with 1350 μl Acetate buffer |
| | 0.3 | Dilute 450 μl 1 mg/ml BCY6173 stock with 1050 μl Acetate buffer |
| BCY6175 | 0.3 | Dissolve 3.02 mg BCY6175 in 2.9 ml Acetate buffer to make 1 mg/ml stock. Dilute 450 μl 1 mg/ml BCY6175 with 1050 μl Acetate buffer |

[1]Acetate buffer: 50 mM Acetate 10% sucrose pH 5

(d) Results

Body Weight Change and Tumor Growth Curve

Figure 13:
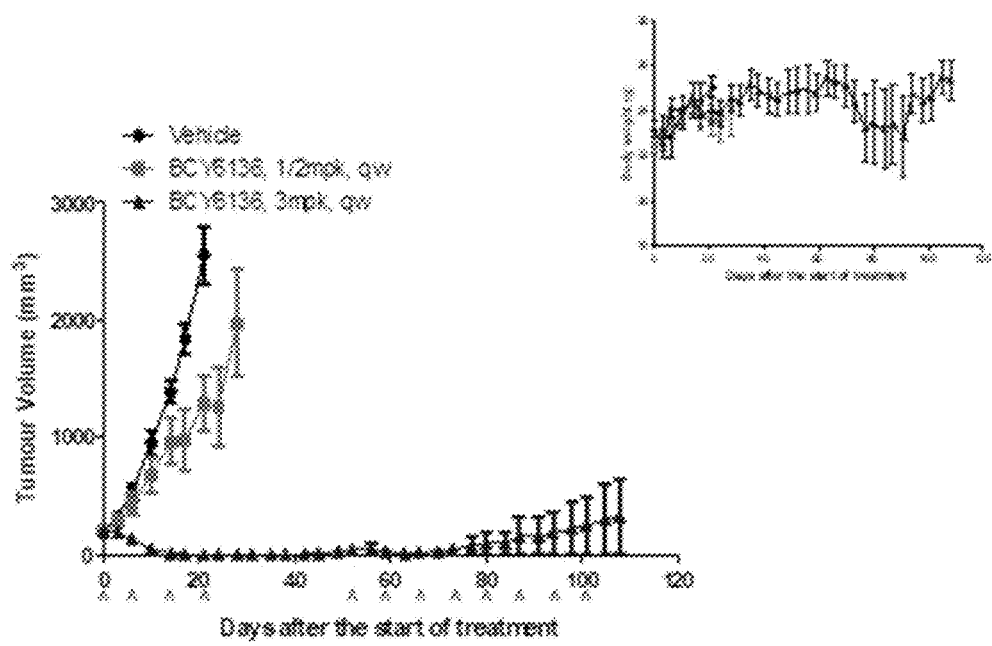
FIGS. 13 to 15: Body weight changes and tumor volume traces after administering BCY6136 (FIG. 13), BCY6173 (FIG. 14) and BCY6175 (FIG. 15) to female Balb/c nude mice bearing LU-01-0046. Data points represent group mean body weight.
Figure 14:
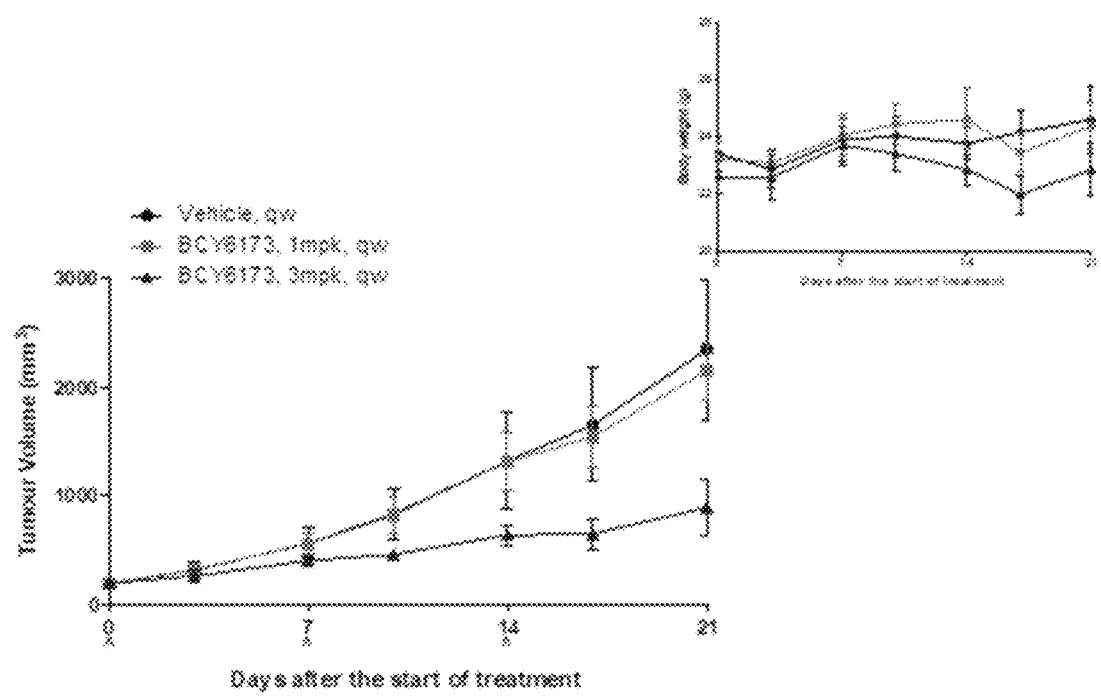
Figure 15:
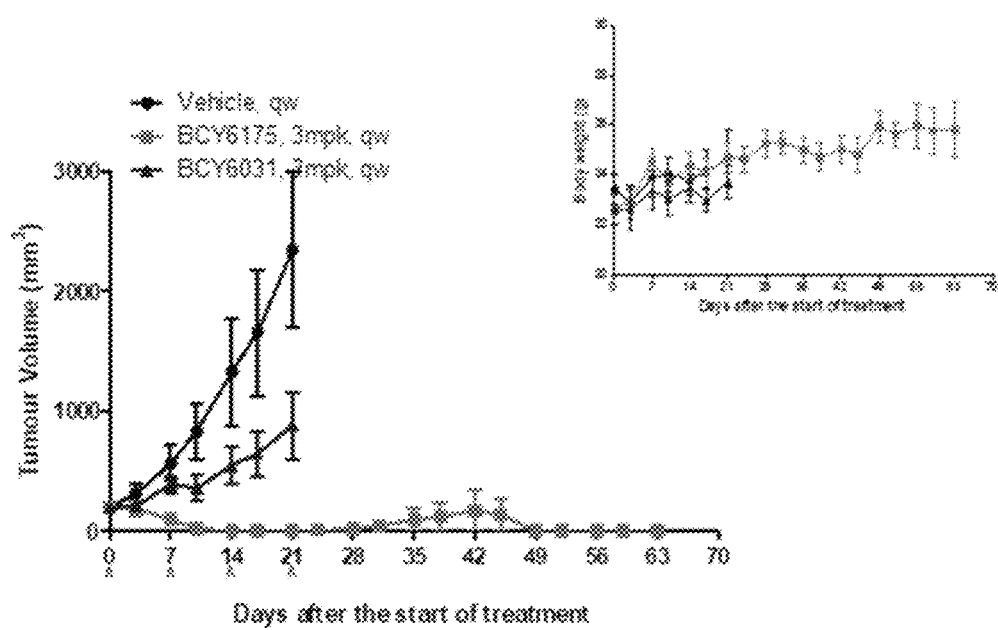

Body weight and tumor growth curve are shown in FIGS. 13 to 15.

(ii) Tumor Volume Trace

Mean tumor volume on day 21 after the start of treatment in female Balb/c nude mice bearing LU-01-0046 is shown in Tables 34 and 35.

TABLE 34

Tumor volume trace over time (Part 1)

| | | Days after the start of treatment | | | | | |
|---|---|---|---|---|---|---|---|
| Gr | Treatment | 0 | 3 | 6 | 10 | 14 | 17 | 21 |
| 1 | Vehicle, qw | 202 ± 26 | 328 ± 48 | 536 ± 68 | 953 ± 107 | 1386 ± 97 | 1833 ± 132 | 2551 ± 242 |
| 2 | BCY6136, 1 mpk, qw | 200 ± 33 | 293 ± 56 | 426 ± 91 | 682 ± 151 | 964 ± 194 | 976 ± 258 | 1285 ± 234 |
| 3 | BCY6136, 3 mpk, qw | 201 ± 33 | 194 ± 31 | 135 ± 27 | 52 ± 18 | 13 ± 9 | 4 ± 4 | 0 ± 0 |

TABLE 35

Tumor volume trace over time (Part 2)

| | | Days after the start of treatment | | | | | |
|---|---|---|---|---|---|---|---|
| Gr | Treatment | 0 | 3 | 7 | 10 | 14 | 17 | 21 |
| 4 | Vehicle, qw | 192 ± 30 | 311 ± 83 | 562 ± 146 | 830 ± 230 | 1320 ± 444 | 1652 ± 528 | 2342 ± 651 |
| 5 | BCY6173, 1 mpk, qw | 191 ± 33 | 318 ± 58 | 553 ± 88 | 817 ± 165 | 1314 ± 276 | 1546 ± 276 | 2151 ± 262 |
| 6 | BCY6173, 3 mpk, qw | 192 ± 37 | 259 ± 51 | 400 ± 53 | 455 ± 28 | 636 ± 92 | 646 ± 138 | 890 ± 260 |
| 7 | BCY6175, 3 mpk, qw | 192 ± 42 | 186 ± 57 | 92 ± 38 | 19 ± 11 | 0 ± 0 | 0 ± 0 | 0 ± 0 |

(iii) Tumor Growth Inhibition Analysis

Tumor growth inhibition rate for test articles in the LU-01-0046 PDX model was calculated based on tumor volume measurements at day 21 after the start of the treatment.

TABLE 36

Tumor growth inhibition analysis (Part 1)

| Group | Treatment | Tumor Volume | T/C[b] (%) | TGI (%) | P value |
|---|---|---|---|---|---|
| 1 | Vehicle, qw | 2551 ± 242 | — | — | — |
| 2 | BCY6136, 1 mpk, qw | 1285 ± 234 | 50.4 | 53.9 | p < 0.001 |
| 3 | BCY6136, 3 mpk, qw | 0 ± 0 | 0.0 | 108.5 | p < 0.001 |

[a]Mean ± SEM;
[b]Tumor Growth Inhibition is calculated by dividing the group average tumor volume for the treated group by the group average tumor volume for the control group (T/C).

TABLE 37

Tumor growth inhibition analysis (Part 2)

| Group | Treatment | Tumor Volume | T/C[b] (%) | TGI (%) | P value |
|---|---|---|---|---|---|
| 4 | Vehicle, qw | 2342 ± 651 | — | — | — |
| 5 | BCY6173, 1 mpk, qw | 2151 ± 262 | 91.8 | 8.9 | p > 0.05 |
| 6 | BCY6173, 3 mpk, qw | 890 ± 260 | 38.0 | 67.5 | p < 0.05 |
| 7 | BCY6175, 3 mpk, qw | 0 ± 0 | 0.0 | 108.9 | p < 0.001 |

[a]Mean ± SEM;
[b]Tumor Growth Inhibition is calculated by dividing the group average tumor volume for the treated group by the group average tumor volume for the control group (T/C).

(e) Results Summary and Discussion

In this study, the therapeutic efficacy of test articles in the LU-01-0046 PDX model was evaluated. The measured body weights and tumor volumes of all treatment groups at various time points are shown in the FIGS. 13 to 15 and Tables 34 to 37.

In part 1 study, the mean tumor size of vehicle treated mice reached 2551 mm$^3$ on day 21 after the start of treatment.

BCY6136 at ½ mg/kg, qw (TV=1285 mm$^3$, TGI=53.9%, p<0.001) produced significant anti-tumor activity, but didn't exhibit any tumor regression. BCY6136 at 3 mg/kg, qw (TV=0 mm$^3$, TGI=108.5%, p<0.001) completely eradicated the tumors, 1 of 5 tumors respectively in BCY6136 3 mg/kg groups showed regrowth after the dosing suspension and the tumors were resistant to BICY6136 treatment when resuming the dosing. The remaining tumors in the BCY6136 groups (⅘ for each group) showed no regrowth after 80 days of dosing suspension. In part 2 study, the mean tumor size of vehicle treated mice reached 2342 mm$^3$ on day 21 after the start of treatment. BCY6173 at 1 mg/kg, qw (TV=2151 mm$^3$, TGI=8.9%, p>0.05) did not show anti-tumor antitumor activity. BCY6173 at 3 mg/kg, qw (TV=890 mm$^3$, TGI=67.5%, p<0.05) produced obvious anti-tumor activity.

BCY6175 at 3 mg/kg, qw (TV=0 mm$^3$, TGI=108.9%, p<0.001) completely eradicated 4/5 tumors on day 14.

Study 15: In Vivo Efficacy Study of BCY6136 in the LU-01-0412 NSCLC PDX Model in Balb/c Nude Mice (a) Study Objective The objective of the project is to evaluate the in vivo therapeutic efficacy of BCY6136 in the LU-01-0412 NSCLC PDX model in BALB/c nude mice.

(b) Experimental Design

| Gr | Treatment | n | Dose (mg/kg) | Dosing Volume (μl/g) | Dosing Route | Schedule |
|---|---|---|---|---|---|---|
| 1 | Vehicle | 6 | — | 10 | iv | Qw, 4 |
| 2 | BCY6136 | 6 | 1 | 10 | iv | Qw, 4 |
| 3 | BCY6136 | 6 | 3 | 10 | iv | Qw, 4 |
| 4 | BCY8245 | 6 | 3 | 10 | iv | Qw, 4 |
| 5 | BCY8781 | 6 | 3 | 10 | iv | Qw, 4 |

(c) Experimental Methods and Procedures (i) Tumor Inoculation

Each mouse was inoculated subcutaneously at the right flank with LU-01-0412 tumor fragment (~30 mm$^3$) for tumor development. Animals were randomized when the average tumor volume reached 159 mm$^3$. The test article administration and the animal numbers in each group were shown in the experimental design table.

(ii) Testing Article Formulation Preparation

| Test article | Conc. (mg/ml) | Formulation |
|---|---|---|
| Vehicle | — | 25 mM Histidine 10% sucrose pH 7 |
| BCY6136 | 1 | Dissolve 6.06 mg BCY6136 in 5.969 ml 50 mM Acetate/acetic acid pH 5 10% sucrose |
| | 0.1 | Dilute 180 μl 1 mg/ml BT5528 with 1620 μl 50 mM Acetate/acetic acid pH 5 10% sucrose |
| | 0.3 | Dilute 540 μl 1 mg/ml BT5528 with 1260 ul 50 mM Acetate/acetic acid pH 5 10% sucrose |
| BCY8245 | 1 | Dissolve 4.15 mg BCY8245 powder in 4.121 ml vehicle buffer |
| | 0.3 | Dilute 540 μl 1 mg/ml BCY8245 with 1260 μl vehicle buffer |
| BCY8781 | 1 | Dissolve 4.08 mg BCY8781 powder in 80.8 μl DMSO, then dilute to 1 mg/ml with 3.958 vehicle buffer |
| | 0.3 | Dilute 540 μl 1 mg/ml BCY8781 with 1260 μl vehicle buffer |

(iii) Sample Collection

Plasma from vehicle and 3 extra mice treated with BCY6136, BCY8245 and BCY8781 were collected at 30 min and 24 h post dosing. Tumor from vehicle and 3 extra mice treated with BCY6136, BCY8245 and BCY8781 were collected at 24 h post dosing.

(d) Results (i) Body Weight change and Tumor Growth Curve

Figure 16:
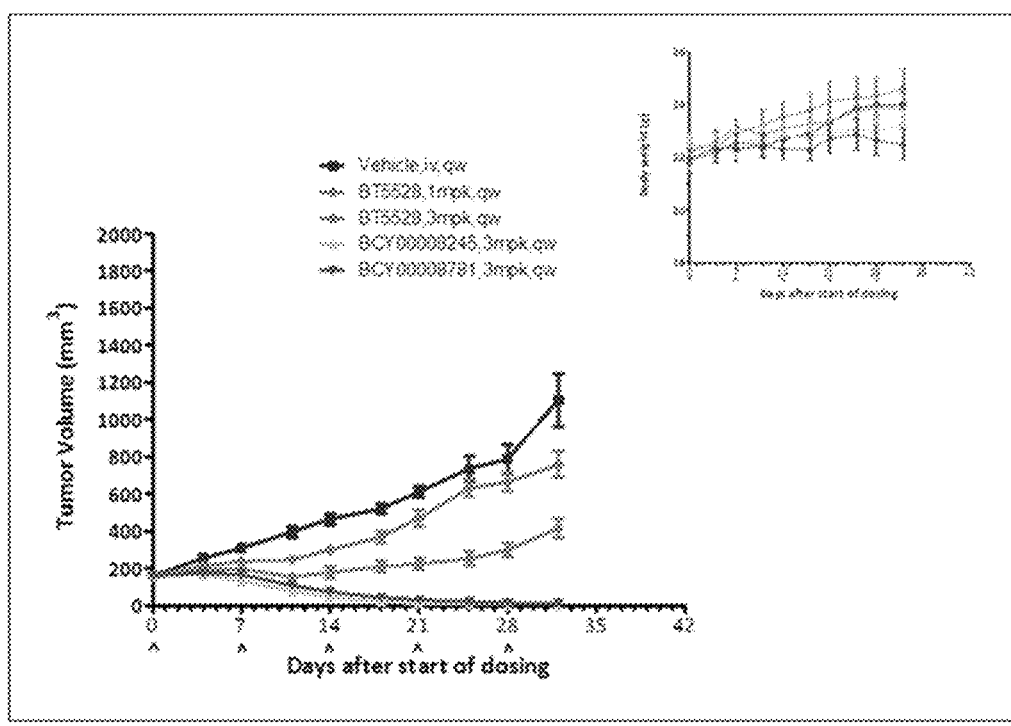
FIG. 16: Body weight changes and tumor volume traces after administering BCY6136 (referred to in FIG. 16 as BT5528), BCY8245 or BCY8781 to female BALB/c nude mice bearing LU-01-0412 xenograft. Data points represent group mean tumor volume (left panel) and body weight (right panel).

Body weight and tumor growth curves are shown in FIG. 16.

(ii) Tumor Volume Trace

Mean tumor volume over time in female BALB/c nude mice bearing LU-01-0412 xenograft is shown in Table 38.

TABLE 38

Tumor volume trace over time

| Days | Group 1 Vehicle Qw * 4 | Group 2 BCY6136 1 mpk, Qw * 4 | Group 3 BCY6136 3 mpk, Qw * 4 | Group 4 BCY8245 3 mpk, Qw * 4 | Group 5 BCY8781 3 mpk, Qw * 4 |
|---|---|---|---|---|---|
| 0  | 159 ± 11   | 159 ± 13 | 159 ± 11 | 159 ± 12 | 159 ± 11 |
| 4  | 255 ± 12   | 214 ± 16 | 197 ± 16 | 168 ± 18 | 176 ± 21 |
| 7  | 309 ± 20   | 237 ± 16 | 195 ± 16 | 132 ± 10 | 167 ± 13 |
| 11 | 395 ± 31   | 246 ± 19 | 156 ± 18 | 78 ± 4   | 107 ± 15 |
| 14 | 464 ± 31   | 300 ± 18 | 177 ± 29 | 45 ± 5   | 72 ± 12  |
| 18 | 521 ± 26   | 369 ± 32 | 210 ± 32 | 21 ± 2   | 44 ± 8   |
| 21 | 611 ± 33   | 470 ± 46 | 225 ± 32 | 11 ± 1   | 31 ± 6   |
| 25 | 737 ± 68   | 632 ± 47 | 252 ± 37 | 6 ± 1    | 20 ± 6   |
| 28 | 788 ± 80   | 664 ± 52 | 299 ± 37 | 2 ± 1    | 14 ± 5   |
| 32 | 1104 ± 142 | 758 ± 70 | 416 ± 52 | 1 ± 1    | 12 ± 5   |

(iii) Tumor Growth Inhibition Analysis

Tumor growth inhibition rate for BCY6136, BCY8245 and BCY8781 in the LU-01-0412 xenograft model was calculated based on tumor volume measurements on day 32 after the start of the treatment.

TABLE 39

Tumor growth inhibition analysis

| Group | Treatment | Tumor Volume $(mm^3)^a$ | T/C$^b$ (%) | TGI (%) | P value |
|---|---|---|---|---|---|
| 1 | Vehicle, qw * 4     | 1104 ± 142 | —    | —     | —         |
| 2 | BCY6136, 1 mpk, qw * 4 | 758 ± 70   | 68.6 | 36.7  | p < 0.05  |
| 3 | BCY6136, 3 mpk, qw * 4 | 416 ± 52   | 37.6 | 72.9  | p < 0.001 |
| 4 | BCY8245, 3 mpk, qw * 4 | 1 ± 1      | 0.1  | 116.8 | p < 0.001 |
| 5 | BCY8781, 3 mpk, qw * 4 | 12 ± 5     | 1.0  | 115.6 | p < 0.001 |

$^a$Mean ± SEM;
$^b$Tumor Growth Inhibition is calculated by dividing the group average tumor volume for the treated group by the group average tumor volume for the control group (T/C).

(e) Results Summary and Discussion

In this study, the therapeutic efficacy of BCY6136, BCY8245 and BCY8781 in the LU-01-0412 xenograft model was evaluated. The measured body weight and tumor volume of all treatment groups at various time points are shown in FIG. 16 and Tables 38 and 39.

The mean tumor volume of vehicle treated mice reached 1104 mm$^3$ on day 32 after the start of treatment. BCY6136 at 1 mg/kg, qw*4 (TV=758 mm$^3$, TGI=36.7%, p<0.05) and 3 mg/kg, qw*4 (TV=416 mm$^3$, TGI=72.9%, p<0.001) produced dose-dependent antitumor activity, but didn't show any tumor regression. BCY8245 at 3 mg/kg, qw*4 (TV=1 mm$^3$, TGI=116.8%, p<0.001) and BCY8781 at 3 mg/kg, qw*4 (TV=12 mm$^3$, TGI=115.6%, p<0.001) regressed the tumors obviously. Among them, 5 of 6 tumor treated with BCY8245 3 mg/kg and 2 of 6 tumor treated with d BCY8781 3 mg/kg were completely eradicated on day 32.

In this study, animals in all groups maintained the body weight well.

Study 16: In Vivo Efficacy Study of BCY6136 in Treatment of LU-01-0486 PDX Model in Balb/c Nude Mice (a) Study Objective The objective of the research is to evaluate the in vivo anti-tumor efficacy of BCY6136 in the LU-01-0486 PDX model in Balb/c nude mice.

(b) Experimental Design

| Gr | Treatment | n | Dose (mg/kg) | Dosing Volume (μl/g) | Dosing Route | Schedule |
|---|---|---|---|---|---|---|
| 1 | Vehicle | 5 | —  | 10 | iv | qw |
| 2 | BCY6136 | 5 | 1  | 10 | iv | qw |
| 3 | BCY6136 | 5 | 2  | 10 | iv | qw |
| 4 | BCY6136 | 5 | 3  | 10 | iv | qw |

(c) Experimental Methods and Procedures (i) Tumor Inoculation

Each mouse was inoculated subcutaneously at the right flank with LU-01-0486 of tumor fragment (~30 mm$^3$) for tumor development. The treatment was started when the average tumor volume reached 180 mm$^3$ for efficacy study. The test article administration and the animal number in each group are shown in the experimental design table.

(ii) Testing Article Formulation Preparation

| Test article | Conc. (mg/ml) | Formulation |
|---|---|---|
| Vehicle | — | 50 mM Acetate 10% sucrose pH 5 |
| BCY6136 | 0.3 | 0.3 mg/ml BCY6136 was prepared as described in Study 10 |
|         | 0.2 | Dilute 940 μl 0.3 mg/ml BCY6136 with 470 μl Acetate buffer¹ |
|         | 0.1 | Dilute 470 μl 0.3 mg/ml BCY6136 with 940 μl Acetate buffer |

1Acetate buffer: 50 mM Acetate 10% sucrose pH 5

(d) Results (i) Body Weight change and Tumor Growth Curve

Figure 17:
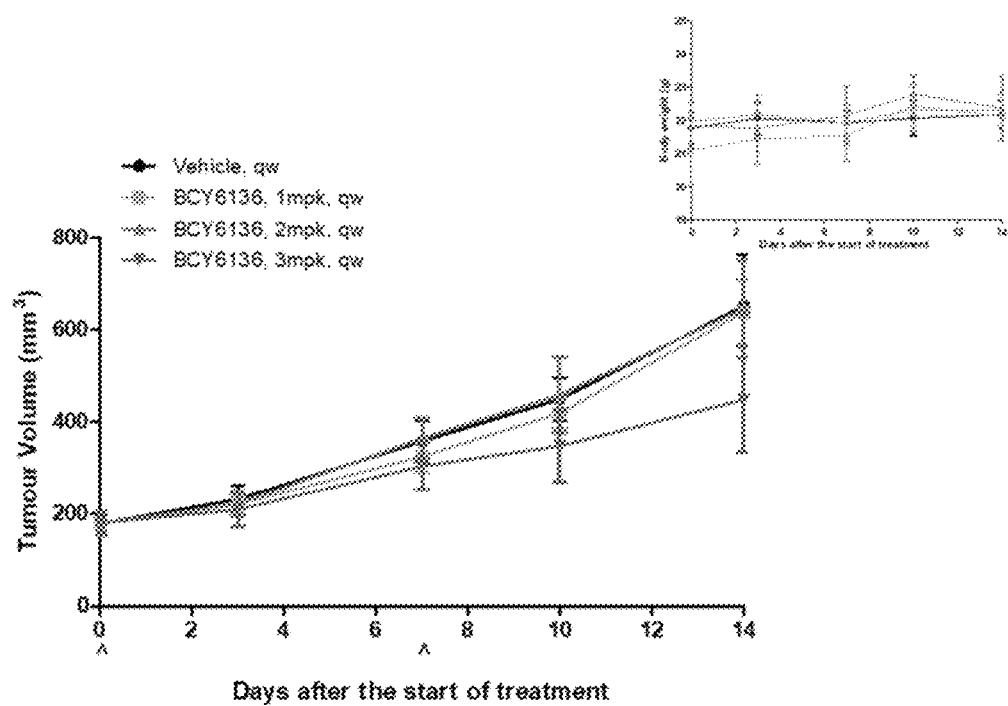
FIG. 17: Body weight changes and tumor volume traces after administering BCY6136 to female Balb/c nude mice bearing LU-01-0486 xenograft. Data points represent group mean body weight.

Body weight and tumor growth curve are shown in FIG. 17.

(ii) Tumor Volume Trace

Mean tumor volume on day 14 after the start of treatment in female Balb/c nude mice bearing LU-01-0486 xenograft is shown in Table 40.

TABLE 40

Tumor volume trace over time

| Group | Treatment | \multicolumn{5}{c}{Days after the start of treatment} |
|---|---|---|---|---|---|---|
| | | 0 | 3 | 7 | 10 | 14 |
| 1 | Vehicle, qw | 179 ± 20 | 232 ± 30 | 358 ± 45 | 450 ± 47 | 651 ± 112 |
| 2 | BCY6136, 1 mpk, qw | 180 ± 23 | 221 ± 20 | 326 ± 34 | 420 ± 34 | 638 ± 71 |
| 3 | BCY6136, 2 mpk, qw | 179 ± 27 | 222 ± 26 | 365 ± 44 | 459 ± 82 | 645 ± 105 |
| 4 | BCY6136, 3 mpk, qw | 180 ± 25 | 209 ± 37 | 304 ± 51 | 348 ± 77 | 449 ± 115 |

(iii) Tumor Growth Inhibition Analysis

Tumor growth inhibition rate for BCY6136 in the LU-01-0486 PDX model was calculated based on tumor volume measurement at day 14 after the start of the treatment.

TABLE 41

Tumor growth inhibition analysis

| Group | Treatment | Tumor Volume (mm$^3$)$^a$ | T/C$^b$ (%) | TGI (%) | P value |
|---|---|---|---|---|---|
| 1 | Vehicle, qw | 651 ± 112 | — | — | — |
| 2 | BCY6136, 1 mpk, qw | 638 ± 71 | 98.0 | 3.0 | p > 0.05 |
| 3 | BCY6136, 2 mpk, qw | 645 ± 105 | 99.1 | 1.2 | p > 0.05 |
| 4 | BCY6136, 3 mpk, qw | 449 ± 115 | 68.9 | 43.1 | p > 0.05 |

$^a$Mean ± SEM;
$^b$Tumor Growth Inhibition is calculated by dividing the group average tumor volume for the treated group by the group average tumor volume for the control group (T/C).

(e) Results Summary and Discussion

In this study, the therapeutic efficacy of BCY6136 in LU-01-0486 PDX model was evaluated. The measured body weight and tumor volume of all treatment groups at various time points are shown in the FIG. 17 and Tables 40 and 41.

In this study, the mean tumor volume of vehicle treated mice reached 651 mm$^3$ on day 14 after the start of treatment. BCY6136 at 1 mg/kg, qw (TV=638 mm$^3$, TGI=3.0%, p>0.05) and 2 mg/kg, qw (TV=645 mm$^3$, TGI=1.2%, p>0.05) didn't show any anti-tumor activity. BCY6136 at 3 mg/kg, qw (TV=449 mm$^3$, TGI=43.1%, p>0.05) produced slight anti-tumor activity without statistical significance.

Study 17: In Vivo Efficacy Test of BCY6136 in Treatment of MDA-MB-231-luc Xenograft in Balb/c Nude Mice (a) Study Objective The objective of the research was to evaluate the in vivo anti-tumor efficacy of BCY6136 in treatment of MDA-MB-231-luc xenograft model in Balb/c nude mice.

(b) Experimental Design

| Gr | Treatment | n | Dose (mg/kg) | Dosing Volume (μl/g) | Dosing Route | Schedule |
|---|---|---|---|---|---|---|
| 1 | Vehicle | 3 | — | 10 | iv | qw |
| 2 | BCY6136 | 3 | 1 | 10 | iv | qw |
| 3 | BCY6136 | 3 | 2 | 10 | iv | qw |
| 4 | BCY6136 | 3 | 2 | 10 | iv | qw |

(c) Experimental Methods and Procedures (i) Cell Culture

The cells growing in an exponential growth phase were harvested and counted for tumor inoculation.

(ii) Tumor Inoculation

Each mouse was inoculated subcutaneously at the right flank with MDA-MB-231-luc tumor cells (10×10^6) in 0.1 ml of PBS with 0.1 ml matrigel for tumor development. 36 animals were randomized when the average tumor volume reached 159 mm$^3$. The test article administration and the animal numbers in each group were shown in the experimental design table.

(iii) Testing Article Formulation Preparation

| Treatment | Dose (mg/ml) | Formulation |
|---|---|---|
| Vehicle | | 50 mM Acetate, 10% sucrose pH = 5 |
| BCY6136 | 1 | Dissolve 3.79 mg BCY6136 into 3.695 ml formulation buffer |
| | 0.3 | Dilute 270 μl 1 mg/ml BCY6136 into 630 μl formulation buffer |
| | 0.2 | Dilute 180 μl 1 mg/ml BCY6136 into 720 μl formulation buffer |
| | 0.1 | Dilute 90 μl 1 mg/ml BCY6136 into 810 μl formulation buffer |

(iv) Sample Collection

On PG-D33, we collected and fixed the tumors of Group 2 for FFPE.

At the end of study, we collected and fixed the tumors of Group 3 and 4 for FFPE.

(d) Results (i) Body Weight Change and Tumor Growth Curve

Figure 18:
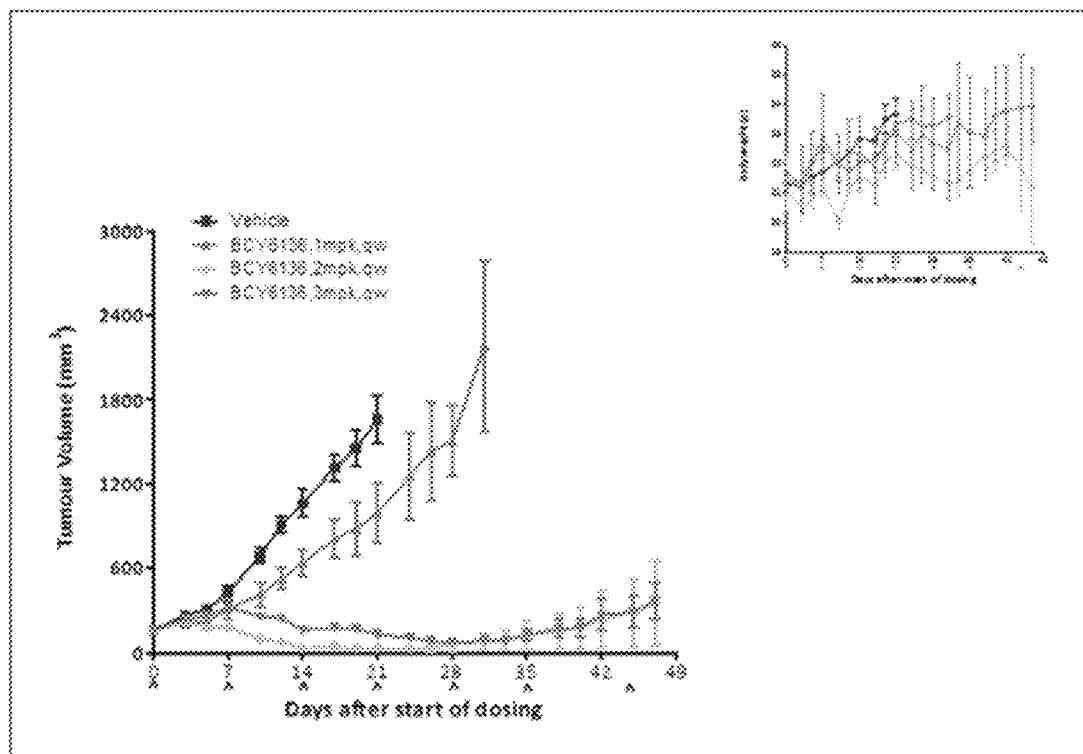
FIG. 18: Body weight changes and tumor volume trace after administering BCY6136 to female Balb/c nude mice bearing MDA-MB-231-luc xenograft. Data points represent group mean tumor volume and body weight.
Figure 19:
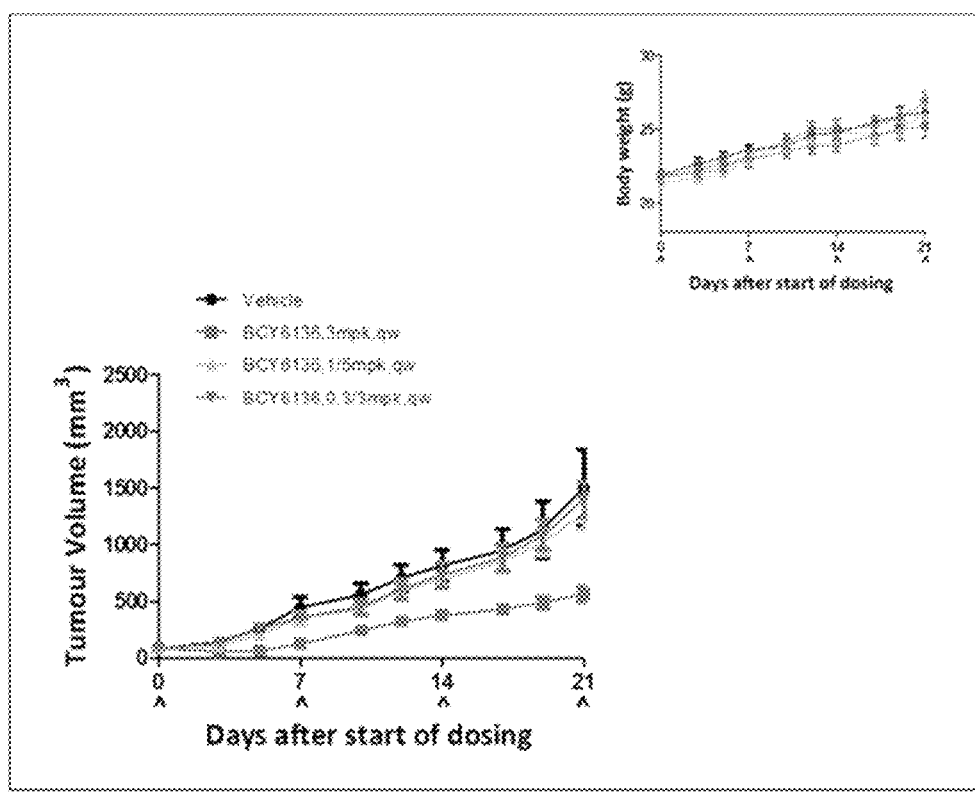
FIG. 19: Body weight changes and tumor volume traces after administering BCY6136 to female BALB/c mice bearing EMT-6 syngeneic. Data points represent group mean body weight. The dosage of group 3 and group 4 was changed to 5 mpk and 3 mpk from Day 14.

Body weight and tumor growth are shown in FIG. 18.

(ii) Tumor Volume Trace

Mean tumor volume over time in female Balb/c nude mice bearing MDA-MB-231-luc xenograft is shown in Tables 42 to 44.

TABLE 42

Tumor volume trace (PG-D 0~PG-D 17)

| | | Days after the start of treatment | | | | | | |
|---|---|---|---|---|---|---|---|---|
| Gr. | Treatment | 0 | 2 | 4 | 7 | 9 | 11 | 14 | 17 |
| 1 | Vehicle, qw | 159 ± 14 | 269 ± 8 | 306 ± 19 | 425 ± 52 | 688 ± 54 | 908 ± 54 | 1064 ± 98 | 1315 ± 95 |
| 2 | BCY6136, 1 mpk, qw | 159 ± 10 | 226 ± 36 | 221 ± 54 | 310 ± 72 | 416 ± 89 | 526 ± 77 | 636 ± 92 | 809 ± 135 |
| 3 | BCY6136, 2 mpk, qw | 159 ± 16 | 218 ± 17 | 182 ± 22 | 182 ± 26 | 101 ± 20 | 77 ± 24 | 36 ± 4 | 41 ± 10 |
| 4 | BCY6136, 3 mpk, qw | 158 ± 5 | 241 ± 12 | 259 ± 6 | 325 ± 14 | 258 ± 12 | 246 ± 15 | 162 ± 19 | 178 ± 10 |

TABLE 43

Tumor volume trace (PG-D 19~PG-D 33)

| | | Days after the start of treatment | | | | | | |
|---|---|---|---|---|---|---|---|---|
| Gr. | Treatment | 19 | 21 | 24 | 26 | 28 | 31 | 33 |
| 1 | Vehicle, qw | 1453 ± 128 | 1661 ± 173 | — | — | — | — | — |
| 2 | BCY6136, 1 mpk, qw | 879 ± 190 | 994 ± 213 | 1253 ± 313 | 1431 ± 353 | 1507 ± 253 | 2181 ± 609 | — |
| 3 | BCY6136, 2 mpk, qw | 35 ± 9 | 33 ± 9 | 31 ± 17 | 41 ± 32 | 59 ± 45 | 82 ± 59 | 87 ± 71 |
| 4 | BCY6136, 3 mpk, qw | 171 ± 21 | 132 ± 19 | 108 ± 19 | 85 ± 15 | 81 ± 8 | 87 ± 14 | 92 ± 18 |

TABLE 44

Tumor volume trace (PG-D 35~PG-D 47)

| | | Days after the start of treatment | | | | | |
|---|---|---|---|---|---|---|---|
| Gr. | Treatment | 35 | 38 | 40 | 42 | 45 | 47 |
| 3 | BCY6136, 2 mpk, qw | 124 ± 106 | 156 ± 120 | 179 ± 142 | 239 ± 197 | 285 ± 239 | 350 ± 298 |
| 4 | BCY6136, 3 mpk, qw | 129 ± 38 | 173 ± 65 | 181 ± 65 | 269 ± 113 | 293 ± 114 | 371 ± 128 |

(iii) Tumor Growth Inhibition Analysis

Tumor growth inhibition rate for BCY6136 in the MDA-MB-231-luc xenograft model was calculated based on tumor volume measurements at day 21 after the start of treatment.

TABLE 45

Tumor growth inhibition analysis

| Gr | Treatment | Tumor Volume (mm³)[a] | T/C[b] (%) | TGI (%) | P value |
|---|---|---|---|---|---|
| 1 | Vehicle, qw | 1661 ± 173 | — | — | — |
| 2 | BCY6136, 1 mpk, qw | 994 ± 213 | 59.8 | 44.4 | p < 0.01 |
| 3 | BCY6136, 2 mpk, qw | 33 ± 9 | 2.0 | 108.4 | p < 0.001 |
| 4 | BCY6136, 3 mpk, qw | 132 ± 19 | 8.0 | 101.7 | p < 0.001 |

[a]Mean ± SEM.
[b]Tumor Growth Inhibition is calculated by dividing the group average tumor volume for the treated group by the group average tumor volume for the control group (T/C).

(e) Results Summary and Discussion

In this study, the therapeutic efficacy of BCY6136 in the MDA-MB-231-luc xenograft model was evaluated. The measured body weights and tumor volumes of all treatment groups at various time points are shown in the FIG. 18 and Tables 42 to 45.

The mean tumor size of vehicle treated mice reached 1661 mm³ on day 21. BCY6136 at 1 mg/kg (TV=994 mm³, TGI=44.4%, p<0.01) showed moderate antitumor activity, BCY6136 at 2 mg/kg (TV=33 mm³, TGI=108.4%, p<0.001) and 3 mg/kg (TV=132 mm³, TGI=101.1%, p<0.001) produced potent antitumor activity, but the tumors showed obvious re-growth from day 28. In this study, one mouse treated with BCY6136 2 mg/kg lost over 15% bodyweight during the treatment schedule, other mice maintained the bodyweight well.

Study 18: In Vivo Efficacy Test of BCY6136 in Treatment of EMT-6 Syngeneic Model in BALB/c Mice (a) Study Objective The objective of the research was to evaluate the in vivo anti-tumor efficacy of BCY6136 in treatment of EMT-6 syngeneic model in BALB/c mice.

(b) Experimental Design

| Group | Treatment | Dose (mg/kg) | N | Dosing Route | Schedule | Sample Collection |
|---|---|---|---|---|---|---|
| 1 | Vehicle | — | 5 | iv | qw * 4 | tumors from spare mice will be collected for FACS |
| 2 | BCY6136 | 3 | 5 | iv | qw * 4 | |
| 3 | BCY6136 | 1/5[b] | 5 | iv | qw * 4 | |
| 4 | BCY6136 | 0.3/3[b] | 5 | iv | qw * 4 | | a. The injection volume of each mouse is 10 ml/kg.
[b] The dosage of group 3 and group 4 was changed to 5 mpk and 3 mpk from Day 14.

(c) Experimental Methods and Procedures
(i) Cell Culture

The EMT-6 tumor cells were maintained in vitro as a monolayer culture in EMEM medium supplemented with 10% heat inactivated fetal bovine serum at 37° C. in an atmosphere of 5% $CO_2$ in air. The tumor cells were routinely subcultured twice weekly by trypsin-EDTA treatment. The cells growing in an exponential growth phase were harvested and counted for tumor inoculation.

(ii) Tumor Inoculation

Each mouse was inoculated subcutaneously at the right flank with EMT-6 tumor cells ($5 \times 10^6$) in 0.1 ml of PBS for tumor development. 44 animals were randomized when the average tumor volume reached 75 mm$^3$. The test article administration and the animal numbers in each group were shown in the experimental design table.

(iii) Testing Article Formulation Preparation

| | BCY6136 formulation | |
|---|---|---|
| Treatment | Conc. (mg/ml) | Formulation |
| Vehicle/buffer | — | 50 mM Acetate, 10% sucrose pH = 5 |
| BCY6136 | 1 | Dissolve 6.2 mg BCY6136 with 6113 ul buffer |
| BCY6136 | 0.3 | Dilute 450 μl 1 mg/ml BCY6136 stock with 1050 μl buffer |
| BCY6136 | 0.1 | Dilute 150 μl 1 mg/ml BCY6136 stock with 1350 μl buffer |
| BCY6136 | 0.03 | Dilute 45 μl 1 mg/ml BCY6136 stock with 1455 μl buffer |
| Vehicle/buffer | — | 50 mM Acetate, 10% sucrose pH = 5 |
| BCY6136 | 1 | stock |
| BCY6136 | 0.3 | Dilute 420 μl 1 mg/ml BCY6136 stock with 980 μl buffer |
| BCY6136 | 0.3 | Dilute 420 μl 1 mg/ml BCY6136 stock with 980 μl buffer |
| BCY6136 | 0.5 | Dilute 700 μl 1 mg/ml BCY6136 stock with 700 μl buffer |

(iv) Sample Collection 3 tumors from spare mice were collected for FACS on day 11. The data was supplied by biology team.

(d) Results
(i) Body Weight Change and Tumor Growth Curve

Body weight and tumor growth curve are shown in FIG. 19.

(ii) Tumor Volume Trace

Mean tumor volume over time in female BALB/c mice bearing EMT-6 syngeneic is shown in Table 46.

TABLE 46

Tumor volume trace over time

| | | Days after the start of treatment | | | | | | | | | |
|---|---|---|---|---|---|---|---|---|---|---|---|
| Gr. | Treatment | 0 | 3 | 5 | 7 | 10 | 12 | 14 | 17 | 19 | 21 |
| 1 | Vehicle, qw | 82 ± 4 | 141 ± 11 | 260 ± 24 | 443 ± 90 | 557 ± 99 | 703 ± 119 | 812 ± 139 | 948 ± 191 | 1129 ± 248 | 1499 ± 340 |
| 2 | BCY6136, 3 mpk, qw | 82 ± 4 | 58 ± 1 | 59 ± 2 | 125 ± 18 | 240 ± 23 | 322 ± 23 | 374 ± 22 | 431 ± 37 | 486 ± 50 | 561 ± 61 |
| 3 | BCY6136, 1/5[a] mpk, qw | 82 ± 4 | 108 ± 18 | 204 ± 27 | 350 ± 57 | 426 ± 49 | 588 ± 72 | 691 ± 65 | 850 ± 98 | 1018 ± 115 | 1272 ± 140 |
| 4 | BCY6136, 0.3/3[a] mpk, qw | 82 ± 4 | 130 ± 16 | 255 ± 35 | 358 ± 34 | 450 ± 67 | 607 ± 94 | 731 ± 112 | 872 ± 119 | 1082 + 133 | 1394 ± 161 |

The dosage of group 3 and group 4 was changed to 5 mpk and 3 mpk from Day 14.

(iii) Tumor Growth Inhibition Analysis

Tumor growth inhibition rate for BCY6136 in EMT-6 syngeneic model was calculated based on tumor volume measurements on day 21 after the start of treatment.

TABLE 47

Tumor growth inhibition analysis

| Gr | Treatment | Tumor Volume (mm$^3$)[a] | T/C[b] (%) | TGI (%) | P value compare with vehicle |
|---|---|---|---|---|---|
| 1 | Vehicle, qw | 1499 ± 340 | — | — | — |
| 2 | BCY6136, 3 mpk, qw | 561 ± 61 | 37.4 | 66.2 | p < 0.05 |
| 3 | BCY6136, 1/5[c] mpk, qw | 1272 ± 140 | 84.8 | 16.1 | ns |
| 4 | BCY6136, 0.3/3[c] mpk, qw | 1394 ± 161 | 93.0 | 7.4 | ns |

[a] Mean ± SEM.
[b] Tumor Growth Inhibition is calculated by dividing the group average tumor volume for the treated group by the group average tumor volume for the control group (T/C).
[c] The dosage of group 3 and group 4 was changed to 5 mpk and 3 mpk from Day 14.

(e) Results Summary and Discussion

In this study, the therapeutic efficacy of BCY6136 in EMT-6 syngeneic model was evaluated. The measured body weights and tumor volumes of all treatment groups at various time points are shown in the FIG. 19 and Tables 46 and 47.

The mean tumor size of vehicle treated mice reached 1499 mm$^3$ on day 21. BCY6136 at 3 mg/kg, qw (TV=561 mm$^3$, TGI=66.2%, p<0.05) showed obvious antitumor activity. BCY6136 at ⅕ mg/kg, qw (TV=1272 mm³, TGI=16.1%, p>0.05) and BCY6136 at 0.3/3 mg/kg, qw (TV=1394 mm³, TGI=7.4%, p>0.05) didn't show any antitumor activity.

The dosage of group 3 and group 4 was changed to 5 mpk and 3 mpk from day 14. Tumor ulceration was found in mouse 3-5 on Day 14, and the mice was deal with antibiotic cream. In this study, all mice maintained the bodyweight well.

Study 19: In Vivo Efficacy Study of BCY6136 in Treatment of NCI-N87 Xenograft in Balb/c Nude Mice (a) Study Objective The objective of the research is to evaluate the in vivo anti-tumor efficacy of BCY6136 in treatment of NCI-N87 xenograft in Balb/c nude mice.

(b) Experimental Design

| Group | Treatment | n | Dose (mg/kg) | Dosing Volume (μl/g) | Dosing Route | Schedule |
|---|---|---|---|---|---|---|
| 1 | Vehicle | 3 | — | 10 | iv | Qw |
| 2 | BCY6136 | 3 | 1 | 10 | iv | Qw |
| 3 | BCY6136 | 3 | 2 | 10 | iv | Qw |
| 4 | BCY6136 | 3 | 3 | 10 | iv | Qw |

(c) Experimental Methods and Procedures (i) Cell Culture

The NCI-N87 tumor cells were maintained in RPMI-1640 medium supplemented with 10% heat inactivated fetal bovine serum at 37° C. in an atmosphere of 5% $CO_2$ in air. The tumor cells were routinely subcultured twice weekly. The cells growing in an exponential growth phase were harvested and counted for tumor inoculation.

(ii) Tumor Inoculation

Each mouse was inoculated subcutaneously at the right flank with NCI-N87 tumor cells ($10 \times 10^6$) with matrigel (1:1) in 0.2 ml of PBS for tumor development. The animals were randomized and treatment was started when the average tumor volume reached approximately 176 mm³. The test article administration and the animal number in each group are shown in the experimental design table.

(iii) Testing Article Formulation Preparation

| Test article | Conc. (mg/ml) | Formulation |
|---|---|---|
| Vehicle | — | 50 mM Acetate 10% sucrose pH 5 |
| BCY6136 | 1 | Dissolve 4.295 mg BCY6136 in 4.214 ml Acetate buffer[1] |
| | 0.1 | Dilute 90 μl 1 mg/ml BCY6136 stock with 810 μl Acetate buffer |
| | 0.2 | Dilute 180 μl 1 mg/ml BCY6136 stock with 720 μl Acetate buffer |
| | 0.3 | Dilute 270 μl 1 mg/ml BCY6136 stock with 630 μl Acetate buffer |

[1]Acetate buffer: 50 mM Acetate 10% sucrose pH 5

(d) Results (i) Body Weight change and Tumor Growth Curve

Figure 20:
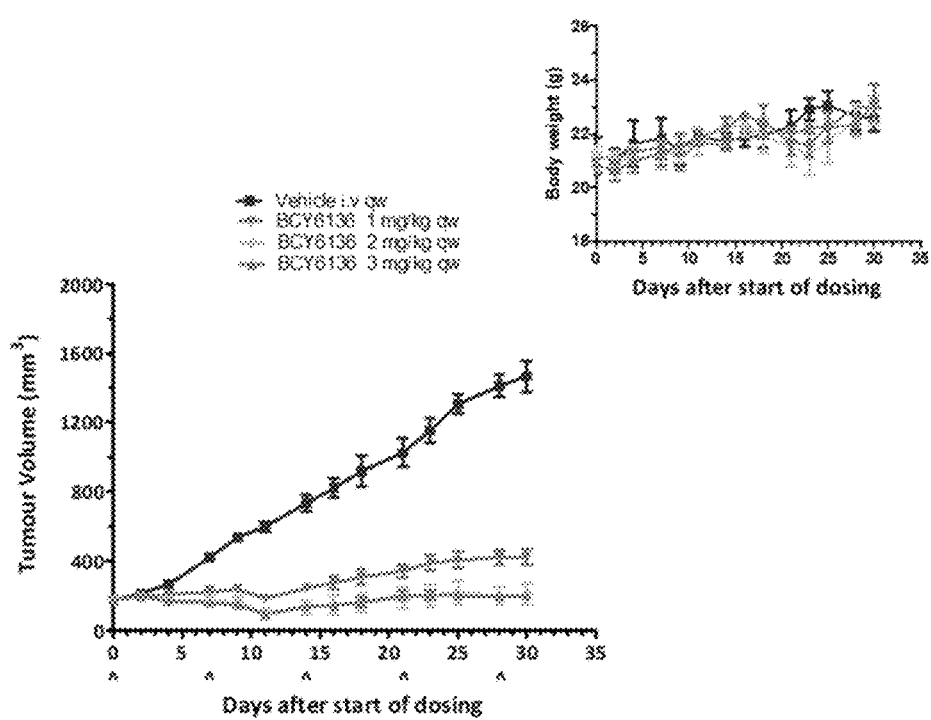
FIG. 20: Body weight changes and tumor volume traces after administering BCY6136 to female Balb/c nude mice bearing NCI-N87 xenograft. Data points represent group mean body weight.

Body weight and tumor growth curve is shown in FIG. 20.

(ii) Tumor Volume Trace

Mean tumor volume overtime in female Balb/c nude mice bearing NCI-N87 xenograft is shown in Table 48.

TABLE 48

Tumor volume trace over time

| Gr. | Treatment | Days after the start of treatment | | | | | | | |
|---|---|---|---|---|---|---|---|---|---|
| | | 0 | 2 | 4 | 7 | 9 | 11 | 14 | 16 |
| 1 | Vehicle, qw | 174 ± 7 | 213 ± 5 | 266 ± 6 | 421 ± 10 | 537 ± 17 | 598 ± 30 | 734 ± 46 | 821 ± 55 |
| 2 | BCY6136, 1 mpk, qw | 176 ± 7 | 200 ± 8 | 210 ± 14 | 224 ± 27 | 238 ± 21 | 184 ± 18 | 244 ± 23 | 276 ± 35 |
| 3 | BCY6136, 2 mpk, qw | 176 ± 18 | 197 ± 25 | 168 ± 25 | 170 ± 26 | 165 ± 34 | 96 ± 27 | 133 ± 35 | 150 ± 52 |
| 4 | BCY6136, 3 mpk, qw | 177 ± 8 | 197 ± 9 | 169 ± 7 | 158 ± 3 | 148 ± 8 | 95 ± 16 | 141 ± 12 | 145 ± 24 |

| Gr. | Treatment | Days after the start of treatment | | | | | |
|---|---|---|---|---|---|---|---|
| | | 18 | 21 | 23 | 25 | 28 | 30 |
| 1 | Vehicle, qw | 918 ± 91 | 1024 ± 83 | 1151 ± 68 | 1305 ± 57 | 1407 ± 64 | 1465 ± 90 |
| 2 | BCY6136, 1 mpk, qw | 308 ± 44 | 343 ± 37 | 390 ± 43 | 406 ± 48 | 422 ± 42 | 425 ± 47 |
| 3 | BCY6136, 2 mpk, qw | 160 ± 49 | 190 ± 63 | 203 ± 65 | 218 ± 66 | 201 ± 53 | 210 ± 60 |
| 4 | BCY6136, 3 mpk, qw | 164 ± 28 | 202 ± 28 | 205 ± 30 | 201 ± 16 | 196 ± 21 | 201 ± 22 |

(iii) Tumor Growth Inhibition Analysis

Tumor growth inhibition rate for BCY6136 in the NCI-N87 xenograft was calculated based on tumor volume measurements at day 30 after the start of treatment.

TABLE 49

Tumor growth inhibition analysis

| Group | Treatment | Tumor Volume (mm³)[a] | T/C[b] (%) | TGI (%) | P value |
|---|---|---|---|---|---|
| 1 | Vehicle, qw | 1465 ± 90 | — | — | — |
| 2 | BCY6136, 1 mpk, qw | 425 ± 47 | 29.0 | 80.7 | p < 0.001 |
| 3 | BCY6136, 2 mpk, qw | 210 ± 60 | 14.3 | 97.4 | p < 0.001 |
| 4 | BCY6136, 3 mpk, qw | 201 ± 22 | 13.7 | 98.1 | p < 0.001 |

[a]Mean ± SEM.

[b]Tumor growth inhibition is calculated by dividing the group average tumor volume for the treated group by the group average tumor volume for the control group (T/C).

(e) Results Summary and Discussion

In this study, the therapeutic efficacy of BCY6136 in the NCI-N87 model was evaluated. The measured body weight and tumor volume of all treatment groups at various time points are shown in the FIG. 20 and Tables 48 and 49.

The mean tumor size of vehicle treated mice reached 1465 mm³ on day 30. BCY6136 at 1 mg/kg, qw (TV=425 mm³, TGI=80.7%, p<0.001) and 2 mg/kg, qw (TV=210 mm³, TGI=97.4%, p<0.001) produced significant antitumor activity in a dose-dependent manner, BCY6136 at 3 mg/kg, qw (TV=201 mm³, TGI=98.1%, p<0.001) showed comparable antitumor activity with BCY6136 at 2 mpk.

In this study, no obvious body weight loss was found in all the groups during the treatment schedule.

Study 20: In Vivo Efficacy Study of BCY6136 in Treatment of SK-OV-3 Xenograft in Balb/c Nude Mice (a) Study Objective The objective of the research is to evaluate the in vivo anti-tumor efficacy of BCY6136 in treatment of SK-OV-3 xenograft in Balb/c nude mice.

(b) Experimental Design

| Group | Treatment | n | Dose (mg/kg) | Dosing Volume (ul/g) | Dosing Route | Schedule |
|---|---|---|---|---|---|---|
| 1 | Vehicle | 3 | — | 10 | iv | Qw |
| 2 | ADC | 3 | 3 | 10 | iv | Qw |
| 3 | BCY6136 | 3 | 1 | 10 | iv | Qw |
| 4 | BCY6136 | 3 | 2 | 10 | iv | Qw |
| 5 | BCY6136 | 3 | 3 | 10 | iv | Qw |

(c) Experimental Methods and Procedures (i) Cell Culture

The SK-OV-3 tumor cells were maintained in McCoy's 5a medium supplemented with 10% heat inactivated fetal bovine serum at 37° C. in an atmosphere of 5% $CO_2$ in air. The tumor cells were routinely subcultured twice weekly. The cells growing in an exponential growth phase were harvested and counted for tumor inoculation.

(ii) Tumor Inoculation

Each mouse was inoculated subcutaneously at the right flank with SK-OV-3 tumor cells ($10 \times 10^6$) with matrigel (1:1) in 0.2 ml of PBS for tumor development. The animals were randomized and treatment was started when the average tumor volume reached approximately 186 mm³. The test article administration and the animal number in each group are shown in the experimental design table.

(iii) Testing Article Formulation Preparation

| Test article | Purity | Conc. (mg/ml) | Formulation |
|---|---|---|---|
| Vehicle | — | — | 50 mM Acetate 10% sucrose pH 5 |
| BCY6136 | 98.5% | 1 | Dissolve 3.65 mg BCY6136 in 3.60 ml 50 mM Acetate buffer[1] |
|  |  | 0.1 | Dilute 90 μl 1 mg/ml BCY6136 stock with 810 μl Acetate buffer[1] |
|  |  | 0.2 | Dilute 180 μl 1 mg/ml BCY6136 stock with 720 μl Acetate buffer[1] |
|  |  | 0.3 | Dilute 270 μl 1 mg/ml BCY6136 stock with 630 μl Acetate buffer[1] |
| ADC | ADC | 0.3 | Dilute 69 μl 10.47 mg/ml ADC stock with 2331 μl ADC buffer[2] |

[1]Acetate buffer: 50 mM Acetate 10% sucrose pH 5
[2]ADC buffer: 25 mM Histidine 10% sucrose pH 5.5

(d) Results (i) Body Weight change and Tumor Growth Curve

Figure 21:
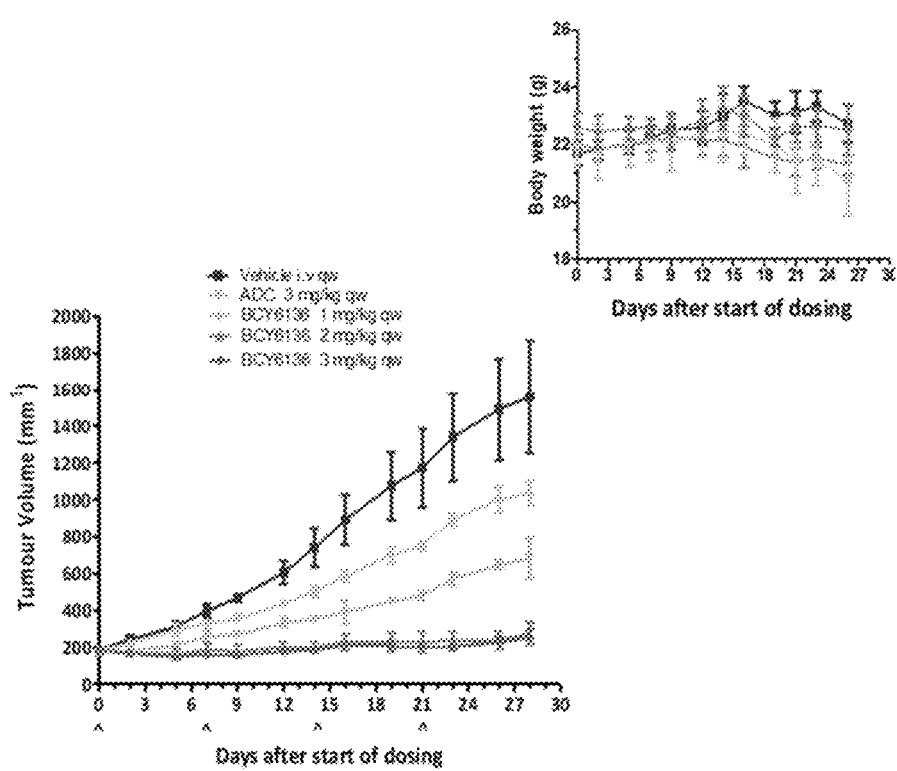
FIG. 21: Body weight changes and tumor volume traces after administering BCY6136 to female Balb/c nude mice bearing SK-OV-3 xenograft. Data points represent group mean body weight.

Body weight and tumor growth curve is shown in FIG. 21.

(ii) Tumor Volume Trace

Mean tumor volume over time in female Balb/c nude mice bearing SK-OV-3 xenograft is shown in Table 50.

TABLE 50

Tumor volume trace over time

| Gr. | Treatment | Days after the start of treatment | | | | | | |
|---|---|---|---|---|---|---|---|---|
| | | 0 | 2 | 5 | 7 | 9 | 12 | 14 |
| 1 | Vehicle, qw | 187 ± 16 | 243 ± 24 | 313 ± 28 | 399 ± 37 | 470 ± 23 | 606 ± 61 | 742 ± 103 |
| 2 | ADC, 3 mpk, qw | 187 ± 16 | 181 ± 15 | 212 ± 16 | 263 ± 35 | 268 ± 14 | 335 ± 23 | 353 ± 18 |
| 3 | BCY6136, 2 mpk, qw | 186 ± 23 | 222 ± 19 | 293 ± 34 | 331 ± 21 | 356 ± 23 | 440 ± 8 | 503 ± 28 |
| 4 | BCY6136, 2 mpk, qw | 186 ± 23 | 170 ± 18 | 164 ± 28 | 188 ± 33 | 180 ± 34 | 202 ± 29 | 200 ± 29 |
| 5 | BCY6136, 3 mpk, qw | 184 ± 24 | 168 ± 18 | 150 ± 12 | 164 ± 12 | 158 ± 8 | 180 ± 8 | 187 ± 4 |

TABLE 50-continued

Tumor volume trace over time

| | | Days after the start of treatment | | | | | |
|---|---|---|---|---|---|---|---|
| Gr. | Treatment | 16 | 19 | 21 | 23 | 26 | 28 |
| 1 | Vehicle, qw | 891 ± 133 | 1076 ± 185 | 1173 ± 214 | 1340 ± 236 | 1490 ± 273 | 1560 ± 305 |
| 2 | ADC, 3 mpk, qw | 392 ± 63 | 449 ± 4 | 481 ± 27 | 573 ± 33 | 647 ± 26 | 684 ± 111 |
| 3 | BCY6136, 2 mpk, qw | 587 ± 33 | 702 ± 43 | 752 ± 26 | 893 ± 34 | 1002 ± 68 | 1035 ± 67 |
| 4 | BCY6136, 2 mpk, qw | 230 ± 46 | 229 ± 48 | 231 ± 58 | 236 ± 49 | 240 ± 48 | 277 ± 58 |
| 5 | BCY6136, 3 mpk, qw | 212 ± 17 | 208 ± 29 | 204 ± 12 | 205 ± 17 | 227 ± 31 | 254 ± 48 |

(iii) Tumor Growth Inhibition Analysis

Tumor growth inhibition rate for BCY6136 in the SK-OV-3 xenograft was calculated based on tumor volume measurements at day 28 after the start of treatment.

TABLE 51

Tumor growth inhibition analysis

| Group | Treatment | Tumor Volume (mm³)[a] | T/C[b] (%) | TGI (%) | P value |
|---|---|---|---|---|---|
| 1 | Vehicle, qw | 1560 ± 305 | — | — | — |
| 2 | ADC, 3 mpk, qw | 684 ± 111 | 43.9 | 63.8 | p < 0.01 |
| 3 | BCY6136, 1 mpk, qw | 1035 ± 67 | 66.4 | 38.1 | p > 0.05 |
| 4 | BCY6136, 2 mpk, qw | 277 ± 58 | 17.8 | 93.3 | p < 0.001 |
| 5 | BCY6136, 3 mpk, qw | 254 ± 48 | 16.3 | 95.0 | p < 0.001 |

[a]Mean ± SEM.
[b]Tumor growth inhibition is calculated by dividing the group average tumor volume for the treated group by the group average tumor volume for the control group (T/C).

(e) Results Summary and Discussion

In this study, the therapeutic efficacy of BCY6136 in the SK-OV-3 model was evaluated. The measured body weight and tumor volume of all treatment groups at various time points are shown in the FIG. 21 and Tables 50 and 51.

The mean tumor size of vehicle treated mice reached 1560 mm³ on day 28. ADC at 3 mg/kg, qw (TV=684 mm³, TGI=63.8%, p<0.01) showed moderate anti-tumor efficacy. BCY6136 at 1 mg/kg, qw (TV=1035 mm³, TGI=38.1%, p>0.05) didn't show obvious anti-tumor activity. BCY6136 at 2 mg/kg, qw (TV=277 mm³, TGI=93.3%, p<0.001) and 3 mg/kg, qw (TV=254 mm³, TGI=95.0%, p<0.001) produced significant anti-tumor activity.

In this study, no obvious body weight loss was found in all the groups during the treatment schedule.

Study 21: In Vivo Efficacy Study of BCY6136 in Treatment of OE21 Xenograft in Balb/c Nude Mice (a) Study Objective The objective of the research is to evaluate the in vivo anti-tumor efficacy of BCY6136 in treatment of OE21 xenograft in Balb/c nude mice.

(b) Experimental Design

| Group | Treatment | n | Dose (mg/kg) | Dosing Volume (μl/g) | Dosing Route | Schedule |
|---|---|---|---|---|---|---|
| 1 | Vehicle | 3 | — | 10 | iv | qw |
| 2 | BCY6136 | 3 | 1 | 10 | iv | qw |
| 3 | BCY6136 | 3 | 2 | 10 | iv | qw |
| 4 | BCY6136 | 3 | 3 | 10 | iv | qw |

(c) Experimental Methods and Procedures (i) Cell Culture

The OE21 tumor cells were maintained in RPMI-1640 medium supplemented with 10% heat inactivated fetal bovine serum at 37° C. in an atmosphere of 5% $CO_2$ in air. The tumor cells were routinely subcultured twice weekly. The cells growing in an exponential growth phase were harvested and counted for tumor inoculation.

(ii) Tumor Inoculation

Each mouse was inoculated subcutaneously at the right flank with OE21 tumor cells ($5 \times 10^6$) with matrigel (1:1) in 0.2 ml of PBS for tumor development. The animals were randomized and treatment was started when the average tumor volume reached approximately 157 mm³. The test article administration and the animal number in each group are shown in the experimental design table.

(iii) Testing Article Formulation Preparation

| Test article | Conc. (mg/ml) | Formulation |
|---|---|---|
| Vehicle | — | 50 mM Acetate 10% sucrose pH 5 |
| BCY6136 | 1 | Dissolve 4.295 mg BCY6136 in 4.214 ml Acetate buffer[1] |
| | 0.1 | Dilute 90 μl 1 mg/ml BCY6136 stock with 810 μl Acetate buffer |
| | 0.2 | Dilute 180 μl 1 mg/ml BCY6136 stock with 720 μl Acetate buffer |
| | 0.3 | Dilute 270 μl mg/ml BCY6136 stock with 630 μl Acetate buffer |

[1]Acetate buffer: 50 mM Acetate 10% sucrose pH 5

(d) Results

Body Weight change and Tumor Growth Curve

Figure 22:
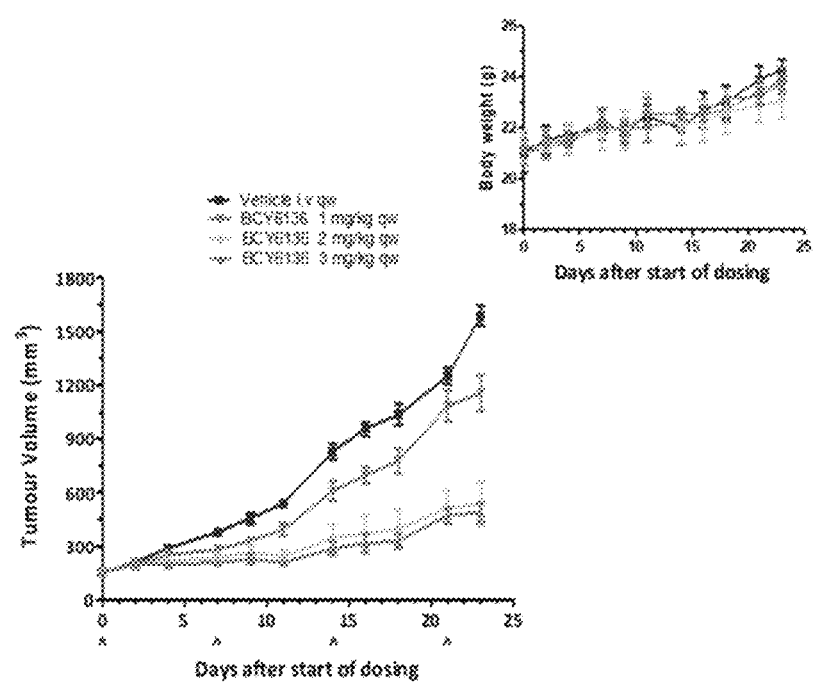
FIG. 22: Body weight changes and tumor volume traces after administering BCY6136 to female Balb/c nude mice bearing OE21 xenograft. Data points represent group mean body weight.

Body weight and tumor growth curve is shown in FIG. 22.

(ii) Tumor Volume Trace

Mean tumor volume over time in female Balb/c nude mice bearing OE21 xenograft is shown in Table 52.

TABLE 52

Tumor volume trace over time

| | | Days after the start of treatment | | | | | |
|---|---|---|---|---|---|---|---|
| Gr. | Treatment | 0 | 2 | 4 | 7 | 9 | 11 |
| 1 | Vehicle, qw | 155 ± 9 | 211 ± 16 | 291 ± 16 | 379 ± 14 | 456 ± 32 | 539 ± 13 |
| 2 | BCY6136, 1 mpk, qw | 159 ± 14 | 202 ± 28 | 251 ± 29 | 282 ± 6 | 331 ± 19 | 392 ± 35 |
| 3 | BCY6136, 2 mpk, qw | 157 ± 19 | 197 ± 13 | 219 ± 6 | 235 ± 27 | 268 ± 35 | 243 ± 37 |
| 4 | BCY6136, 3 mpk, qw | 155 ± 19 | 200 ± 16 | 197 ± 7 | 209 ± 11 | 229 ± 26 | 211 ± 14 |

| | | Days after the start of treatment | | | | |
|---|---|---|---|---|---|---|
| Gr. | Treatment | 14 | 16 | 18 | 21 | 23 |
| 1 | Vehicle, qw | 828 ± 42 | 955 ± 40 | 1035 ± 58 | 1250 ± 46 | 1586 ± 57 |
| 2 | BCY6136, 1 mpk, qw | 609 ± 56 | 694 ± 44 | 777 ± 68 | 1083 ± 85 | 1155 ± 98 |
| 3 | BCY6136, 2 mpk, qw | 346 ± 78 | 371 ± 98 | 396 ± 109 | 515 ± 94 | 537 ± 122 |
| 4 | BCY6136, 3 mpk, qw | 289 ± 38 | 318 ± 53 | 330 ± 40 | 474 ± 42 | 489 ± 51 |

(iii) Tumor Growth Inhibition Analysis

Tumor growth inhibition rate for BCY6136 in the OE21 xenograft was calculated based on tumor volume measurements at day 23 after the start of treatment.

TABLE 53

Tumor growth inhibition analysis

| Group | Treatment | Tumor Volume (mm³)[a] | T/C[b] (%) | TGI (%) | P value |
|---|---|---|---|---|---|
| 1 | Vehicle, qw | 1586 ± 57 | — | — | — |
| 2 | BCY6136, 1 mpk, qw | 1155 ± 98 | 72.8 | 30.4 | p < 0.05 |
| 3 | BCY6136, 2 mpk, qw | 537 ± 122 | 33.9 | 73.4 | p < 0.001 |
| 4 | BCY6136, 3 mpk, qw | 489 ± 51 | 30.8 | 76.7 | p < 0.001 |

[a]Mean ± SEM.
bTumor growth inhibition is calculated by dividing the group average tumor volume for the treated group by the group average tumor volume for the control group (T/C).

(e) Results Summary and Discussion

In this study, the therapeutic efficacy of BCY6136 in the OE21 model was evaluated. The measured body weight and tumor volume of all treatment groups at various time points are shown in the FIG. 22 and Tables 52 and 53.

The mean tumor size of vehicle treated mice reached 1586 mm³ on day 23. BCY6136 at 1 mg/kg, qw (TV=1155 mm³, TGI=30.4% p<0.05) showed slight anti-tumor activity. BCY6136 at 2 mg/kg, qw (TV=537 mm³, TGI=73.4%, p<0.001) and 3 mg/kg, qw (TV=489 mm³, TGI=76.7%, p<0.001) produced significant anti-tumor activity.

In this study, no obvious body weight loss was found in all the groups during the treatment schedule.

Study 22: In Vivo Efficacy Test of BCY6136 in Treatment of MOLP-8 Xenograft in CB17-SCID Mice (a) Study Objective The objective of the research is to evaluate the in vivo anti-tumor efficacy of BCY6136 in treatment of MOLP-8 xenograft in CB17-SCID mice.

(b) Experimental Design

| Group | Treatment | n | Dose (mg/kg) | Dosing Volume (µl/g) | Dosing Route | Schedule |
|---|---|---|---|---|---|---|
| 1 | Vehicle | 3 | — | 10 | iv | qw |
| 2 | BCY6136 | 3 | 1 | 10 | iv | qw |
| 3 | BCY6136 | 3 | 2 | 10 | iv | qw |
| 4 | BCY6136 | 3 | 3 | 10 | iv | qw |

(c) Experimental Methods and Procedures (i) Cell Culture

The MOLP-8 tumor cells were maintained in vitro as a monolayer culture in RMPI-1640 supplemented with 20% heat inactivated fetal bovine serum at 37° C. in an atmosphere of 5% $CO_2$ in air. The tumor cells were routinely subcultured by trypsin-EDTA treatment. The cells growing in an exponential growth phase were harvested and counted for tumor inoculation.

(ii) Tumor Inoculation

Each mouse was inoculated subcutaneously at the right flank with MOLP-8 tumor cells ($10 \times 10^6$) in 0.2 ml PBS with 50% matrigel for tumor development. 36 animals were randomized when the average tumor volume reached 141 mm³. The test article administration and the animal numbers in each group were shown in the experimental design table.

(iii) Testing Article Formulation Preparation

| Treatment | Concentration (mg/ml) | Formulation |
|---|---|---|
| Vehicle | — | 50 mM Acetate, 10% sucrose pH = 5 |
| BCY6136 | 0.1 | Dilute 90 µl 1 mg/ml BCY6136 stocks* with 810 µl buffer** |
| | 0.2 | Dilute 180 µl 1 mg/ml BCY6136 stocks* with 720 µl buffer** |
| | 0.3 | Dilute 270 µl 1 mg/ml BCY6136 stocks* with 630 µl buffer** |

*BCY6136 stocks: 10.93 mg BCY6136 dissolved to 10.93 mL 50 mM Acetate, 10% sucrose, pH = 5, and separated into individual tubes and stored at −80° C.
**Buffer: 50 mM Acetate, 10% sucrose pH = 5

(d) Results
(i) Body Weight change and Tumor Growth Curve
Body weight and tumor growth curve are shown in FIG. 23.
(ii) Tumor Volume Trace
Mean tumor volume over time in female CB17-SCID mice bearing MOLP-8 xenograft is shown in Table 54.

TABLE 54

Tumor volume trace over time

| | | Days after the start of treatment | | | | | |
|---|---|---|---|---|---|---|---|
| Gr. | Treatment | 0 | 2 | 4 | 7 | 9 | 11 | 14 |
| 1 | Vehicle, qw | 139 ± 2 | 375 ± 36 | 604 ± 28 | 984 ± 88 | 1451 ± 133 | 1981 ± 196 | 2528 ± 295 |
| 2 | BCY6136, 1 mpk, qw | 143 ± 13 | 299 ± 6 | 444 ± 49 | 576 ± 31 | 806 ± 85 | 1132 ± 170 | 1446 ± 234 |
| 3 | BCY6136, 2 mpk, qw | 140 ± 15 | 271 ± 43 | 250 ± 2 | 509 ± 23 | 662 ± 78 | 873 ± 49 | 1218 ± 144 |
| 4 | BCY6136, 3 mpk, qw | 142 ± 19 | 239 ± 67 | 197 ± 20 | 342 ± 78 | 425 ± 90 | 693 ± 133 | 938 ± 155 |

(iii) Tumor Growth Inhibition Analysis

Tumor growth inhibition rate for BCY6136 in the MOLP-8 xenograft model was calculated based on tumor volume measurements at day 14 after the start of treatment.

TABLE 55

Tumor growth inhibition analysis

| Gr | Treatment | Tumor Volume (mm$^3$)$^a$ | T/C$^b$ (%) | TGI (%) | P value compared with vehicle |
|---|---|---|---|---|---|
| 1 | Vehicle, qw | 2528 ± 295 | — | — | — |
| 2 | BCY6136, 1 mpk, qw | 1446 ± 234 | 57.2 | 45.5 | p > 0.05 |
| 3 | BCY6136, 2 mpk, qw | 1218 ± 144 | 48.2 | 54.9 | p < 0.05 |
| 4 | BCY6136, 3 mpk, qw | 938 ± 155 | 37.1 | 66.7 | p < 0.01 |

$^a$Mean ± SEM.
$^b$Tumor Growth Inhibition is calculated by dividing the group average tumor volume for the treated group by the group average tumor volume for the control group (T/C).

(e) Results Summary and Discussion

In this study, the therapeutic efficacy of BCY6136 in the MOLP-8 xenograft model was evaluated. The measured body weights and tumor volumes of all treatment groups at various time points are shown in the FIG. 23 and Tables 54 and 55.

The mean tumor size of vehicle treated mice reached 2528 mm$^3$ on day 14. BCY6136 at 1 mg/kg (TV=1146 mm$^3$, TGI=45.5%, p>0.05), 2 mg/kg (TV=1218 mm$^3$, TGI=54.9%, p<0.05) and 3 mg/kg (TV=938 mm$^3$, TGI=66.7%, p<0.01) produced dose-dependent antitumor activity, but all of dosage didn't regress the tumors in MOLP-8 xenografts. In this study, all of mice maintained the bodyweight well.

Study 23: In Vivo Efficacy Test of BCYs in Treatment of HT1080 Xenograft in BALB/c Nude Mice (a) Study Objective The objective of the research was to evaluate the in vivo anti-tumor efficacy of BCYs in treatment of HT1080 xenograft model in BALB/c nude mice.

(b) Experimental Design

| Group | Treatment | n | Dose (mg/kg) | Dosing Volume (μl/g) | Dosing Route | Schedule |
|---|---|---|---|---|---|---|
| 1 | Vehicle | 3 | — | 10 | iv | qw |
| 2 | BCY6173 | 3 | 1 | 10 | iv | qw |
| 3 | BCY6173 | 3 | 2 | 10 | iv | qw |
| 4 | BCY6173 | 3 | 3 | 10 | iv | qw |
| 5 | BCY6135 | 3 | 1 | 10 | iv | qw |
| 6 | BCY6135 | 3 | 2 | 10 | iv | qw |
| 7 | BCY6135 | 3 | 3 | 10 | iv | qw |
| 8 | BCY6136 | 3 | 2 | 10 | iv | qw |
| 9 | BCY6136 | 3 | 3 | 10 | iv | qw |
| 10 | BCY6136 | 3 | 5 | 10 | iv | qw |
| 11 | BCY6174 | 3 | 1 | 10 | iv | qw |
| 12 | BCY6174 | 3 | 2 | 10 | iv | qw |
| 13 | BCY6174 | 3 | 3 | 10 | iv | qw |
| 14 | BCY6175 | 3 | 1 | 10 | iv | qw |
| 15 | BCY6175 | 3 | 2 | 10 | iv | qw |
| 16 | BCY6175 | 3 | 3 | 10 | iv | qw |
| 17 | ADC | 3 | 3 | 10 | iv | qw |

Note:
n: animal number;
Dosing volume: adjust dosing volume based on body weight 10 μl/g.

(c) Experimental Methods and Procedures

Cell Culture

The HT1080 tumor cells will be maintained in medium supplemented with 10% heat inactivated fetal bovine serum at 37° C. in an atmosphere of 5% $CO_2$ in air. The tumor cells will be routinely subcultured twice weekly. The cells growing in an exponential growth phase will be harvested and counted for tumor inoculation.

(ii) Tumor Inoculation

Each mouse will be inoculated subcutaneously at the right flank with HT1080 tumor cells (5*10$^6$) for tumor development. The animals will be randomized and treatment will be started when the average tumor volume reaches approximately 150-200 mm$^3$. The test article administration and the animal numbers in each group are shown in the following experimental design table.

(iii) Testing Article Formulation Preparation

| Treatment | Dose (mg/ml) | Formulation |
|---|---|---|
| Vehicle | — | 50 mM Acetate/acetic acid pH 5 10% sucrose |
| BCY6173 | 1 | Dissolve 2.13 mg BCY6173 with 2.04 ml buffer |
|  | 0.1 | Dilute 90 µl 1 mg/ml BCY6173 stock with 810 µl buffer |
|  | 0.2 | Dilute 180 µl 1 mg/ml BCY6173 stock with 720 µl buffer |
|  | 0.3 | Dilute 270 µl 1 mg/ml BCY6173 stock with 630 µl buffer |
| BCY6135 | 1 | Dissolve 2 mg BCY6135 with 1.9 ml buffer |
|  | 0.1 | Dilute 90 µl 1 mg/ml BCY6135 stock with 810 µl buffer |
|  | 0.2 | Dilute 180 µl 1 mg/ml BCY6135 stock with 720 µl buffer |
|  | 0.3 | Dilute 270 µl 1 mg/ml BCY6135 stock with 630 µl buffer |
| BCY6136 | 0.2 | Dilute 200 µl 1 mg/ml BCY6136 stock with 800 µl buffer |
|  | 0.3 | Dilute 300 µl 1 mg/ml BCY6136 stock with 700 µl buffer |
|  | 0.5 | Dilute 500 µl 1 mg/ml BCY6136 stock with 500 µl buffer |
| BCY6174 | 1 | Dissolve 2.69 mg BCY6174 with 2.677 ml buffer |
|  | 0.1 | Dilute 90 µl 1 mg/ml BCY6174 stock with 810 µl buffer |
|  | 0.2 | Dilute 180 µl 1 mg/ml BCY6174 stock with 720 µl buffer |
|  | 0.3 | Dilute 270 µl 1 mg/ml BCY6174 stock with 630 µl buffer |
| BCY6175 | 1 | Dissolve 2 mg BCY6175 with 1.924 ml buffer |
|  | 0.1 | Dilute 90 µl 1 mg/ml BCY6175 stock with 810 µl buffer |
|  | 0.2 | Dilute 180 µl 1 mg/ml BCY6175 stock with 720 µl buffer |
|  | 0.3 | Dilute 270 µl 1 mg/ml BCY6175 stock with 630 µl buffer |
| ADC | 0.3 | Dilute 25.78 µl 10.47 mg/ml ADC stock with 874.22 µl 25 mM Histidine pH 7 10% sucrose |

(d) Results

Body Weight Change and Tumor Growth Curve

Body weight and tumor growth curve are shown in FIGS. 24 to 29.

(ii) Tumor Volume Trace

Mean tumor volume over time in female Balb/c nude mice bearing HT1080 xenograft is shown in Table 56.

TABLE 56

Tumor volume trace over time

| | | Days after the start of treatment | | | | | | |
|---|---|---|---|---|---|---|---|---|
| Gr. | Treatment | 0 | 2 | 4 | 7 | 9 | 11 | 14 |
| 1 | Vehicle, qw | 179 ± 22 | 312 ± 84 | 529 ± 135 | 886 ± 207 | 1185 ± 172 | 1467 ± 224 | 1737 ± 258 |
| 2 | BCY6173 1 mpk, qw | 178 ± 26 | 276 ± 8 | 328 ± 73 | 594 ± 62 | 745 ± 22 | 960 ± 53 | 1074 ± 150 |
| 3 | BCY6173, 2 mpk, qw | 178 ± 28 | 277 ± 61 | 262 ± 125 | 309 ± 238 | 425 ± 334 | 436 ± 323 | 480 ± 347 |
| 4 | BCY6173, 3 mpk, qw | 179 ± 43 | 182 ± 71 | 133 ± 88 | 87 ± 68 | 77 ± 65 | 60 ± 54 | 47 ± 42 |
| 5 | BCY6135 1 mpk, qw | 178 ± 22 | 267 ± 66 | 262 ± 58 | 436 ± 67 | 599 ± 89 | 703 ± 36 | 871 ± 28 |
| 6 | BCY6135 2 mpk, qw | 178 ± 23 | 176 ± 48 | 117 ± 43 | 70 ± 23 | 67 ± 23 | 52 ± 21 | 62 ± 7 |
| 7 | BCY6135 3 mpk, qw | 177 ± 39 | 178 ± 79 | 92 ± 67 | 62 ± 46 | 62 ± 51 | 57 ± 51 | 44 ± 40 |
| 8 | BCY6136 2 mpk, qw | 178 ± 19 | 249 ± 22 | 115 ± 8 | 126 ± 53 | 158 ± 71 | 140 ± 89 | 245 ± 116 |
| 9 | BCY6136 3 mpk, qw | 178 ± 36 | 168 ± 21 | 72 ± 18 | 22 ± 7 | 21 ± 15 | 8 ± 6 | 3 ± 2 |
| 10 | BCY6136 5 mpk, qw | 178 ± 26 | 165 ± 33 | 52 ± 10 | 18 ± 7 | 9 ± 4 | 5 ± 2 | 2 ± 1 |
| 11 | BCY6174 1 mpk, qw | 180 ± 35 | 231 ± 19 | 226 ± 29 | 432 ± 37 | 602 ± 63 | 742 ± 62 | 1066 ± 130 |
| 12 | BCY6174 2 mpk, qw | 178 ± 31 | 203 ± 50 | 123 ± 29 | 216 ± 47 | 291 ± 40 | 326 ± 68 | 532 ± 91 |
| 13 | BCY6174 3 mpk, qw | 178 ± 33 | 195 ± 13 | 110 ± 39 | 58 ± 23 | 34 ± 17 | 21 ± 11 | 11 ± 7 |
| 14 | BCY6175 1 mpk, qw | 178 ± 27 | 248 ± 62 | 244 ± 74 | 347 ± 18 | 435 ± 18 | 558 ± 38 | 769 ± 26 |
| 15 | BCY6175 2 mpk, qw | 178 ± 22 | 223 ± 42 | 158 ± 59 | 116 ± 35 | 156 ± 52 | 166 ± 51 | 295 ± 88 |
| 16 | BCY6175 3 mpk, qw | 179 ± 39 | 189 ± 48 | 116 ± 50 | 43 ± 18 | 33 ± 18 | 25 ± 13 | 11 ± 9 |
| 17 | ADC 3 mpk, qw | 180 ± 26 | 158 ± 30 | 58 ± 8 | 18 ± 2 | 7 ± 1 | 2 ± 2 | 0 ± 0 |

(iii) Tumor Growth Inhibition Analysis

Tumor growth inhibition rate for BCYs in the HT1080 xenograft model was calculated based on tumor volume measurements at day 14 after the start of treatment.

TABLE 57

Tumor growth inhibition analysis

| Gr | Treatment | Tumor Volume (mm³)[a] | T/C[b] (%) | TGI (%) | P value compare |
|---|---|---|---|---|---|
| 1 | Vehicle, qw | 1737 ± 258 | — | — | — |
| 2 | BCY6173, 1 mpk, | 1074 ± 150 | 61.8 | 42.5 | p > 0.05 |
| 3 | BCY6173, 2 mpk, | 480 ± 347 | 27.6 | 80.6 | p < 0.05 |
| 4 | BCY6173, 3 mpk, | 47 ± 42 | 2.7 | 108.4 | p < 0.01 |
| 5 | BCY6135, 1 mpk, | 871 ± 28 | 50.1 | 55.5 | p < 0.01 |
| 6 | BCY6135, 2 mpk, | 62 ± 7 | 3.5 | 107.5 | p < 0.001 |
| 7 | BCY6135, 3 mpk, | 44 ± 40 | 2.5 | 108.6 | p < 0.001 |
| 8 | BCY6136, 2 mpk, qw | 245 ± 116 | 14.1 | 95.7 | p < 0.001 |
| 9 | BCY6136, 3 mpk, | 3 ± 2 | 0.2 | 111.2 | p < 0.001 |
| 10 | BCY6136, 5 mpk, | 2 ± 1 | 0.1 | 111.3 | p < 0.001 |
| 11 | BCY6174, 1 mpk, | 1066 ± 130 | 61.4 | 43.1 | p < 0.05 |
| 12 | BCY6174, 2 mpk, qw | 532 ± 91 | 30.6 | 77.3 | p < 0.01 |
| 13 | BCY6174, 3 mpk, | 11 ± 7 | 0.6 | 110.7 | p < 0.001 |
| 14 | BCY6175, 1 mpk, | 769 ± 26 | 44.3 | 62.1 | p < 0.01 |
| 15 | BCY6175, 2 mpk, | 295 ± 88 | 17.0 | 92.5 | p < 0.001 |
| 16 | BCY6175, 3 mpk, | 11 ± 9 | 0.6 | 110.8 | p < 0.001 |
| 17 | ADC, 3 mpk, qw | 0 ± 0 | 0.0 | 111.5 | — |

[a]Mean ± SEM.
[b]Tumor Growth Inhibition is calculated by dividing the group average tumor volume for the treated group by the group average tumor volume for the control group (T/C).

(e) Results Summary and Discussion

In this study, the therapeutic efficacy of BCYs in the HT1080 xenograft model was evaluated. The measured body weights and tumor volumes of all treatment groups at various time points are shown in the FIGS. 24 to 29 and Tables 56 and 57.

The mean tumor size of vehicle treated mice reached 1737 mm³ on day 14.

BCY6173 at 1 mg/kg, qw (TV=1074 mm³, TGI=42.5%, p>0.05), 2 mg/kg, qw (TV=480 mm³, TGI=80.6%, p<0.05) and 3 mg/kg, qw (TV=7 mm³, TGI=108.4%, p<0.01) produced dose-dependent antitumor activity.

BCY6135 at 1 mg/kg, qw (TV=871 mm³, TGI=55.5%, p<0.01), 2 mg/kg, qw (TV=62 mm³, TGI=107.5%, p<0.001) and 3 mg/kg, qw (TV=44 mm³, TGI=108.6%, p<0.001) produced dose-dependent antitumor activity.

BCY6136 at 2 mg/kg, qw (TV=345 mm³, TGI=95.7%, p<0.001), 3 mg/kg, qw (TV=3 mm³, TGI=111.2%, p<0.001) and 5 mg/kg, qw (TV=2 mm³, TGI=111.3%, p<0.001) showed potent anti-tumor activity.

BCY6174 at 1 mg/kg, qw (TV=1066 mm³, TGI=43.1%, p<0.05), 2 mg/kg, qw (TV=532 mm³, TGI=77.3%, p<0.01) and 3 mg/kg, qw (TV=11 mm³, TGI=110.7%, p<0.001) produced dose-dependent antitumor activity.

BCY6175 at 1 mg/kg, qw (TV=769 mm³, TGI=62.1%, p<0.01), 2 mg/kg, qw (TV=295 mm³, TGI=92.5%, p<0.001) and 3 mg/kg, qw (TV=11 mm³, TGI=110.8%, p<0.001) produced dose-dependent antitumor activity.

ADC at 3 mg/kg, qw (TV=0 mm³, TGI=111.5%) completely eradicated the tumors by day 14.

The invention claimed is:

1. A method for suppressing or treating a disease or disorder characterized by overexpression of EphA2 in diseased tissue in a patient, the method comprising administering to the patient a peptide ligand specific for EphA2 comprising a polypeptide comprising three cysteine residues, separated by two loop sequences, and a non-aromatic molecular scaffold which forms covalent bonds with the cysteine residues of the polypeptide, such that two polypeptide loops are formed on the molecular scaffold, wherein the peptide ligand comprises the amino acid sequence:

(SEQ ID NO: 1)
$C_i$(HyP)LVNPLC$_{ii}$LHP(D-Asp)W(HArg)C$_{iii}$;

wherein HyP is hydroxyproline, HArg is homoarginine, and $C_i$, $C_{ii}$, and $C_{iii}$ represent first, second, and third cysteine residues, respectively, or a pharmaceutically acceptable salt thereof.

2. The method of claim 1, wherein the molecular scaffold is 1,1',1''-(1,3,5-triazinane-1,3,5-triyl)triprop-2-en-1-one (TATA).

3. The method of claim 1, wherein the peptide ligand comprises the amino acid sequence:

(SEQ ID NO: 2)
(β-Ala)-Sar$_{10}$-A(HArg)D-C$_i$(HyP)LVNPLC$_{ii}$LHP(D-Asp)W(HArg)C$_{iii}$ (BCY6099);

wherein Sar is sarcosine, HArg is homoarginine and HyP is hydroxyproline.

4. The method of claim 1, wherein the peptide ligand is in the form of a free acid.

5. The method of claim 1, wherein the pharmaceutically acceptable salt is selected from a sodium salt, a potassium salt, a calcium salt, and an ammonium salt.

6. The method of claim 1, wherein the EphA2 is human EphA2.

7. The method of claim 1, wherein the peptide ligand is conjugated to one or more effector and/or functional groups to form a drug conjugate.

8. The method of claim 7, wherein the effector and/or functional group is a cytotoxic agent.

9. The method of claim 8, wherein the cytotoxic agent is MMAE.

10. The method of claim 8, wherein the drug conjugate comprises a linker between the peptide ligand and the cytotoxic agent.

11. The method of claim 10, wherein the cytotoxic agent is MMAE and the linker is selected from: -Val-Cit-, -Trp-Cit-, -Val-Lys-, -D-Trp-Cit-, -Ala-Ala-Asn-, D-Ala-Phe-Lys-, and -Glu-Pro-Cit-Gly-hPhe-Tyr-Leu-(SEQ ID NO: 3).

12. The method of claim 11, wherein the cytotoxic agent is MMAE and the linker is -Val-Cit-.

13. The method of claim 10, wherein the cytotoxic agent is DM1 and the linker is selected from: —S—S—, —SS(SO$_3$H)—, —SS-(Me)-, -(Me)-SS-(Me)-, —SS-(Me$_2$)- and —SS-(Me)-SO$_3$H—.

14. The method of claim 13, wherein the cytotoxic agent is DM1 and the linker is selected from: —S—S— and —SS(SO$_3$H)—.

15. The method of claim 7, wherein the drug conjugate is selected from BCY6027, BCY6028, BCY6135, BCY6136, BCY6173, BCY6174, and BCY6175.

16. The method of claim 7, wherein the drug conjugate is selected from BCY6135, BCY6136, BCY6173, BCY6174, and BCY6175.

17. The method of claim 7, wherein the drug conjugate is BCY6136.

18. The method of claim 1, wherein the disease or disorder is cancer.

19. The method of claim 18, wherein the cancer is selected from prostate cancer, lung cancer, breast cancer, gastric cancer, ovarian cancer, oesophageal cancer, multiple myeloma, and fibrosarcoma.

20. The method of claim 1, wherein the patient is identified as having an increased copy number variation (CNV) of EphA2.

* * * * *